United States Patent
D'Souza et al.

(10) Patent No.: US 9,968,684 B2
(45) Date of Patent: May 15, 2018

(54) POLYMER-NSAID CONJUGATE

(71) Applicant: POLYACTIVA PTY LTD, Melbourne, Victoria (AU)

(72) Inventors: Asha Marina D'Souza, Carnegie (AU); Andrew Craig Donohue, Bentleigh East (AU); Russell John Tait, Balwyn (AU); Florian Hans Maximilian Graichen, Antwerp (BE); Sarah Man Yee Ng, Ascot Vale (AU); Adrian Sulistio, Glen Iris (AU)

(73) Assignee: POLYACTIVA PTY LTD, Melbourne, Victoria (AU)

(*) Notice: Subject to any disclaimer, the term of this patent is extended or adjusted under 35 U.S.C. 154(b) by 0 days. days.

(21) Appl. No.: 14/409,612

(22) PCT Filed: Jun. 26, 2013

(86) PCT No.: PCT/AU2013/000688
§ 371 (c)(1),
(2) Date: Dec. 19, 2014

(87) PCT Pub. No.: WO2014/000033
PCT Pub. Date: Jan. 3, 2014

(65) Prior Publication Data
US 2015/0150999 A1    Jun. 4, 2015

Related U.S. Application Data

(60) Provisional application No. 61/664,305, filed on Jun. 26, 2012.

(51) Int. Cl.
*A61K 47/48* (2006.01)
*A61K 31/407* (2006.01)
(Continued)

(52) U.S. Cl.
CPC ...... *A61K 47/48192* (2013.01); *A61K 31/192* (2013.01); *A61K 31/196* (2013.01);
(Continued)

(58) Field of Classification Search
None
See application file for complete search history.

(56) References Cited

U.S. PATENT DOCUMENTS

| | | | |
|---|---|---|---|
| 2007/0025956 A1* | 2/2007 | Burton | C08G 65/329 424/78.37 |
| 2007/0292352 A1* | 12/2007 | Marnett | A61K 31/405 424/9.6 |
| 2011/0243884 A1* | 10/2011 | O'Shea | C07C 69/40 424/78.36 |

FOREIGN PATENT DOCUMENTS

| | | |
|---|---|---|
| WO | WO 86/05485 A1 | 9/1986 |
| WO | WO 95/04030 A1 | 2/1995 |

(Continued)

OTHER PUBLICATIONS

Babazadeh, "Design, Synthesis and in Vitro Evaluation of Vinyl Ether Type Polymeric Prodrugs of Ibuprofen, Ketoprofen and Naproxen," International Journal of Pharmaceuticals, vol. 356, pp. 167-173, Jan. 2008.

(Continued)

*Primary Examiner* — Jeffrey Washville
(74) *Attorney, Agent, or Firm* — Foley & Lardner LLP

(57) ABSTRACT

The invention relates to polymer-drug conjugate for delivering a substituted alkanoic acid non-steroidal anti-inflammatory drug (NSAID). The invention also relates to drug delivery systems comprising the polymer-NSAID conjugate. The polymer-NSAID conjugates comprise a substituted (Continued)

alkanoic acid non-steroidal anti-inflammatory drug (NSAID) conjugated to a biodegradable polymer backbone by an ester linkage.

20 Claims, 8 Drawing Sheets

(51) Int. Cl.
 A61K 31/405 (2006.01)
 A61K 31/196 (2006.01)
 A61K 31/192 (2006.01)
 A61K 31/416 (2006.01)
 A61K 47/60 (2017.01)
 A61K 47/59 (2017.01)
 A61K 31/4745 (2006.01)

(52) U.S. Cl.
 CPC .......... *A61K 31/405* (2013.01); *A61K 31/407* (2013.01); *A61K 31/416* (2013.01); *A61K 47/59* (2017.08); *A61K 47/593* (2017.08); *A61K 47/60* (2017.08); *A61K 31/4745* (2013.01)

(56) References Cited

FOREIGN PATENT DOCUMENTS

| WO | WO 2006/138463 A2 | 12/2006 |
| WO | WO 2007/149456 A2 | 12/2007 |
| WO | WO 2009/147372 A2 | 12/2009 |
| WO | WO 2010/013279 A2 | 2/2010 |
| WO | WO 2010/040188 A1 | 4/2010 |

OTHER PUBLICATIONS

International Search Report dated Aug. 16, 2013 in application No. PCT/AU2013/000688.

Abordo et al., "Part 3. 2-formylphenyl esters of indomethacin, ketoprofen and ibuprofen and 6-substituted 2-formyl and 2-acylphenyl esters of asparin," Farmaco (Lausanne), vol. 53, No. 2, pp. 95-101, Feb. 1998.

Supplementary European Search Report dated Dec. 14, 2015 in application No. EP 13 80 9454.

Davaran et al., "Syntehsis and Hydrolysis of Polyurethanes Containing Ibuprofen Pendent Groups," Journal of Bioactive and Compatible Polymers, (Jan. 1997) vol. 12 pp. 47-58.

* cited by examiner

POLYMER-NSAID CONJUGATE

FIELD OF THE INVENTION

The present invention relates in general to polymer-drug conjugates. In particular, the invention relates to polymer-drug conjugates wherein the conjugated drug is a non-steroidal anti-inflammatory drug (NSAID), to a method of delivering a NSAID to a subject, to a drug delivery system comprising a polymer-NSAID conjugate, to a method of preparing polymer-NSAID conjugates, and to a medical device comprising polymer-NSAID conjugates.

BACKGROUND OF THE INVENTION

The targeted and controlled delivery of drugs is an area of considerable current interest. The site-specific delivery of a drug to a subject is a highly desirable feature for the treatment of many different conditions. Implantation of a device comprising a drug(s) in the body of a subject (human or animal) can be desirable to improve the efficacy and safety of the drug(s). Certain sites in a subject may require sophisticated delivery devices to overcome barriers for effective drug delivery. For example, some sites have a limited volume for administration of a device and require a device that has a high dose loading to ensure the device volume is kept to a minimum. Furthermore, such devices ideally should have material properties that ensure the subject does not experience any discomfort after the implant is placed. For example, administration of a solid implant inside the synovium of a load bearing joint is likely to damage joint cartilage. One mode of delivering a drug to a subject involves the use of a polymer to carry/retain the drug to/at a specific location.

An example of such a polymer/drug delivery system utilises an admixture of a polymer with a drug, wherein the drug is blended within the polymer matrix. However, such mere admixtures generally result in poor control over the release of the drug, with a "burst effect" of drug release often occurring immediately after administration. This can lead to problems with rapid discharge of the entire dose and a significant change in the physical properties of the admixture as the drug is released. In addition, such admixtures have limited dose loading capacity resulting in a prohibitively large device for convenient administration to some sites in a subject.

A further example of a polymer/drug delivery system is based on the polymerisation of a drug(s) with other monomers (or itself) so as to incorporate the drug as part of the backbone polymer chain. Such a system is described by Uhlrich in U.S. Pat. No. 6,613,807, WO2008/128193, WO94/04593 and U.S. Pat. No. 7,122,615. However, such "polymerised" drugs also generally result in inefficient release of the drug as the release of the drug occurs via inactive intermediates. Furthermore, the resulting polymer material generally has quite poor physical properties.

Still a further example of a polymer/drug delivery system utilises a drug covalently bound to a polymer so as to form a so called polymer-drug conjugate (see Ruth Duncan *Nature Reviews: Drug Discovery* 2003:2, 347-360). Such polymer-drug conjugates are typically formed by covalently attaching a drug to a preformed polymer backbone. However, the synthesis of such covalently bound systems can be problematic. In particular, steric and thermodynamic constraints can affect the amount of drug that can be covalently attached, which in turn can reduce control over the release of the drug. Furthermore, there is limited scope to modify the physical properties of the resulting polymer-drug conjugate material so that it can be modified to aid comfort after administration.

Non-steroidal anti-inflammatory drugs (NSAIDs) are used to treat inflammation. For many diseases, such as osteoarthritis, site specific delivery of the NSAID is desirable either to overcome side-effect limitations (e.g. gastrointestinal and cardiovascular risk associated with chronic oral NSAIDs) or efficacy limitations (e.g. topical use of NSAIDs) of existing therapy (Segal, L, et al., Priority Settings in Osteoarthritis. *Centre for Health Economics Report*, November 2004).

An opportunity therefore remains to develop new polymer or drug delivery systems which address or ameliorate one or more disadvantages or shortcomings associated with existing systems and/or their method of manufacture, or to at least provide a useful alternative to such systems and their method of manufacture.

SUMMARY OF THE INVENTION

The present invention provides a polymer-NSAID conjugate comprising a biodegradable polymer backbone and a non-steroidal anti-inflammatory drug (NSAID) conjugated pendant to the polymer backbone via an aryl ester group.

In one aspect, the present invention provides a polymer-NSAID conjugate comprising a biodegradable polymer backbone and a non-steroidal anti-inflammatory drug (NSAID) conjugated to the polymer backbone, wherein the conjugate comprises as a part of its polymer backbone an ester linked moiety of formula (I):

where:
R comprises an optionally substituted aliphatic or an optionally substituted aryl;
X is a bond or a linking group;
Ar is an optionally substituted aryl;
D is the carboxylic acid residue of the ester formed with a substituted alkanoic acid NSAID; and
n is an integer selected from 0 and 1,
with the proviso that when R comprises an optionally substituted aliphatic then n is 1, and when R comprises an optionally substituted aryl then n is 0 or 1.

In embodiments of a polymer-NSAID conjugate of the invention, R comprises an optionally substituted aliphatic or an optionally substituted aryl, and n is 1.

In some embodiments of a polymer-NSAID conjugate of the invention, the moiety of formula (I) has a structure of formula (Ia):

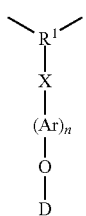

(Ia)

where:
R¹ comprises an optionally substituted aliphatic;
X is a bond or a linking group;
Ar is an optionally substituted aryl;
D is the carboxylic acid residue of the ester formed with a substituted alkanoic acid NSAID; and
n is 1.

In some embodiments of a polymer-NSAID conjugate of the invention, the moiety of formula (I) has a structure of formula (Ib):

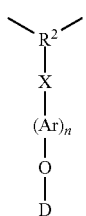

(Ib)

where:
R² comprises an optionally substituted aryl;
X is a bond or a linking group;
Ar is an optionally substituted aryl;
D is the carboxylic acid residue of the ester formed with a substituted alkanoic acid NSAID; and
n is an integer selected from 0 and 1,
with the proviso that when n is 0 then X is a bond.

In one form of a polymer-NSAID conjugate of the invention, Ar comprises from 5 to 12 ring members. In some embodiments, Ar is an optionally substituted $C_5$-$C_{12}$ aryl.

In some embodiments of a polymer-NSAID conjugate of the invention, X is an optionally substituted linking group comprising a functional group selected from the group consisting of —O—, —C(O)O—, —OC(O)—, —C(O)—, —OC(O)NH—, —NHC(O)O—, —OC$_6$H$_4$O—, —OC(O)[CH$_2$]$_n$— where n=1 to 5, —C(O)NR$^a$— and —NR$^a$C(O)—, where R$^a$ is H or $C_1$-$C_4$ alkyl.

In some embodiments the group —X—(Ar)n-O— is —OC(O)—$C_{5-12}$aryl-O—.

In one form of a polymer-NSAID conjugate of the invention the moiety of formula (I) is:

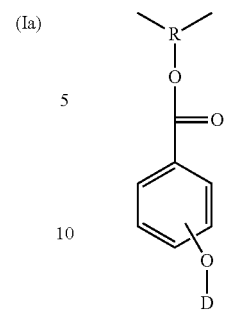

In another form of a polymer-NSAID conjugate of the invention the moiety of formula (I) is:

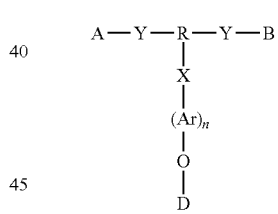

In some embodiments of polymer-NSAID conjugates of the invention, the polymer backbone comprises a polymer selected from the group consisting of polyester polymers, polyanhydride polymers, polycarbonate polymers, polyamide polymers, polyimide polymers, polyurethane polymers, polyurea polymers, polysaccharides, polypeptides, copolymers thereof, and combinations thereof.

In some embodiments of a polymer-NSAID conjugate of the invention, the conjugate comprises as a part of its polymer backbone a moiety of formula (II):

$$A-Y-R-Y-B$$
$$|$$
$$X$$
$$|$$
$$(Ar)_n$$
$$|$$
$$O$$
$$|$$
$$D$$

(II)

where:
A and B, which may be the same or different, each represent a biodegradable polymer backbone and are (i) attached to the —Y—R(X—(Ar)n-O-D)-Y— moiety as shown in formula (II) via a biodegradable moiety, and (ii) optionally, at least one of A and B comprises a hydrophilic group;
R comprises an optionally substituted hydrocarbon or an optionally substituted aryl;
Y at each occurrence is independently selected from the group consisting of —O—, —C(O)— and —NR$^a$—, where R$^a$ is H or $C_1$-$C_4$ alkyl;
X is a bond or a linking group;
Ar is an optionally substituted aryl;
D is the carboxylic acid residue of the ester formed with a substituted alkanoic acid NSAID; and
n is an integer selected from 0 and 1,
with the proviso that when R comprises an optionally substituted aliphatic then n is 1, and when R comprises an optionally substituted aryl then n is 0 or 1.

In one form of a polymer-NSAID conjugate, the moiety of formula (II) has a structure of formula (IIc):

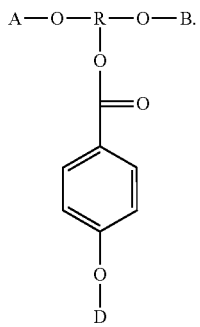

(IIc)

In another form of a polymer-NSAID conjugate, the moiety of formula (II) has a structure of formula (IIe):

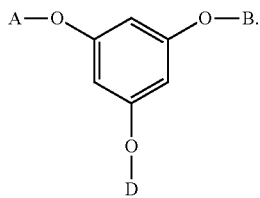

(IIe)

In some embodiments of a polymer-NSAID conjugate of the invention, A and B independently comprise a polymer selected from the group consisting of polyurethanes, polyesters, poly(urethane-ethers), poly(ester-ethers), poly(urethane-esters), and poly(ester-urethanes).

Polymer-NSAID conjugates of the invention may comprise a hydrophilic group. In such embodiments, the hydrophilic group may be incorporated in the conjugate as part of the string of atoms forming the polymer backbone chain, or as part of a pendant group that is covalently attached to and pendant from the polymer backbone chain. The polymer conjugates may comprise a combination of in-chain and pendant hydrophilic groups.

In some embodiments, the hydrophilic group comprises a moiety comprising an active-hydrogen group, wherein the active-hydrogen group is selected from the group consisting of hydroxy, amine, carboxylic acid, and combinations thereof.

In some embodiments, the hydrophilic group is provided by or derived from at least one active hydrogen group containing compound. The active hydrogen group containing compound may be selected from the group consisting of low molecular weight diols (for example C2-C4 diols, such as ethylene glycol, propane diol, propylene glycol, butane diol etc), low molecular weight triols (for example glycerol, etc), low molecular weights polyols (for example sugar alcohols, such as mannitol, xylitol, sorbitol, etc), amino alcohols (for example ethanolamine, choline, etc), amino acids (lysine, glutamic acid etc), lactic acid, glycolic acid, hydroxy acids (for example, hydroxybutyric acid etc), 1,5-dioxepan-2-one, glycerol acetate, glycerol phosphate, or combinations thereof.

In one set of embodiments, the hydrophilic group comprises a hydrophilic polymer or oligomer. The hydrophilic polymer or oligomer may comprise at least one active-hydrogen group, wherein the active-hydrogen group is selected from the group consisting of hydroxy, amine, carboxylic acid, and combinations thereof.

The hydrophilic polymer or oligomer may be derived from one or more monomers comprising an active-hydrogen group. An active-hydrogen containing monomer is able to polymerise with one or more co-monomers of compatible functionality to form a hydrophilic polymer or oligomer. An active-hydrogen containing monomer may comprise an active-hydrogen group selected from the group consisting of hydroxy, amine, carboxylic acid, and combinations thereof.

In some embodiments, the active-hydrogen containing monomer is at least one selected from the group consisting of low molecular weight diols (for example C2-C4 diols, such as ethylene glycol, propane diol, propylene glycol, butane diol etc), low molecular weight triols (for example glycerol, etc), low molecular weights polyols (for example sugar alcohols, such as mannitol, xylitol, sorbitol, etc), amino alcohols (for example ethanolamine, choline, etc), amino acids (lysine, glutamic acid etc), lactic acid, glycolic acid, hydroxy acids (for example, hydroxybutyric acid etc), 1,5-dioxepan-2-one, glycerol acetate, glycerol phosphate, or combinations thereof. Such active-hydrogen group containing monomers may homopolymerise or copolymerise with a monomer of compatible functionality under suitable conditions to provide a hydrophilic polymer or oligomer. In other embodiments, the hydrophilic group comprises a hydrophilic polymer or oligomer selected from the group consisting of poly(ethylene glycol), poly(lactic acid-co-glycolic acid) (PLGA), poly(1,5-dioxepan-2-one) (PDOO), poly(glycerol acetate) (PGAc), poly(hydroxy butyrate),), poly(glycerol phosphate), an amino acid polymer (such as polylysine, polyglutamic acid, etc), an amino acid oligomer, combinations thereof, or copolymers thereof.

In some embodiments of a polymer-NSAID conjugate of the invention, D is the acid residue of an alkanoic acid NSAID of formula (III):

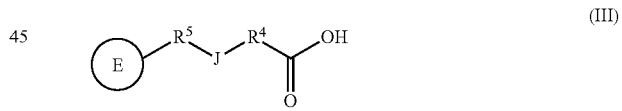

(III)

where:

E represents an optionally substituted ring system;

J is selected from the group consisting of a bond or a functional group;

$R^4$ and $R^5$ are each independently selected from the group consisting of a bond and an optionally substituted aliphatic.

In one form, E is selected from the group consisting of an optionally substituted alicyclic ring system and an optionally substituted aryl ring system. In some embodiments, E is selected from the group consisting of an optionally substituted 5 to 16 membered ring system, an optionally substituted 5 to 12 membered ring system, and an optionally substituted 5 to 6 membered ring system.

The NSAID of formula (III) may have a structure of formula (IIIa):

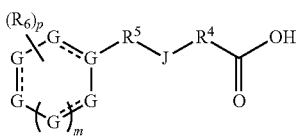

(IIIa)

where:
G at each occurrence is independently selected from the group consisting of a carbon atom and a heteroatom;
-------- represents an optional bond;
$R^6$ is a substituent group;
p represents the number of substituent groups and is an integer in the range of from 0 to 5;
m is 0 or 1; and
$R^4$, $R^5$ and J are as defined in formula (III).

In formula (IIIa), $R^4$ may be an optionally substituted $C_1$-$C_2$ hydrocarbyl, and J and $R^3$ may each represent a bond.

In some specific embodiments of a polymer-NSAID conjugate of the invention, D is the acid residue of an alkanoic acid NSAID selected from the group consisting of aceclofenac, alminoprofen, amfenac, carprofen, diclofenac, enfenamic acid, etodolac, flufenamic acid, meclofenamic acid, mefenamic acid, niflumic acid, tolfenamic acid, bendazac, benoxaprofen, bermoprofen, bucloxic acid, butibufen, cinmetacin, clidanac, clopirac, dexibuprofen, dexketoprofen, felbinac, fenbufen, fenclozic acid, fenoprofen, fentiazac, flunoxaprofen, flunixin, flurbiprofen, ibuprofen, indomethacin, isofezolac, isoxepac, ketoprofen, licofelone, lonazolac, loxoprofen, lumiracoxib, metiazinic acid, mofezolac, naproxen, oxaprozin, pirazolac, pirprofen, pranoprofen, protizinic acid, sulindac, suprofen, tiaprofenic acid, tolmetin, bermoprofen, bucloxic acid, isoxepac, ketoprofen, loxoprofen, zaltoprofen, balsalazide, fendosal, olsalazine, ximoprofen, mesalamine, sulfasalazine, acetylsalicylsalicylic acid, alclofenac, aspirin, benoxaprofen, 5-bromosalicylic acid acetate, cinchophen, diacerein, dipyrocetyl, fosfosal, ibufenac, indoprofen, clometacin, ketorolac, zomepirac, actarit, clonixin, salicylamide O-acetic acid, diflunisal, gentisic acid, and salsalate.

In particular embodiments, D is the acid residue of an alkanoic acid NSAID selected from the group consisting of diclofenac, ketorolac and indomethacin.

In another aspect, the present invention provides a polymer-NSAID conjugate comprising a biodegradable polymer backbone and a non-steroidal anti-inflammatory drug (NSAID) conjugated to the polymer backbone, wherein the polymer-NSAID conjugate is obtained by polymerising a NSAID-monomer conjugate of formula (IV):

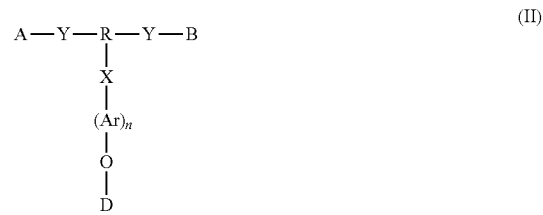

(IV)

where:
$Y^1$ and $Y^2$ each independently represent a reactive functional group, or $Y^1$ and $Y^2$ together form part of a cyclic group capable of ring-opening;

R comprises an optionally substituted aliphatic or an optionally substituted aryl;
X is a bond or a linking group;
Ar is an optionally substituted aryl;
D is the carboxylic acid residue of the ester formed with a substituted alkanoic acid NSAID; and
n is an integer selected from 0 and 1, with the proviso that when R comprises an optionally substituted aliphatic then n is 1, and when R comprises an optionally substituted aryl then n is 0 or 1;
with at least one monomer comprising compatible chemical functionality.

The present invention also provides a method for preparing a polymer-NSAID conjugate comprising as a part of its polymer backbone a moiety of formula (II):

$$A\text{—}Y\text{—}\underset{\underset{\underset{\underset{D}{|}}{\underset{O}{|}}}{\underset{(Ar)_n}{\underset{|}{X}}}}{R}\text{—}Y\text{—}B \qquad (II)$$

where:
A and B, which may be the same or different, each represent a biodegradable polymer backbone and are (i) attached to the —Y—R(X—(Ar)n-O-D)-Y— moiety as shown in formula (II) via a biodegradable moiety, and (ii) optionally, at least one of A and B comprises a hydrophilic group;
R comprises an optionally substituted hydrocarbon or an optionally substituted aryl;
Y at each occurrence is independently selected from the group consisting of —O—, —C(O)— and —$NR^a$—, where $R^a$ is H or $C_1$-$C_4$ alkyl;
X is a bond or a linking group;
Ar is an optionally substituted aryl;
D is the carboxylic acid residue of the ester formed with a substituted alkanoic acid NSAID; and
n is an integer selected from 0 and 1,
with the proviso that when R comprises an optionally substituted aliphatic then n is 1, and when R comprises an optionally substituted aryl then n is 0 or 1, said method comprising a step of polymerising a NSAID-monomer conjugate of formula (IV):

(IV)

where:
$Y^1$ and $Y^2$ each independently represent a reactive functional group, or $Y^1$ and $Y^2$ together form part of a cyclic group capable of ring-opening;
R comprises an optionally substituted aliphatic or an optionally substituted aryl;
X is a bond or a linking group;

Ar is an optionally substituted aryl;

D is the carboxylic acid residue of the ester formed with a substituted alkanoic acid NSAID; and n is an integer selected from 0 and 1, with the proviso that when R comprises an optionally substituted aliphatic then n is 1, and when R comprises an optionally substituted aryl then n is 0 or 1;

with at least one monomer comprising compatible chemical functionality.

A NSAID-monomer conjugate of general formula (IV) has been found to be particularly versatile and can advantageously be polymerised with one or more other monomers using techniques well known in the art.

Monomers that are polymerised with the NSAID-monomer conjugate of formula (IV) to form the polymer-NSAID conjugates of the invention will not only comprise compatible chemical functionality to react with the NSAID-monomer conjugate but that reaction will also afford or give rise to a biodegradable moiety.

Through the polymerisation of a NSAID-monomer conjugate of formula (IV), the process of the invention may advantageously be used to synthesise a polymer-NSAID conjugate with a high drug loading.

In some embodiments, the NSAID-monomer conjugate of formula (IV) is of formula (IVb):

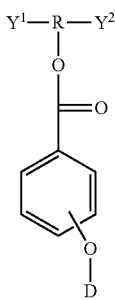

(IVb)

In other embodiments, the NSAID-monomer conjugate of formula (IV) is of formula (IVg):

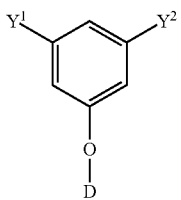

(IVg)

In some embodiments of a NSAID-monomer conjugate of formula (IV), (IVb) or (IVg), $Y^1$ and $Y^2$ are functional groups independently selected from the group consisting hydroxy, isocyanate, thiol, anhydride, carboxylic acid, carboxylic acid ester, carboxylic acid halide and amine. In some embodiments, $Y^1$ and $Y^2$ are each hydroxy.

NSAID-monomer conjugates may polymerise with at least one monomer comprising compatible chemical functionality selected from the group consisting of a polyisocyanate, a polyol, a polyacid, a polyester, a polyanhydride and a polyamine.

In some embodiments, the polymerisation of the NSAID-monomer conjugate with at least one monomer comprising compatible chemical functionality occurs in the presence of at least one co-monomer. In some specific embodiments, the co-monomer comprises at least one active-hydrogen group.

In some embodiments, the active-hydrogen group containing monomer is a macromonomer comprising a plurality of active-hydrogen groups. In such embodiments, the macromonomer may comprise a polymeric or oligomeric moiety selected from the group consisting of poly(ethylene glycol), poly(lactic acid-co-glycolic acid) (PLGA), poly(1,5-dioxepan-2-one) (PDOO), poly(glycerol acetate) (PGAc), poly(hydroxy butyrate), poly(glycerol phosphate), an amino acid polymer, or an amino acid oligomer, or a combination of, or a copolymer of, such polymeric or oligomeric moieties.

In another aspect, the present invention provides a water soluble polymer-NSAID conjugate as described herein.

In another aspect, the present invention provides a NSAID delivery system comprising a polymer-NSAID conjugate of the present invention.

In some embodiments the NSAID delivery system comprises a hydrophilic component. The hydrophilic component may be provided by at least one selected from the group consisting of (i) at least one hydrophilic group incorporated in the polymer-NSAID conjugate, and (ii) at least one hydrophilic molecule in admixture with the polymer-NSAID conjugate.

The hydrophilic molecule in admixture with the polymer-NSAID conjugate may be at least one selected from the group consisting of a hydrophilic low molecular weight compound, a hydrophilic oligomer and a hydrophilic polymer.

The hydrophilic molecule may be provided by or derived from at least one selected from the group consisting of low molecular weight diols (for example C2-C4 diols, such as ethylene glycol, propane diol, propylene glycol, butane diol etc), low molecular weight triols (for example glycerol, etc), low molecular weights polyols (for example sugar alcohols, such as mannitol, xylitol, sorbitol, etc), amino alcohols (for example ethanolamine, choline, etc), amino acids (lysine, glutamic acid etc), lactic acid, glycolic acid, hydroxy acids (for example, hydroxybutyric acid etc), 1,5-dioxepan-2-one, glycerol acetate, glycerol phosphate, or combinations thereof.

In some embodiments the NSAID delivery system comprises a hydrophilic polymer in admixture with the polymer-NSAID conjugate. The hydrophilic polymer may be selected from the group consisting of poly(ethylene glycol), poly(lactic acid-co-glycolic acid) (PLGA), poly(1,5-dioxepan-2-one) (PDOO), poly(glycerol acetate) (PGAc), poly(hydroxy butyrate), poly(glycerol phosphate) and an amino acid polymer, combinations thereof, and copolymers thereof.

The polymer-NSAID conjugates in accordance with the invention may be used in the treatment, alleviation or cure of a disease or disorder in a subject, or used to otherwise enhance the physical well-being of a subject.

The polymer-NSAID conjugates in accordance with the invention can therefore be prepared such that they are suitable for administration of the NSAID to a subject (i.e. suitable for in vivo applications).

The invention provides a method of delivering a NSAID to a subject, the method comprising administering to the subject a polymer-NSAID conjugate or a NSAID delivery system in accordance with the invention. In that case, the polymer-NSAID agent conjugate or NSAID delivery system will of course be suitable for administration to a subject.

In one aspect, the polymer-NSAID conjugates of the invention can advantageously be prepared with a relatively high loading of NSAID. This means that less material would be required in order to deliver a dose of the NSAID. The polymer-NSAID conjugates of the invention are well suited to be formed into medical devices that deliver a desired dose of the NSAID at a selected site.

A polymer-NSAID conjugate with a high NSAID loading may be particularly useful to deliver a dose of NSAID at a site within a subject that has a limited administration volume, for example the eye. This attribute, coupled with the activity of the NSAIDs, makes the conjugates particularly suited for use as an ocular implant to treat eye conditions.

A polymer-NSAID conjugate or NSAID delivery system of the invention can be delivered in the form of a gel or liquid or rapidly dissolve after administration to a load bearing joint to treat osteo-arthritis. A polymer-NSAID conjugate or NSAID delivery system of the invention can be delivered in one form and convert to another form soon after administration. For example, the NSAID delivery system of the invention could be administered as a liquid that then forms a gel (e.g. thermoset gel) once administered to a load bearing joint to treat osteo-arthritis.

A polymer-NSAID conjugate or NSAID delivery system of the invention can be incorporated into a topical product to treat inflammatory conditions. In one embodiment, the conjugate or NSAID delivery system is used to form NSAID-eluting fibres suitable for incorporation into topically applied wound dressings.

The polymer-NSAID conjugate in accordance with the invention may form part of, or be formed into, an article or device per se, or can be presented as a coating on a pre-formed article or device. The article or device is suitably a medical device.

The polymer-NSAID conjugate or NSAID delivery system may be included in an implant suitable to deliver a therapeutic dose of NSAID. The implant may be formed from the polymer-NSAID conjugate or from materials that contain the polymer-NSAID conjugate using techniques well known in the art. In one form of the invention, the implant is an ocular implant.

The present invention also provides an implant comprising a polymer-NSAID conjugate or a NSAID delivery system in accordance with the invention.

The present invention further provides a method of treating an eye condition in a subject, said method comprising administering to the eye of the subject a polymer-NSAID conjugate or a NSAID delivery system in accordance with the invention. In that case, the polymer-NSAID conjugate or NSAID delivery system will generally be provided in the form of an ocular implant.

The present invention further provides a method of treating osteo-arthritis in a subject, said method comprising administering to the affected joint of the subject a polymer-NSAID conjugate or a NSAID delivery system in accordance with the invention. In that case, the polymer-NSAID conjugate or NSAID delivery system will generally be provided in the form of an intra-articular implant. In another form of the invention the polymer-NSAID conjugate or NSAID delivery system may be included in a topical product. The topical product may be a topical covering suitable for application to the skin or mucous membrane of a subject. In embodiments of the invention, the topical covering is in the form of a wound dressing for application to a wound of a subject.

In some embodiments, the topical covering may be formed from the polymer-NSAID conjugate or the NSAID delivery system. In other embodiments, the polymer-NSAID conjugate is combined with other materials well known in the art for manufacturing topical coverings such as wound dressings. In yet other embodiments, the polymer-NSAID conjugate or NSAID delivery system may form, or be a part of, a coating on a pre-formed topical covering.

In some embodiments, the present invention provides a fibre comprising the polymer-NSAID conjugate in accordance with the invention. The fibre is suitably a NSAID-eluting fibre. Fibres comprising the polymer-NSAID conjugate can be incorporated into a topical product, such as a wound dressing.

In another form of the invention the polymer-NSAID conjugate or NSAID delivery system may formulated as a liquid. The polymer-NSAID conjugate or NSAID delivery system may be a liquid at room temperature or at physiological temperature (for example, approximately 37° C. for humans). The liquid may be in a form that is suitable for administration by injection to a desired site of treatment.

The present invention further provides a method of treating or alleviating an inflammatory condition in a subject which comprises the step of administering a polymer-NSAID conjugate or a NSAID delivery system in accordance with the invention to the subject.

In one form of the invention, the inflammatory condition is associated with a wound in a subject. In this instance, the method comprises topically applying a polymer-NSAID conjugate or a NSAID delivery system in accordance with the invention to the wound of the subject. The polymer-NSAID conjugate or NSAID delivery system will generally be provided in the form of a wound dressing.

In one form of the invention, the inflammatory condition is associated with a degenerative disorder. For example, the inflammatory condition may be associated with a degenerative joint disease, such as osteo-arthritis.

The present invention also provides a method for treating osteo-arthritis in a subject, the method comprising the step of administering a medicament comprising a polymer-NSAID conjugate or a NSAID delivery system as described herein to an intra-articular joint of the subject. In embodiments of the invention, the medicament is in an injectable form.

Accordingly, another aspect of the present invention provides use of a polymer-NSAID conjugate or a NSAID delivery system as described herein in the manufacture of a medicament for the treatment of osteo-arthritis in a subject. In embodiments of the invention, the medicament is in an injectable form.

The present invention also provides a method for treating osteo-arthritis in a subject, the method comprising the step of administering a medicament comprising a polymer-NSAID conjugate or a NSAID delivery system as described herein to an intra-articular joint of the subject. In embodiments of the invention, the medicament is in an injectable form.

Polymer-NSAID conjugates and NSAID delivery systems provide an effective and efficient means for delivering NSAIDs to a subject.

In another aspect, the invention provides a method of delivering a NSAID selected from the group consisting of diclofenac, ketorolac and indomethacin to a subject, the method comprising administering to the subject a polymer-NSAID conjugate or a NSAID delivery system in accordance with the invention. In one particular embodiment, the invention provides for delivery of diclofenac to a subject.

Further aspects of the invention appear below in the detailed description of the invention.

DETAILED DESCRIPTION OF THE INVENTION

The polymer-NSAID conjugates in accordance with the invention may be used in the alleviation, treatment, cure, or prevention of diseases or disorders in a subject, or used to otherwise enhance the physical well-being of a subject.

The polymer-NSAID conjugates in accordance with the invention can therefore be prepared such that they are suitable for administration to a subject (i.e. suitable for in vivo applications). By the term "subject" is meant either an animal or human subject. Generally, the subject will be a human subject.

The invention provides a method of delivering a drug, in particular, a non-steroidal anti-inflammatory drug (NSAID), to a subject, the method comprising administering to the subject a polymer-NSAID conjugate in accordance with the invention.

By "administration" of the polymer-NSAID conjugate to a subject is meant that the conjugate is transferred to the subject such that the drug will be released. Provided the drug can be released, there is no particular limitation on the mode of administration.

By "inflammatory condition" is meant a condition exhibiting an inflammatory response. Inflammatory responses can include one or more of following signs in the region of the affected body tissue: redness, swelling, heat, immobility, and pain.

Where the polymer-NSAID conjugate is to be used to treat an eye condition in a subject, administration will generally be by way of intracameral, intravitreal, episcleral, subconjunctival or topical administration. By "eye condition" is meant inflammation and/or pain of the eye.

Where the polymer-NSAID conjugate is to be used to treat an inflammatory condition of the body, administration may be by way of topical application. An inflammatory condition may be acute or chronic inflammation.

The inflammatory condition may be associated with a wound in a subject. Where the inflammatory condition is associated with a wound in a subject, administration will generally be by way of topical application. By "wound" is meant a physical injury to the body. The wound may be an acute, sub-acute or chronic wound. In some instances, the injury may be the result of a laceration or other injury that breaks the skin or mucous membrane, or causes an opening to be made in the skin or mucous membrane of the body. In other instances, the injury may not result in a breakage of the skin or mucous membrane. Thus the present invention contemplates topical application of the polymer-NSAID conjugates to wounds or inflammatory conditions in which the surface of the skin or mucous membrane can be either broken or intact.

The inflammatory condition may be associated with a degenerative joint disease, such as osteo-arthritis. Where the inflammatory condition is associated with a degenerative joint disease in a subject, administration will generally be by way of intra-articular administration.

The polymer-NSAID conjugates may be provided in particulate form and blended with a pharmacologically acceptable carrier to facilitate administration. By "pharmacologically acceptable" is meant that the carrier is suitable for administration to a subject in its own right. In other words, administration of the carrier to a subject will not result in unacceptable toxicity, including allergenic responses and disease states. The term "carrier" refers to the vehicle with which the conjugate is contained prior to being administered.

As a guide only, a person skilled in the art may consider "pharmacologically acceptable" as an entity approved by a regulatory agency of a federal or state government or listed in the US Pharmacopeia or other generally recognised pharmacopeia for use in animals, and more particularly humans.

Suitable pharmacologically acceptable carriers are described in Martin, Remington's Pharmaceutical Sciences, 18th Ed., Mack Publishing Co., Easton, Pa., (1990).

The conjugate may also form part of or be formed into an article or device, or be applied as a coating on an article or device, such as a medical device. By "medical device" is meant any article or device intended for use in the alleviation, treatment or prevention of a disease or disorder in a subject.

The article or device having the conjugate as a component thereof may be implanted in a subject. By being "implanted" is meant that the article or device is totally or partly introduced medically into a subject's body, or by medical intervention into a natural orifice of a subject, and which is intended to remain there after the procedure. Where the article or device is to be implanted, it can conveniently be referred to as an "implant". An implant may be in solid or liquid form.

The article or device having the conjugate as a component thereof may be topically applied to a subject. By being "topically applied" is meant application to a body surface, such as the surface of the skin or mucosal membrane of a subject.

In one aspect the invention provides a medical device comprising a polymer-NSAID conjugate in accordance with the invention.

In one embodiment, the medical device is an implant. Where the implant is to be administered to the eye, it may be conveniently referred to as an "ocular implant". In that case, the ocular implant will generally be administered to a subject intracamerally, intravitreally, episclerally, subconjunctivally or topically. Where the implant is to be administered to a joint, it may be conveniently referred to as an "intra-articular implant". In that case, the intra-articular implant will generally be administered to a subject intra-articularly. Ocular implants or intra-articular implants can be administered as solids or as liquids, and be capable of rapidly dissolving in, be miscible with, or form a gel like state within the physiological medium.

In another embodiment, the medical device is a topical product, such as a topical covering. Where the topical covering is to be administered to a wound for the treatment or alleviation of the wound, it may be conveniently referred to as a "wound dressing". In that case, the wound dressing will generally be topically applied to a subject.

Articles or devices may be fabricated in a manner that enables the polymer-NSAID conjugates of the invention to be administered in a single dose or a series of doses.

The present invention relates to a polymer-NSAID conjugate comprising a polymer backbone and a non-steroidal anti-inflammatory drug (NSAID) conjugated to the polymer backbone.

The present invention also relates to monomer-NSAID conjugates comprising a non-steroidal anti-inflammatory drug (NSAID) conjugated to the monomer.

As used herein the term "conjugate" refers to the product formed through covalent bonding between the monomer or polymer and the NSAID. Accordingly, the term "conjugated" refers to the state of the product that is formed through covalent bonding between the monomer or polymer and the NSAID. In accordance with the invention, a NSAID conjugated to a polymer backbone is pendant from the polymer backbone. The pendant NSAID can be released by the breakdown of covalent bonds through hydrolysis and the degradation of the linkages attaching the NSAID to the polymer backbone.

Generally, NSAIDs are an important therapeutic class of drugs typically used to suppress pain and inflammation. Drugs belonging to this class typically possess one or more of the following four major activities: analgesic (provide relief of pain by a mechanism other than reduction of inflammation), antipyretic (ability to lower elevated body temperature), anti-inflammatory (ability to reduce inflammation), and uricosuric (ability to promote excretion of uric acid, e.g., for treating gout) activities.

NSAIDs can be classified according to their chemical structure. One important class of NSAIDs are substituted alkanoic acid NSAIDs. Members in this class of NSAIDs can include acetic acid derivatives such as indole acetic acid derivatives and pyrrole acetic acid derivatives, and propionic acid derivatives.

For example, diclofenac is a non-steroidal anti-inflammatory drug (NSAID) having a chemical structure as illustrated below:

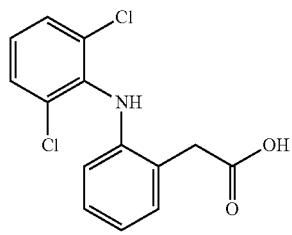 [SMILES: O=C(O)Cc1ccccc1Nc1c(Cl)cccc1Cl]

Diclofenac has anti-inflammatory, analgesic and antipyretic properties. In conventional treatments diclofenac is used for the treatment of musculoskeletal complaints and for pain management, and is often formulated in topical gels, lotions and patches, oral formulations and injectable forms for such use. For example, diclofenac can been used to treat ocular discomfort, inflammation and swelling following eye surgery, and is typically administered in eye drops for such treatment. It can also be used to treat joint inflammation and swelling associated with osteo-arthritis, and is typically administered as a topical gel or oral tablet for such treatment.

For example, ketorolac is a non-steroidal anti-inflammatory drug (NSAID) having a chemical structure as illustrated below:

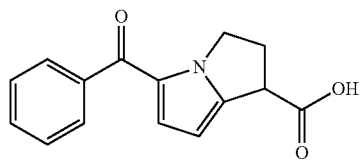 [SMILES: O=C(c1ccccc1)c1ccc2n1CCC2C(=O)O]

Ketorolac has anti-inflammatory, analgesic and antipyretic properties. In conventional treatments ketorolac is used for management of pain and inflammation, and is often formulated in topical gels, lotions and patches, eye drops, oral formulations and injectable forms for such use. For example, ketorolac can been used to treat ocular discomfort, inflammation and swelling following eye surgery, and is typically administered in eye drops for such treatment. It can also be used to treat joint inflammation and swelling associated with osteo-arthritis, and is typically administered as an intra-articular injection for such treatment.

For example, indomethacin is a non-steroidal anti-inflammatory drug (NSAID) having a chemical structure as illustrated below:

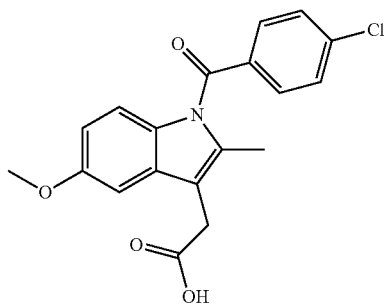 [SMILES: COc1ccc2c(c1)c(CC(=O)O)c(C)n2C(=O)c1ccc(Cl)cc1]

Indomethacin has anti-inflammatory, analgesic and antipyretic properties. In conventional treatments indomethacin is used for the management of pain and inflammation, and is often formulated in topical creams and patches, eye lotions, oral formulations and injectable forms for such use. For example, indomethacin can been used to treat discomfort, inflammation and swelling associated with gout, and is typically administered orally as capsules for such treatment.

In one aspect, the present invention relates to a polymer-NSAID conjugate comprising a biodegradable polymer backbone and a non-steroidal anti-inflammatory drug (NSAID) conjugated pendant to the polymer backbone via an aryl ester group.

In one aspect, the present invention provides a polymer-NSAID conjugate comprising a biodegradable polymer backbone and a non-steroidal anti-inflammatory drug (NSAID) conjugated to the polymer backbone, wherein the conjugate comprises as a part of its polymer backbone an ester linked moiety of formula (I):

where:
R comprises an optionally substituted aliphatic or an optionally substituted aryl;
X is a bond or a linking group;
Ar is an optionally substituted aryl;
D is the carboxylic acid residue of the ester formed with a substituted alkanoic acid NSAID; and
n is an integer selected from 0 and 1,
with the proviso that when R comprises an optionally substituted aliphatic then n is 1, and when R comprises an optionally substituted aryl then n is 0 or 1.

As used herein the expression forming "part of the polymer backbone" means that the moiety of formula (I) is part of the string of atoms that are each connected so as to form the polymer chain. In other words, the moiety per se of formula (I) is not pendant from the polymer backbone.

Having said this, it will be appreciated that groups X, (Ar)$_n$, O and D in the moiety of formula (I) will be pendant from the polymer backbone.

Substituted alkanoic acid NSAIDs generally contain a free carboxylic acid functional group. The free carboxylic acid functional group can serve as a reactive functional group for conjugation of the drug to a polymer. In conjugating the drug to the polymer backbone, the substituted alkanoic acid NSAID is covalently linked to the polymer via the carboxylic acid group. The drug moiety (denoted D in formulae described herein) linked to the polymer is therefore a carboxylic acid residue of the conjugated NSAID.

Substituted alkanoic acid NSAIDs can also contain other functional groups in addition to a free carboxylic acid functional group. For example, diclofenac also has a secondary amine group and in principle, the drug could be conjugated to the polymer via this amine group. However, conjugation through functional groups other than a carboxylic acid functional group is generally not preferred. For example, conjugation through the amine group of diclofenac would likely result in significant in-chain incorporation of the drug, which in turn would provide inefficient or no release of the drug.

Substituted alkanoic acid NSAIDs may also contain two or more free carboxylic acid functional groups. For example, olsalazine and balzalazide each contain two free carboxylic acid groups. When two or more free carboxylic acid functional groups are present in a substituted alkanoic acid NSAID, conjugation of the drug may occur though any one of the carboxylic acid groups. However, other factors, such as steric or electronic factors around the site of conjugation to the monomer or polymer, might influence the selection of carboxylic acid functional group for drug conjugation.

The substituted alkanoic acid NSAID (also referred to herein as "the drug") is conjugated pendant to the polymer backbone. That is, the conjugated drug does not form part of the polymer backbone chain. The pendant configuration ensures efficient release of the drug. Furthermore, by being pendant, the drug can be released without causing a reduction in the chain length of the polymer backbone.

The polymer-NSAID conjugate may have a single moiety of formula (I), but more typically the conjugate will comprise a plurality of moieties of formula (I). In polymer-NSAID conjugates comprising a plurality of moieties of formula (I), each group represented by R, X, Ar, D and n may be independently selected at each occurrence, with the proviso that D at each occurrence is linked to the polymer backbone by an aryl ester group.

Polymer-NSAID conjugates of the present invention comprise a substituted alkanoic acid NSAID conjugated to a biodegradable polymer backbone via an aryl ester group. In accordance with the invention, the drug is covalently linked via a carboxylic acid group present on the drug to an oxygen-containing substituent present on an aryl group associated with the polymer backbone. The linkage of the drug moiety (denoted "D") to the oxygen atom (denoted "O") on the aryl group associated with the polymer backbone therefore provides an ester linkage (ester bond) between D and the aryl group.

An important feature of the invention is the use of an aryl ester linkage to conjugate the substituted alkanoic acid NSAID. As discussed further below, such linkages have been found to provide more effective drug release than other linkage strategies that have been used in the prior art to conjugate drug compounds. For example, in one set of embodiments it has been found that the aryl ester linkage can provide for delayed drug release. Delayed drug release allows the product to be administered at some time prior to the need for therapy (for example as a prelude to surgical intervention). In another set of embodiments, it has been found that the aryl ester linkage can provide for drug release with a zero order release profile starting immediately after administration. One advantage of the invention is that zero order release of the drug can be sustained occur over a period of time, such as over a period of at least 5 days, at least 10 days, at least 14 days, at least 30 days, at least 60 days or at least 90 days. In some embodiments, zero order release of the drug can be sustained so as to occur over at least 60 days.

The aryl ester linkage may be more labile than other ester moieties present in the polymer-NSAID conjugate, such as for example, ester moieties that may form part of the molecular structure of the polymer backbone. As a result, drug release of the polymer-NSAID conjugate as a result of cleavage or hydrolysis of the aryl ester linkage preferably occurs at a faster rate than the rate of biodegradation of ester moieties in the polymer backbone.

The moiety "R" present in formula (I) described herein comprises an optionally substituted aliphatic or an optionally substituted aryl.

In some embodiments of formula (I), R comprises an optionally substituted aliphatic. Thus in some embodiments, the present invention provides a polymer-NSAID conjugate comprising a biodegradable polymer backbone and a non-steroidal anti-inflammatory drug (NSAID) conjugated to the polymer backbone, wherein the conjugate comprises as a part of its polymer backbone an ester linked moiety of formula (Ia):

where:
R$^1$ comprises an optionally substituted aliphatic;
X is a bond or a linking group;
Ar is an optionally substituted aryl;
D is the carboxylic acid residue of the ester formed with a substituted alkanoic acid NSAID; and
n is 1.

As used herein, the term "aliphatic", used either alone or in compound words denotes partially or completely saturated linear or branched hydrocarbyl and non-aromatic cyclic hydrocarbyl (including non-aromatic carbocyclic aliphatic and non-aromatic heterocyclic aliphatic). Examples of aliphatic groups include alkanes, alkenes, alkynes and cycloalkanes. The aliphatic moiety may be optionally substituted by one or more optional substituents as described herein.

In some embodiments of formula (Ia), R$^1$ comprises an optionally substituted aliphatic of between 1 and 12 carbon atoms. In more specific examples of formula (Ia), R$^1$ comprises an optionally substituted aliphatic of between 1 and 10 carbon atoms, or between 2 and 6 carbon atoms.

In some embodiments of formula (Ia), R$^1$ is an optionally substituted linear or branched hydrocarbyl of between 1 and 12 carbon atoms, between 1 and 10 carbon atoms, between 2 and 6 carbon atoms, or from 2 to 3 carbon atoms.

In some embodiments of formula (Ia), $R^1$ may be optionally substituted non-aromatic cyclic hydrocarbyl containing between 4 to 12 ring members. In more specific examples, $R^1$ may be optionally substituted non-aromatic cyclic hydrocarbyl containing between 5 to 8 ring members, or 5 to 6 ring members.

As used herein, the term "ring members" denotes the atoms forming part of a ring system. In a non-aromatic cyclic hydrocarbyl, the ring atoms may each be carbon atoms, to form a carbocyclic aliphatic group.

In some embodiments, one or more of the carbon atoms of the aliphatic moiety (e.g. a linear or branched hydrocarbyl or cyclic hydrocarbyl) may be optionally replaced by a heteroatom. From 1 to 3 heteroatoms may be present in the aliphatic moiety. When present, the heteroatoms may be selected from O, N, S, P and Se, particularly O, N and S, and may, in the case of nitrogen (N), be substituted by hydrogen or alkyl such as $C_{1-4}$ alkyl. In the case of a non-aromatic heterocyclic hydrocarbyl group, one or more of the ring atoms are heteroatoms. When two or more heteroatoms are present, the heteroatoms may be the same or different at each occurrence.

Some specific examples of $R^1$ are illustrated below:

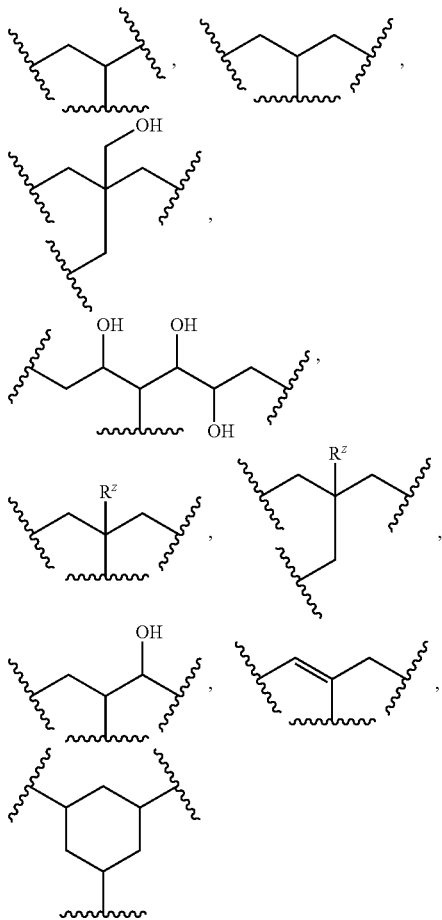

where $R^z$ is $C_{1-6}$alkyl, preferably methyl or ethyl.

As discussed further below, in formula (Ia), the aryl ester group is represented by the group Ar—O-D.

In some embodiments of formula (I), R comprises an optionally substituted aryl. Thus in some embodiments, the present invention provides a polymer-NSAID conjugate comprising a biodegradable polymer backbone and a non-steroidal anti-inflammatory drug (NSAID) conjugated to the polymer backbone, wherein the conjugate comprises as a part of its polymer backbone an ester linked moiety of formula (Ib):

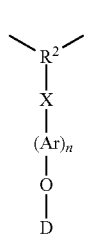

(Ib)

where:
$R^2$ comprises an optionally substituted aryl;
X is a bond or a linking group;
Ar is an optionally substituted aryl;
D is the carboxylic acid residue of the ester formed with a substituted alkanoic acid NSAID; and
n is an integer selected from 0 and 1,
with the proviso that when n is 0 then X is a bond.

In some embodiments of a moiety of formula (Ib), n is 0. In such embodiments X is preferably a bond such that the group —O-D is directly attached to $R^2$ as illustrated in formula (Ic):

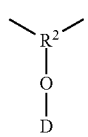

(Ic)

where $R^2$ and D are as defined in formula (Ib).

As discussed further below, in formula (Ic), the group $R^2$—O-D represents an aryl ester group.

In other embodiments of a moiety of formula (Ib), n is 1. In such embodiments the group —O-D is attached to Ar as illustrated in formula (Id):

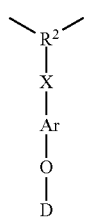

(Id)

where $R^2$, X, Ar and D are as defined in formula (Ib).

In formula (Id), the group Ar—O-D represents an aryl ester group.

In formulae (Ib), (Ic) and (Id), $R^2$ comprises an optionally substituted aryl.

The term "aryl" used either alone or in compound words denotes a carbocyclic aromatic (carbocyclic aryl) or heterocyclic aromatic (heterocyclic aryl) ring system. The aryl may be optionally substituted by one or more optional substituents as described herein.

The aryl may comprise a suitable number of ring members. In some embodiments, the aryl comprises from 5 to 12 ring members, from 5 to 10 ring members, or from 5 to 6 ring members. In a carbocyclic aryl group, the ring members are each carbon atoms. In a heterocyclic aryl group from one to three of the ring members are heteroatoms. The heteroatoms may be selected from the group consisting of O, N, S, P and Se, particularly O, N and S. When two or more heteroatoms are present, the heteroatoms may be the same or different at each occurrence.

Suitable carbocyclic aryl may be selected from the group consisting of phenyl, biphenyl, naphthyl, tetrahydronaphthyl, idenyl, azulenyl, and the like.

Suitable heterocyclic aryl may be selected from the group consisting of furanyl, thiophenyl, 2H-pyrrolyl, pyrrolinyl, oxazolinyl, thiazolinyl, indolinyl, imidazolidinyl, imidazolinyl, pyrazolyl, pyrazolinyl, isoxazolidinyl, isothiazolinyl, oxadiazolinyl, triazolinyl, thiadiazolinyl, tetrazolinyl, pyridinyl, pyridazinyl, pyrimidinyl, pyrazinyl, triazenyl, indolyl, isoindolinyl, benzimidazolyl, benzoxazolyl, quinolinyl, isoquinolinyl, and the like.

In some embodiments, $R^2$ comprises an optionally substituted $C_5$-$C_{12}$ aryl moiety. In some embodiments $R^2$ comprises an optionally substituted phenyl ($C_6$ carbocyclic aryl) or an optionally substituted pyridinyl ($C_6$ heterocyclic aryl).

In some specific examples, $R^2$ comprises an aryl moiety having any one of the following structures:

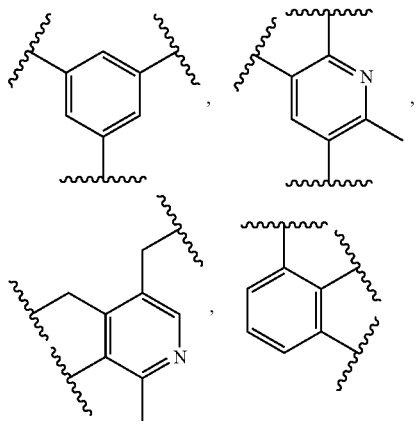

In formula (Ic), the group $R^2$—O-D represents an aryl ester group. In such embodiments, the drug is conjugated via a carboxylic acid functional group to an oxygen atom-containing substituent on the aryl represented by $R^2$. The linkage of the carboxylic acid group on the drug moiety (denoted "D") to the oxygen atom (denoted "O") of the substituent provides an ester linkage (ester bond) between D and $R^2$. The group $R^2$—O-D in formulae described herein is therefore an ester linked group, with $R^2$ forming the aryl portion of the aryl ester group.

Some specific examples of a moiety of formula (Ic) include the following:

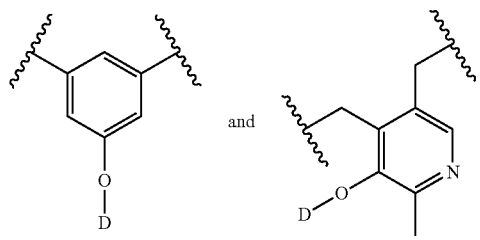

where ⌇ represents where the moiety of formula (Ic) is attached to the remainder of the polymer backbone.

In embodiments of the invention where n is 1, such as in formulae (Ia) and (Id), the group Ar—O-D represents an aryl ester group. In such embodiments, the drug is conjugated via a carboxylic acid functional group to the group Ar—O. The drug is covalently linked to the oxygen atom (denoted "O") of the group Ar—O. The linkage of the drug moiety (denoted "D") to the oxygen atom therefore provides an ester linkage (ester bond) between the groups D and Ar. The group —Ar—O-D in formulae described herein is therefore an ester linked group, with Ar forming the aryl portion of the aryl ester group.

The group "Ar" in formulae described herein represents an optionally substituted aryl group. The optionally substituted aryl may be selected from any one of the groups defined herein. Ar may be a carbocyclic aromatic (carbocyclic aryl) or a heterocyclic aromatic (heterocyclic aryl) ring system. The aryl may be optionally substituted by one or more optional substituents as described herein.

In some embodiments, Ar comprises from 5 to 12 ring members, from 5 to 10 ring members, or from 5 to 6 ring members. The ring members may each be carbon atoms (as in the case of a carbocyclic aryl), or from one to three of the ring members may be heteroatoms (as in the case of heterocyclic aryl) selected from the group consisting of O, N, S, P and Se, particularly O, N and S.

In some embodiments, Ar may be a carbocyclic aryl selected from the group consisting of phenyl, biphenyl, naphthyl, tetrahydronaphthyl, idenyl, azulenyl, and the like.

In some embodiments, Ar may be a heterocyclic aryl selected from the group consisting of furanyl, thiophenyl, 2H-pyrrolyl, pyrrolinyl, oxazolinyl, thiazolinyl, indolinyl, imidazolidinyl, imidazolinyl, pyrazolyl, pyrazolinyl, isoxazolidinyl, isothiazolinyl, oxadiazolinyl, triazolinyl, thiadiazolinyl, tetrazolinyl, pyridinyl, pyridazinyl, pyrimidinyl, pyrazinyl, triazenyl, indolyl, isoindolinyl, benzimidazolyl, benzoxazolyl, quinolinyl, isoquinolinyl, and the like.

In some embodiments of the invention, Ar is an optionally substituted $C_5$-$C_{12}$ aryl. In some embodiments Ar is optionally substituted phenyl ($C_6$ carbocyclic aryl). In some embodiments of polymer-NSAID conjugates of the invention, the group —Ar—O-D is covalently linked to the polymer backbone of the conjugate via moiety "X". The moiety X may be a bond or an optionally substituted linking group.

When n is 0, such as in formula (Ic), X is preferably a bond.

When n is 1, such as in formulae (Ia) and (Id), X may be a bond or an optionally substituted linking group. In some embodiments when n is 1, X is preferably an optionally substituted linking group. In formulae described herein, when X is a bond, it is suitably a single covalent bond. In formulae described herein, when X is an optionally substituted linking group it is suitably a divalent substituent group.

Accordingly, the linking group represented by X may couple the group Ar to a polymer backbone or to a monomer as described herein. In polymer-NSAID conjugates, the use of the linking group can provide facile coupling of the ester linked drug to the polymer backbone. It may provide the skilled worker with the ability to couple the ester linked drug at a sterically hindered position that could not otherwise be achieved by direct coupling to the polymer backbone.

The choice of linking group will determine the spacing of the group —Ar—O-D from the polymer backbone of the polymer-NSAID conjugates of the invention. In this respect, the use of a linking group can provide a means to distance D from the polymer backbone and can help to reduce steric crowding around the backbone.

Examples of suitable linking groups (X) include the divalent form of a group selected from oxy (—O—), alkyl, alkenyl, alkynyl, aryl, acyl (including —C(O)—), carbocyclyl, heterocyclyl, heteroaryl, alkyloxy, alkenyloxy, alkynyloxy, aryloxy, acyloxy, carbocyclyloxy, heterocyclyloxy, heteroaryloxy, poly(alkyleneoxy), alkylthio, alkenylthio, alkynylthio, arylthio, acylthio, carbocyclylthio, heterocyclylthio, heteroarylthio, alkylalkenyl, alkylalkynyl, alkylaryl, alkylacyl, alkylcarbocyclyl, alkylheterocyclyl, alkylheteroaryl, alkyloxyalkyl, alkenyloxyalkyl, alkynyloxyalkyl, aryloxyalkyl, alkylacyloxy, alkyloxyacylalkyl, alkylcarbocyclyloxy, alkylheterocyclyloxy, alkylheteroaryloxy, alkylthioalkyl, alkenylthioalkyl, alkynylthioalkyl, arylthioalkyl, alkylacylthio, alkylcarbocyclylthio, alkylheterocyclylthio, alkylheteroarylthio, alkylalkenylalkyl, alkylalkynylalkyl, alkylarylalkyl, alkylacylalkyl, arylalkylaryl, arylalkenylaryl, arylalkynylaryl, arylacylaryl, arylacyl, arylcarbocyclyl, arylheterocyclyl, arylheteroaryl, alkenyloxyaryl, alkynyloxyaryl, aryloxyaryl, arylacyloxy, arylcarbocyclyloxy, arylheterocyclyloxy, arylheteroaryloxy, alkylthioaryl, alkenylthioaryl, alkynylthioaryl, arylthioaryl, arylacylthio, arylcarbocyclylthio, arylheterocyclylthio, and arylheteroarylthio, wherein where present at least one —CH$_2$— group in any alkyl chain may be replaced by a divalent group independently selected from —O—, —OP(O)$_2$—, —OP(O)$_2$O— —S—, —S(O)—, —S(O)$_2$O—, —OS(O)$_2$O—, —N=N—, —OSi(OR$^a$)$_2$O—, —Si(OR$^a$)$_2$O—, —OB(OR$^a$)O—, —B(OR$^a$)O—, —NR$^a$—, —C(O)—, —C(O)O—, —OC(O)O—, —OC(O)NR$^a$— and —C(O)NR$^a$—, where the or each R$^a$ may be independently selected from hydrogen, alkyl, alkenyl, alkynyl, aryl, carbocyclyl, heteroaryl, heterocyclyl, arylalkyl, and acyl. The or each R$^a$ may also be independently selected from hydrogen, $C_{1-18}$alkyl, $C_{1-18}$alkenyl, $C_{1-18}$alkynyl, $C_{6-18}$aryl, $C_{3-18}$carbocyclyl, $C_{3-18}$heteroaryl, $C_{3-18}$heterocyclyl, and $C_{7-18}$arylalkyl. Such linking groups may be optionally substituted with one or more optional substituents as described herein.

In some embodiments X is an optionally substituted branched linking group. Where the linking group is branched, two or more —Ar—O-D groups may be attached to the polymer backbone via X.

In some embodiments, X is an optionally substituted linking group comprising a functional group selected from the group consisting of —O—, —C(O)O—, —OC(O)—, —C(O)—, —OC(O)NH—, —NHC(O)O—, —OC$_6$H$_4$O—, —OC(O)[CH$_2$]$_n$— where n=1 to 5, —C(O)NR$^a$— and —NR$^a$C(O)—, where R$^a$ is H or $C_1$-$C_4$ alkyl.

Some specific examples of suitable linking groups include: —O—; —C(O)—; —OC(O)NH—, —NHC(O)O—; —NR$^a$C(O)—; —C(O)NR$^a$—; and optionally substituted: —OC(O)—R$^3$—C(O)—; —C(O)O—R$^3$—C(O)—; —NR$^a$C(O)O—R$^3$—C(O)—; —OC(O)NR$^a$—R$^1$—C(O)—; —NR$^a$C(O)—R$^3$—C(O)—; —C(O)NR$^a$—R$^3$—C(O)—; —C(O)O—R$^3$—O—; —OC(O)—R$^3$—O—; —O—R$^3$—O—; —O—R$^3$—NR$^a$—; —OC(O)—R$^3$—NR$^a$—; —C(O)—R$^3$—NR$^a$—; —OC(O)—R$^3$—; —C(O)O—R$^3$—; —C(O)—R$^3$—O—; and —C(O)NR$^a$—R$^3$—NR$^a$— where R$^3$ represents an optionally substituted hydrocarbon and R$^a$ is H or $C_1$-$C_4$ alkyl.

More specific examples of suitable linking groups include: —C(O)—; —C(O)O—R$^3$—O—; —O—R$^3$—O—; —OC(O)—R$^3$—O—; and —C(O)—R$^3$—O—, where R$^3$ represents an optionally substituted hydrocarbon.

In some embodiments R$^3$ may comprise between 1 and 12 carbon atoms, for example between 1 and 10 carbon atoms, between 1 and 6 carbon atoms, or 2 or 3 carbon atoms. In one embodiment, R$^3$ is an optionally substituted linear or branched aliphatic hydrocarbon. In another embodiment, R$^3$ is an optionally substituted aryl.

In some embodiments of a polymer-NSAID conjugate of the invention, the group —X—Ar—O— is selected from the group consisting of —C(O)—$C_{5-12}$aryl-O— (such as —C(O)—$C_{5-6}$aryl-O—); —C(O)NR$^a$—$C_{5-12}$aryl-O— (such as —C(O)NR$^a$—$C_{5-6}$aryl-O—); —OC(O)—$C_{5-12}$aryl-O— (such as —OC(O)—$C_{5-6}$aryl-O—); and C(O)O—$C_{5-12}$aryl-O— (such as —C(O)O—$C_{5-6}$aryl-O—). More preferred is —C(O)—$C_6$aryl-O—.

In one embodiment of a polymer-NSAID conjugate of the invention, the moiety of formula (I) is a moiety of formula (Ie):

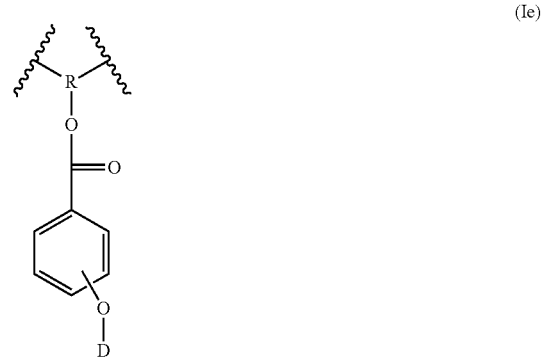

(Ie)

where ⁓ represents where the moiety of formula (Ie) is attached to the remainder of the polymer backbone; and R and D are as defined herein in formula (I).

In the moiety of formula (Ie), the ester linked drug moiety (denoted —O-D) may be substituted at the ortho-, meta- or para-position of the aryl ring, relative to the —OC(O)— group linking the aryl to the polymer backbone. In some embodiments the ester linked drug moiety (denoted —O-D) is be substituted at the ortho- or para-position of the aryl ring, relative to the —OC(O)— group linking the aryl to the polymer backbone. In specific embodiments of the invention, the ester linked drug is substituted at the para position, as shown in formula (If):

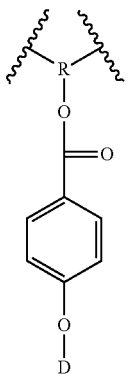

(If)

The polymer-NSAID conjugates of the present invention comprise a biodegradable polymer backbone. The moieties of formulae (I), (Ia), (Ib), (Ic), (Id), (Ie) or (If) as described herein form part of the biodegradable polymer backbone structure.

The term "biodegradable polymer backbone" as used herein refers to a polymer backbone that includes moieties that are "biodegradable". By being biodegradable, the moieties are susceptible to break down (i.e. a reduction in molecular weight) by chemical or enzymatic decomposition in a biological environment (e.g. within a subject or in contact with biological material such as blood, tissue etc), as opposed to physical degradation. Such decomposition will typically be via the hydrolysis of labile moieties that form part of the molecular structure of the polymer backbone. In other words, the polymer backbone will comprise moieties that are susceptible to hydrolytic cleavage. The rate of hydrolysis of the biodegradable moieties may vary over time, or be activated by any number of extrinsic or intrinsic factors (e.g. light, heat, radiation, pH, enzymatic or non-enzymatic cleavage, etc.). By including biodegradable moieties, the conjugates in accordance with the invention can advantageously be used to release the drug "D", for example within a subject, without the need to subsequently remove the remaining conjugate structure from the subject.

Reference herein to biological material such as "biological tissue" is intended to include cells or tissue in vivo (e.g. cells or tissue of a subject) and in vitro (e.g. cultured cells).

It is a requirement of the invention that at least a portion or part of the polymer backbone is biodegradable. In some embodiments, the entire polymer backbone is biodegradable. Biodegradable polymer backbones may be provided through the incorporation of one or more biodegradable polymers in the backbone.

The biodegradable polymer backbones may comprise a polymer selected from the group consisting of polyester polymers, polyanhydride polymers, polycarbonate polymers, polyamide polymers, polyimide polymers, polyurethane polymers, polyurea polymers, polysaccharides, polypeptides, copolymers thereof, and combinations thereof.

The biodegradable polymer backbone may comprise a homopolymer, a copolymer, or a combination of any of the above polymers.

In some embodiments, the biodegradable polymer backbone may comprise at least one further polymer, for example, a hydrophilic polymer, in addition to the biodegradable polymer. In such embodiments, the polymer backbone may comprise a biodegradable segment and a hydrophilic segment. The further polymer (e.g. hydrophilic polymer) may or may not be biodegradable. It is requirement of the invention that at least a portion of the polymer backbone is composed of biodegradable polymer.

In some embodiments, the entire polymer backbone is biodegradable. In such embodiments, the polymer backbone is composed entirely of biodegradable polymer.

In embodiments of a polymer-NSAID conjugate of the invention, the conjugate comprises as a part of its polymer backbone a moiety of formula (II):

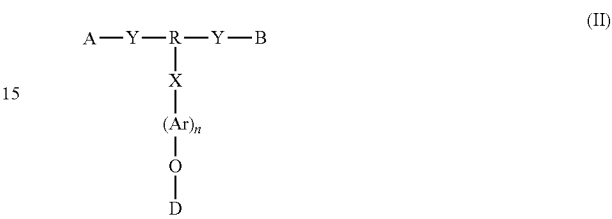

(II)

where:
A and B, which may be the same or different, each represent a biodegradable polymer backbone and are (i) attached to the —Y—R(X—(Ar)$_n$—O-D)-Y— moiety as shown in formula (II) via a biodegradable moiety, and (ii) optionally, at least one of A and B comprises a hydrophilic group;
R comprises an optionally substituted aliphatic or an optionally substituted aryl;
Y at each occurrence is independently selected from the group consisting of —O—, —C(O)— and —NR$^a$—, where R$^a$ is H or $C_1$-$C_4$ alkyl;
X is a bond or a linking group;
Ar is optionally substituted aryl;
D is the carboxylic acid residue of the ester formed with a substituted alkanoic acid NSAID; and
n is an integer selected from 0 and 1,
with the proviso that when R comprises an optionally substituted aliphatic then n is 1, and when R comprises an optionally substituted aryl then n is 0 or 1.

The moieties R, X, Ar and D in formula (II) may be selected from any of the moieties described herein.

The moiety "Y" present in formulae (II) described herein connects R to the polymer backbone represented by A and B and is attached to A and B via a biodegradable moiety.

As used herein the expression "biodegradable moiety" is intended to mean a moiety that can undergo chemical or enzymatic decomposition under physiological conditions or in a biological environment. Such chemical or enzymatic decomposition will typically be via hydrolysis. In other words, the biodegradable moiety with be susceptible to hydrolytic cleavage.

Those skilled in the art will appreciate the type of moieties that are typically susceptible to hydrolytic cleavage under physiological conditions or in a biological environment. Such moieties may include amide, urethane (carbamate), ester, anhydride, urea and carbonate. In one embodiment, Y may be attached to A and B via a biodegradable moiety selected from the group consisting of an ester moiety and a urethane moiety.

The terms "carbamate" and "urethane" referred to herein are used interchangeably. A person skilled in the art would understand that the terms "carbamate" and "urethane" each refer to a —NC(=O)O— moiety.

In the moiety of formula (II), Y is at each occurrence is independently selected from the group consisting of —O—, —C(O)— and —NR$^a$— (where R$^a$ is H or C$_1$-C$_4$ alkyl) at each occurrence. In some specific embodiments, Y at each occurrence is O.

In accordance with the invention, A and B, which may be the same or different, each represent a biodegradable polymer backbone and are "attached to the —Y—R(X—(Ar)n-O-D)-Y— moiety as shown in formula (II) via a biodegradable moiety". By this is meant that the atoms represented by Y in the —Y—R(X—(Ar)n-O-D)-Y— moiety each form part of a biodegradable moiety. For example, the Y in the —Y—R(X—(Ar)n-O-D)-Y moiety may each independently form part of an ester or urethane moiety as illustrated below when Y is O:

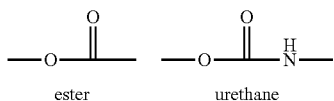

ester    urethane

In one embodiment, the atoms represented by Y in the —Y—R(X—(Ar)n-O-D)-Y— each independently form part of an ester or urethane moiety.

A skilled person would understand that Y at each occurrence can also form part of an ester or urethane moiety when Y represents —C(O)— or NR$^a$ (where R$^a$ is hydrogen or C1 to C6 alkyl), respectively.

In some embodiments of formula (II), n is 1 and Y at each occurrence is 0. In such embodiments, the moiety of formula (II) has a structure of (IIa):

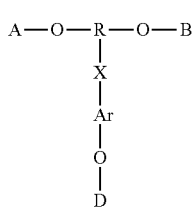

where R in formula (IIa) is selected from the group consisting of an optionally substituted aliphatic and an optionally substituted aryl, as described herein.

In specific embodiments, the moiety of formula (IIa) has a structure of formula (IIb):

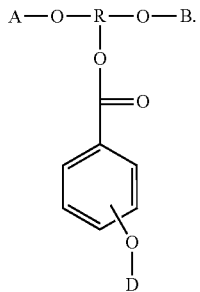

The group —O-D in formula (IIb) may be substituted at the ortho-, meta- or para-position on the aryl ring. In some embodiments, the group —O-D in formula (IIb) may be substituted at the ortho- or para-position on the aryl ring. In a specific embodiment, the group —O-D is para-substituted to provide a moiety of formula (IIc):

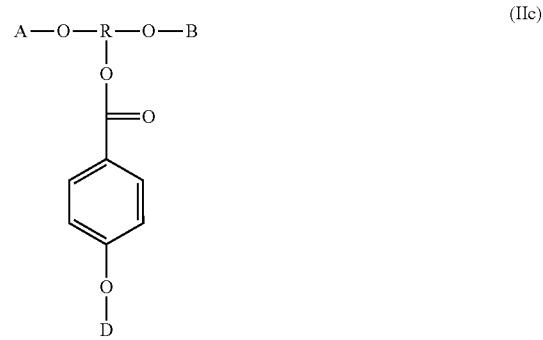

In some embodiments of formula (II), n is 0 and Y at each occurrence is O. In such embodiments, the moiety of formula (II) has a structure of (IId):

In some specific embodiments, the moiety of formula (IId) has a structure of formula (IIe):

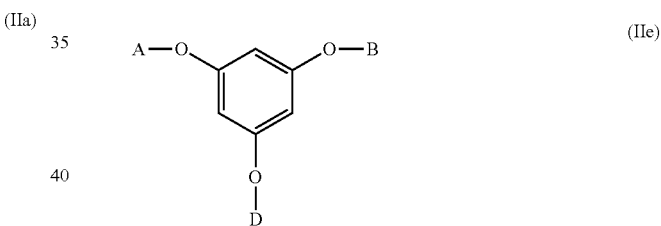

In some specific embodiments, the moiety of formula (IId) has a structure of formula (IIf):

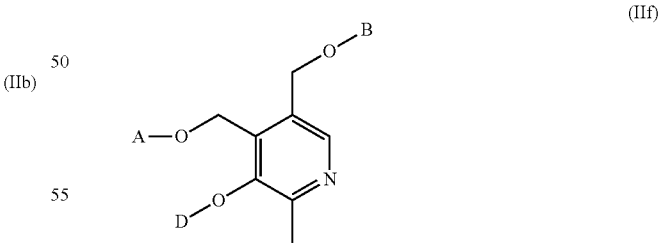

Ideally, the polymer-NSAID conjugate is formed so that the conjugated drug is pendant to the polymer backbone. Preferably, there is minimal incorporation of the drug as a part of the polymer backbone. The pendant configuration is preferred as the drug is released in its active form rather than from intermediate polymer backbone fragments incorporating the drug.

In embodiments of polymer-NSAID conjugates comprising a moiety of formula (II), (IIa), (IIb), (IIc), (IId), (IIe) or (IIf), at least one of A and B comprises a biodegradable polymer. In some embodiments, the biodegradable polymer forms at least a part of A and/or B.

As used herein the term "at least a part" is intended to signify that at least a portion of A and/or B be composed of a biodegradable polymer. Other types of polymer may optionally be present in A and/or B in addition to the biodegradable polymer.

A and B may also each represent a biocompatible polymer backbone.

As used herein, "biocompatible polymer" refers to a polymer that both in its intact, that is, as synthesized state and in its decomposed state (i.e. its degradation products), is compatible with living tissue in that it is not, or at least is minimally, toxic to living tissue; does not, or at least minimally and reparably does, injure living tissue; and/or does not, or at least minimally and/or controllably does, cause an immunological reaction in living tissue.

Biodegradable polymers forming at least a part of A and/or B are generally formed from monomeric units coupled via biodegradable moieties. Polymer-NSAID conjugates of the invention comprising a biodegradable polymer can advantageously biodegrade into substantially non-toxic residues.

The biodegradable polymer forming at least a part of A and/or B may be selected from or comprise a range of materials including: polyurethanes; polyurethanes optionally comprising one or more chain extenders (e.g. polyester); polyesters (eg PLGA (poly(lactic-co-glycolic acid)), PLA (polylactic acid), PGA (polyglycolic acid), PHB (polyhydroxybutyrate), PCL (polycaprolactone); polyamides; polyanhydrides, polycarbonates; polyimides; and combinations thereof. In some embodiments, at least one of A and B is selected from or comprises: polyurethanes; polyesters; polyanhydrides; polyamides, and combinations thereof. In some embodiments, at least one of A and B is selected from or comprises a copolymer of any one of the above-mentioned polymers. In some embodiments, one of A and B is selected from or comprises a biodegradable polymer as described herein. In other embodiments, both A and B is selected from or comprise a biodegradable polymer as described herein.

In some embodiments, the biodegradable polymer forming at least a part of A and/or B may be selected from or comprise a polyester. In that case, the monomeric units that are polymerised to form the polyester, typically a diacid and a diol, will each be coupled via a biodegradable ester moiety.

In some embodiments, the biodegradable polymer forming at least a part of A and/or B may be selected from or comprise a polyurethane. In that case, the monomeric units that are polymerised to form the polyurethane, typically a diisocyanate and a diol, will each be coupled via a biodegradable urethane moiety.

In some embodiments, the biodegradable polymer forming at least a part of A and/or B may be selected from or comprise a copolymer of polyurethane and polyester. In that case, the biodegradable polymer of A and/or B may be a poly(urethane-ester) or a poly(ester-urethane) formed by polymerising a diisocyanate with a polyester macromonomer or macromer. The polyester macromer will be formed from monomeric units that are coupled via a biodegradable moiety (as discussed above), and the polymerisation of it with the diisocyanate will give rise to the poly(urethane-ester) having monomeric units that are all coupled via a biodegradable urethane or ester moiety. The biodegradable polymer of A and/or B may also be a poly(ester-urethane) formed by polymerising a ester containing monomer or macromonomer with a polyurethane macromer. In that case, the polyurethane macromer will be formed from monomeric units that are coupled via a biodegradable moiety (as discussed above), and the polymerisation of it with the ester monomer or macromonomer will give rise to the poly(ester-urethane) having monomeric units that are all coupled via a biodegradable urethane or ester moiety.

In some embodiments, A and B may be selected from or comprise a copolymer of polyurethane and polyether. In that case, the biodegradable polymer of A and/or B may be a poly(urethane-ether) or a poly(ether-urethane) formed by polymerising a diisocyanate with a polyether macromonomer or macromer. The polyether macromer will be formed from monomeric units that are coupled via a ether oxygen moieties, and the polymerisation of it with the diisocyanate will give rise to the poly(urethane-ether) having monomeric units that are all coupled via a urethane or ether moiety. The biodegradable polymer of A and/or B may also be a poly(ether-urethane) formed by polymerising a ether containing monomer or macromonomer with a polyurethane macromonomer or macromer. In that case, the polyurethane macromer will be formed from monomeric units that are coupled via a biodegradable urethane moiety (as discussed above), and the polymerisation of it with the ether monomer or macromonomer will give rise to the poly(ether-urethane).

In embodiments of the invention, the moiety of general formula (II) may in conjunction with a suitable comonomer form a repeat unit of a polyester or polyurethane as illustrated below in general formula (IIg) and (IIh), respectively:

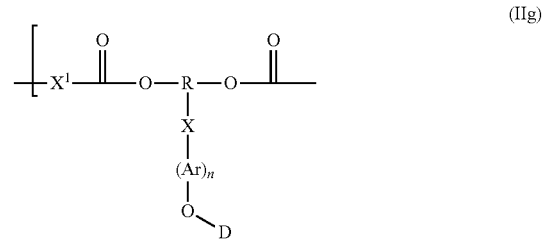

(IIg)

where R, X, Ar, D and n are as herein defined and $X^1$ is an optionally substituted alkyl, aryl or alkylaryl group, wherein for each repeat unit of the polyester each R, X, Ar, D, n and $X^1$ may be the same or different, subject to the provisos defined herein;

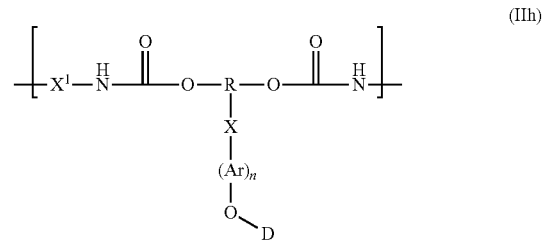

(IIh)

where R, X, Ar, D and n are as herein defined and $X^1$ is an optionally substituted alkyl, aryl or alkylaryl group, wherein for each repeat unit of the polyurethane each R, X, Ar, D, n and $X^1$ may be the same or different, subject to the provisos defined herein.

Polymer-NSAID conjugates of the invention can be advantageously altered to incorporate other monomers or components to provide appropriate polymer properties to suit a particular application (e.g. flexibility, structural strength, rate of release of drug).

The physical properties of material can be altered through changing the composition of the polymer backbone, for example, as represented by A and B in formulae described herein.

In one aspect of the invention, polymer-NSAID conjugates as described herein may include a component that increases the hydrophilicity of the conjugate. Hydrophilic character can be imparted to the polymer-NSAID conjugate through the inclusion of a hydrophilic group. The incorporation of a hydrophilic group in the conjugate may have an influence on the release of the conjugated drug. In some embodiments, the presence of a hydrophilic group may promote release of a conjugated drug.

The hydrophilic group may be provided by or derived from a compound comprising at least one active-hydrogen containing group. Incorporation of the active-hydrogen group containing compound into the conjugate may give rise to a hydrophilic moiety containing at least one active-hydrogen group.

As used herein, the term "active-hydrogen containing group" refers to a group comprising one or more hydrogen atoms that are capable of participating in hydrogen bonding interactions. Groups containing active-hydrogen atoms include for example, hydroxy, amine and carboxylic acid. Compounds containing an active-hydrogen group may comprise a single active-hydrogen group, it they may comprise a plurality of active-hydrogen groups. For example, a hydrophilic group derived from a macromonomer may comprise a plurality of active-hydrogen groups.

In some embodiments, hydrophilic groups present in the polymer-NSAID conjugate comprise a moiety comprising at least one active-hydrogen group, wherein the active-hydrogen group is selected from the group consisting of hydroxy, amine, carboxylic acid, and combinations thereof.

Hydrophilic groups may increase the hydrophilicity of polymer-NSAID conjugates of the invention, for example, by promoting hydrogen bonding interactions with an aqueous environment. In some embodiments, by at least one of A and B comprising a hydrophilic group, the conjugates in accordance with the invention can advantageously help promote efficient drug release. The polymer backbone within the conjugate may exhibit hydrophilic character.

By "hydrophilic" is meant that a segment, substance, component or group as described herein has an affinity for water, or contains groups that will attract water its structure. A hydrophilic segment, substance, component or group will generally be soluble in water or miscible with water. Solubility may be determined by reference to texts such as *The International Pharmacopoeia*, Fourth Edition, 2006. A hydrophilic segment, substance, component or group may possess a solubility of 1 gram (g) of solid in up to 30 milliliters (ml) of aqueous solvent (water) at 20° C.

When present, the hydrophilic group may constitute at least about 1 mol %, at least about 5 mol %, at least about 10 mol %, at least about 15 mol %, or at least 25 mol % of the polymer-NSAID conjugate. The mol % of hydrophilic groups present in the polymer-NSAID conjugate can be determined on the basis of the total number of moles of monomer units used to form the conjugate.

In some embodiments of a polymer-NSAID conjugate comprising a moiety of formula (II), (IIa), (IIb), (IIc), (IId), (IIe) or (IIf), as a part of the polymer backbone, at least one of A and B comprises a hydrophilic group. In some embodiments the hydrophilic group comprises a plurality of active-hydrogen groups.

When present, the hydrophilic group may be incorporated in the conjugate (i) as part of the polymer backbone of the conjugate (ii) in a pendant group that is covalently attached to and pendant from the polymer backbone, or (iii) combinations thereof.

The hydrophilic group is generally a hydrophilic moiety and may comprise or be derived from a hydrophilic low molecular weight compound, a hydrophilic monomer, a hydrophilic oligomer or a hydrophilic polymer.

As used in relation to a molecule or compound as described herein, the term "low molecular weight" denotes a molecular weight selected from the group consisting of no more than about 300 Daltons (Da), no more than about 200 Daltons (Da) and no more than about 100 Daltons (Da).

In polymer-NSAID conjugates of formulae (II), (IIa), (IIb), (IIc), (IId), (IIe) and (IIf) at least one of A and B may comprise a hydrophilic group. In polymer-NSAID conjugates of formulae (IIg) or (IIh), $X^1$ may comprise a hydrophilic group. The hydrophilic group may be present in $X^1$, A and/or B in combination with another polymer, for example, a biodegradable polymer. Biodegradable polymers include polyurethanes, polyesters, poly(ester-urethanes) and poly(urethane-esters) as described herein.

In some embodiments, at least one of A and B comprises at least one hydrophilic group incorporated in the conjugate as part of the polymer backbone.

In some embodiments, at least one of A and B comprises at least one pendant group comprising a hydrophilic group, wherein the pendant group is covalently attached to and pendant from the polymer backbone. In such embodiments, the polymer-NSAID conjugate contains at least one pendant hydrophilic group and pendant drug moieties attached to the polymer backbone. The hydrophilic group may form all of, or a portion of, the pendant group. Generally, the pendant group comprising the hydrophilic group would not also comprise the NSAID drug.

In some embodiments, A and/or B may comprise a combination of pendant and intra-chain incorporated hydrophilic groups.

In some embodiments, the hydrophilic group is derived from, or comprises, at least one selected from the group consisting of poly(ethylene glycol), poly(lactic acid-co-glycolic acid) (PLGA), poly(1,5-dioxepan-2-one) (PDOO), poly(glycerol acetate) (PGAc), poly(hydroxy butyrate),), poly(glycerol phosphate), an amino acid polymer (such as polylysine, polyglutamic acid, etc), an amino acid oligomer, low molecular weight diols (for example C2-C4 diols, such as ethylene glycol, propane diol, propylene glycol, butane diol etc), low molecular weight triols (for example glycerol etc), low molecular weight polyols (for example sugar alcohols, such as mannitol, xylitol, sorbitol, etc) amino acids (lysine, glutamic acid etc), lactic acid, glycolic acid, hydroxy acids (for example, hydroxybutyric acid etc), 1,5-dioxepan-2-one, glycerol acetate, glycerol phosphate, or combinations thereof, or copolymers thereof. In one particular form, the hydrophilic group comprises poly(ethylene glycol).

In some embodiments, the hydrophilic group comprises a hydrophilic oligomer or polymer. Oligomers may contain from 2 to 5 monomeric units, while polymers will generally contain more than 5 monomeric units.

Hydrophilic polymers present in the hydrophilic group may have a molecular weight in the range of from about 200 to about 15,000, preferably in the range of from about 200 to about 10,000. In a preferred embodiment, polymer-NSAID conjugates of the invention may comprise a hydrophilic group comprising poly(ethylene glycol). The poly(ethylene glycol) preferably has a molecular weight in the range of from about 200 to about 3,000.

In one form, the hydrophilic group may comprise a hydrophilic polymer or oligomer derived from one or more monomers comprising an active-hydrogen group. The oligomer or polymer may comprise a plurality of active-hydrogen groups, wherein the active-hydrogen groups are selected from the group consisting of hydroxy, amine, carboxylic acid, and combinations thereof.

One skilled in the art would understand that an active-hydrogen containing monomer is able to polymerise with one or more co-monomers of compatible functionality to form a hydrophilic polymer or oligomer. An active-hydrogen containing monomer may comprise an active-hydrogen group selected from the group consisting of hydroxy, amine, carboxylic acid, and combinations thereof.

In some embodiments, the active-hydrogen containing monomer is at least one selected from the group consisting of low molecular weight diols (for example C2-C4 diols, such as ethylene glycol, propane diol, propylene glycol, butane diol etc), low molecular weight triols (for example glycerol, etc), low molecular weights polyols (for example sugar alcohols, such as mannitol, xylitol, sorbitol, etc), amino alcohols (for example ethanolamine, choline, etc), amino acids (lysine, glutamic acid etc), lactic acid, glycolic acid, hydroxy acids (for example, hydroxybutyric acid etc), 1,5-dioxepan-2-one, glycerol acetate, glycerol phosphate, or combinations thereof. The hydrophilic polymer or oligomer may be a homopolymer formed from a single type of monomer or it may be a copolymer formed from a combination of two or more different types of such monomers.

In some embodiments the hydrophilic group is derived from monomer which may be a macromonomer comprising an oligomeric or polymeric moiety selected from the group consisting of poly(ethylene glycol), poly(lactic acid-co-glycolic acid) (PLGA), poly(1,5-dioxepan-2-one) (PDOO), poly(glycerol acetate) (PGAc), poly(hydroxy butyrate), poly(glycerol phosphate), an amino acid polymer (such as polylysine, polyglutamic acid, etc), or an amino acid oligomer, or combination of, or a copolymer of, such polymeric or oligomeric moieties. For example, a macromonomer may comprise a combination of poly(ethylene glycol) and PLGA.

Macromonomers comprising an oligomeric or polymeric moiety may comprise a plurality of active hydrogen groups. Oligomeric or polymeric moieties present in a macromonomer may or may not be biodegradable.

The incorporation of hydrophilic groups comprising oligomers or polymers such as polylactic-co-glycolic acid (PLGA), and amino acid polymers (such as polylysine, polyglutamic acid, etc) and amino acid oligomers in the polymer backbone of polymer-NSAID conjugates of the invention may be advantageous as such oligomers and polymers are also formed from monomeric units coupled via biodegradable moieties, such as ester and amide moieties. As a result, a fully biodegradable polymer-NSAID conjugate may be produced. Such fully biodegradable conjugates may be particularly suitable for use in implants.

PLGA employed in the invention may comprise lactic acid and glycolic acid at different ratios. The ratio of lactic acid to glycolic acid may be in the range of from 10:90 to 90:10. In general, higher relative amounts of glycolic acid to lactic acid in the PLGA polymer, will provide a hydrophilic group of increased hydrophilicity.

One skilled in the art would appreciate that hydrophilic groups comprising polymers such as poly(ethylene glycol) may not be biodegradable as the monomeric (i.e. diol) units of the poly(ethylene glycol) are coupled via ether moieties which are not biodegradable. However, such groups are generally biocompatible.

In some embodiments A and B independently comprise a polymer selected from the group consisting of polyurethanes, polyesters, poly(urethane-ethers), poly(ester-ethers), poly(urethane-esters), and poly(ester-urethanes). The ether or ester component of the poly(urethane-ethers), poly(ester-ethers), poly(urethane-esters) and poly(ester-urethanes) may represent a hydrophilic group.

In some embodiments the ether component comprises at least one selected from the group consisting of poly(ethylene glycol) (PEG) and poly(glycerol acetate). The ether component may have a molecular weight in the range of from about 200 to about 15,000, preferably from about 200 to about 1,000, more preferably from 200 to about 3000.

In some embodiments the ester component comprises poly(lactide-co-glycolide) (PLGA). The ester component may have a molecular weight in the range of from about 200 to about 15,000, preferably from about 500 to about 5,000. PLGA employed in the invention may comprise lactic acid and glycolic acid at different ratios. The ratio of lactic acid to glycolic acid may be in the range of from 10:90 to 90:10. In general, higher relative amounts of glycolic acid to lactic acid in the PLGA polymer, will provide a more hydrophilic polymer.

In some embodiments the poly(ester-ether) component comprises at least one selected from the group consisting of poly(1,5-dioxepan-2-one) (PDOO). The poly(ester-ether) component may have a molecular weight in the range of from about 200 to about 15,000, preferably from about 500 to about 5,000.

In some embodiments, the polymer-NSAID conjugate of the invention comprises a biodegradable polymer backbone comprising a polyurethane polymer formed with a polyisocyanate and optionally one or more monomers comprising a plurality of active-hydrogen groups selected from hydroxy, amine and carboxylic acid.

In some embodiments A and B independently comprise a biodegradable polymer selected from the group consisting of polyurethanes, polyesters, poly(urethane-ethers), poly(ester-ethers), poly(urethane-esters), and poly(ester-urethanes). The ether or ester component of the poly(urethane-ethers), poly(ester-ethers), poly(urethane-esters) and poly(ester-urethanes) may represent a hydrophilic group.

As discussed above, polymer-NSAID conjugates of the invention comprise a substituted alkanoic acid NSAID conjugated to a polymer backbone. The conjugated NSAID drug moiety is represented by the group "D" in formulae described herein. The drug moiety represented by D may be a releasable NSAID analogue.

In some embodiments D is the acid residue of a substituted alkanoic acid NSAID of formula (III):

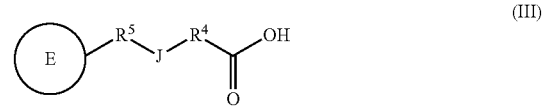

(III)

where:
E represents an optionally substituted ring system;
J is selected from the group consisting of a bond or a functional group;
$R^4$ and $R^5$ are each independently selected from the group consisting of a bond and an optionally substituted aliphatic.

The "acid residue of a substituted alkanoic acid NSAID" is a reference to the drug residue formed after conjugation of the NSAID via a free carboxylic acid functional group to the group Ar. Conjugation of the NSAID to the polymer backbone occurs via an aryl ester linkage. Accordingly, the acid residue is derived from the NSAID molecule after conjugation.

In formula (III), the moiety "E" represents an optionally substituted ring system. In some embodiments, E is selected from the group consisting of an optionally substituted alicyclic ring system (which may be a non-aromatic carbocyclic or non-aromatic heterocyclic) and an optionally substituted aryl ring system (which may be carbocyclic aryl or heterocyclic aryl). Suitable ring systems may contain from 5 to 16 ring members, from 5 to 12 ring members, or from 5 to 6 ring members.

In formula (III), the moiety "J" is selected from the group consisting of a bond or a functional group. When J is a bond, it is suitably a single covalent bond. When J is a functional group, it is preferred that J be an ester functional group (—O(CO)—).

In formula (III), $R^4$ and $R^5$ are each independently selected from the group consisting of a bond and optionally substituted aliphatic.

In some embodiments, $R^4$ is optionally substituted aliphatic. Suitable aliphatic may be linear or branched $C_1$ to $C_3$, (preferably $C_1$ to $C_2$) hydrocarbyl (e.g. methylene or ethylene hydrocarbyl). Suitable optional substituents may include linear or branched $C_1$ to $C_3$ alkyl, preferably $C_1$ alkyl (methyl).

In some embodiments, $R^5$ is an optionally substituted aliphatic. Suitable aliphatic may be linear or branched $C_1$ to $C_3$, (preferably $C_1$ to $C_2$) hydrocarbyl (e.g. methylene or ethylene hydrocarbyl). Suitable optional substituents may include linear or branched $C_1$ to $C_3$ alkyl, preferably $C_1$ alkyl(methyl).

In some embodiments, $R^5$ is a bond.

A substituted alkanoic acid NSAID conjugated to a polymer-NSAID conjugate of the invention is releasable from the conjugate. One advantage of conjugation of the drug through a free carboxylic acid group on the drug means that the drug is releasable, or can be released, in its free acid form.

By the drug being "releasable" is meant that it is capable of being released or cleaved from the aryl ester group as defined in formulae described herein. Upon being released, the drug is bioactive or will be converted in vivo or in vitro to a bioactive form (e.g. as in the case of a prodrug). Release of the drug from the conjugate will allow it to be delivered to a desired site to exert a therapeutic effect.

In order for the drug to be released, the covalent bond between D and oxygen atom in the aryl ester group (e.g. $R^2$—O— or —Ar—O— group) will need to be cleaved. Cleavage of the covalent bond between the D and the oxygen atom can be promoted hydrolytically (i.e. hydrolytic cleavage) and may take place in the presence of water and an acid or a base. In some embodiments the cleavage may take place in the presence of one or more hydrolytic enzymes or other endogenous biological compounds that catalyze or at least assist in the cleavage process. Hydrolytic cleavage of the ester bond produces a carboxylic acid and an alcohol. As the conjugated drug is a substituted alkanoic acid NSAID, cleavage of the ester bond releases the drug in its free acid form while an alcohol (hydroxy) functional group is generated on the oxygen atom linked to the group $R^2$ or to the group Ar.

It is preferable that the drug moiety (D) be released from the polymer-NSAID conjugate at a rate that is at least equal to or faster than the rate of cleavage of the biodegradable moieties forming part of the polymer backbone. That is, the aryl ester or heteroaryl ester group linking D to the polymer backbone should as labile, or more labile, than the biodegradable moieties forming part of the polymer backbone. Accordingly, drug release from the polymer-NSAID conjugate as a result of cleavage or hydrolysis of the aryl ester or heteroaryl ester linkage occurs at a rate that is at least equal to, or faster than, the rate of erosion of biodegradable moieties in the polymer backbone. In specific embodiments, it is preferred that the substituted NSAID drug moiety (D) be released at a rate that is faster than the rate of erosion or degradation of the biodegradable moieties forming part of the polymer backbone.

In embodiments of the invention the NSAIDs are released such that they do not comprise a residue derived from the polymer backbone or ester linking group (i.e. $R^2$—O or Ar—O)). By this it is meant that the drugs are released in their substantially original form (i.e. before being conjugated) and are essentially free from, for example, fragments of oligomer or polymer derived from the polymer backbone. For example, when Y forms part of an ester moiety, it is preferred that the ester moiety be less labile than the aryl ester linkage conjugating the drug moiety (D) to the polymer backbone. In this manner, the conjugated drug can be released from the polymer conjugate in its active form and free from fragments derived from the polymer backbone.

In some embodiments, D is the acid residue of a substituted NSAID having a structure of formula (IIIa):

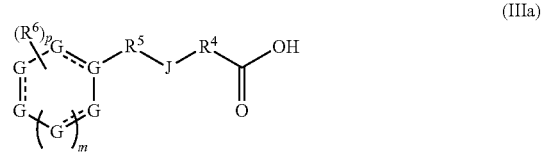

(IIIa)

where:
G at each occurrence is independently selected from the group consisting of a carbon atom and a heteroatom;
------------- represents an optional bond;
$R^6$ is a substituent group;
p represents the number of substituent groups and is an integer in the range of from 0 to 5;
m is 0 or 1; and
$R^4$, $R^5$ and J are as defined in formula (III).

In some embodiments of formula (IIIa) $R^4$ is an optionally substituted $C_1$-$C_2$ hydrocarbyl, and J and $R^5$ each represent a bond. Such compounds may be represented by compounds of formula (IIIb) or (IIIc):

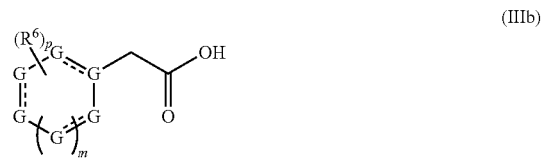

(IIIb)

-continued

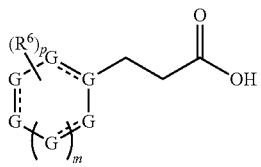

(IIIc)

where: G, $R^6$, p and m are as defined herein.

A skilled person would be able to ascertain the chemical structure of a variety of substituted alkanoic acid NSAIDs. Examples of substituted alkanoic NSAIDs that may be delivered by polymer-NSAID conjugates of the invention are shown in Table 1.

TABLE 1

| Name | Structure |
|---|---|
| Aceclofenac | 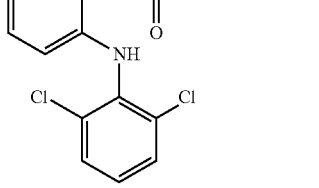 |
| Alminoprofen | 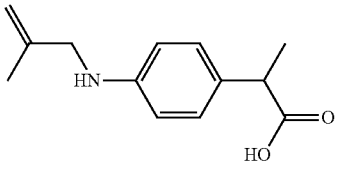 [SMILES: C=C(C)CNc1ccc(C(C)C(=O)O)cc1] |
| Amfenac | 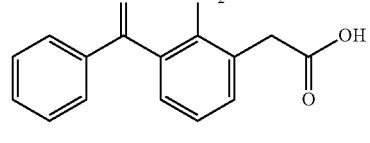 |
| Bromfenac | 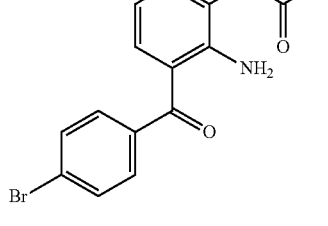 |
| Carprofen | 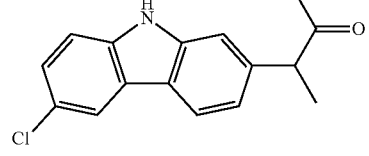 |
| Diclofenac | 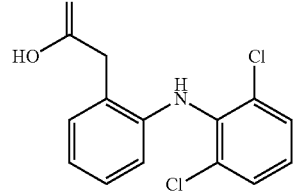 |

TABLE 1-continued
| Name | Structure |
|---|---|
| Enfenamic Acid | 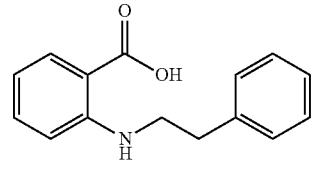 [SMILES: O=C(O)c1ccccc1NCCc1ccccc1] |
| Etodolac | 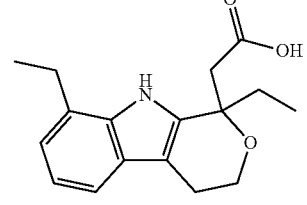 |
| Flufenamic Acid | 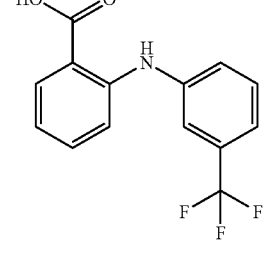 |
| Meclofenamic Acid | 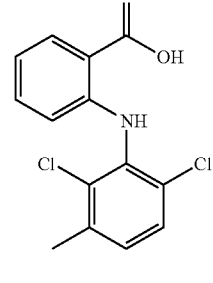 |
| Mefenamic Acid | 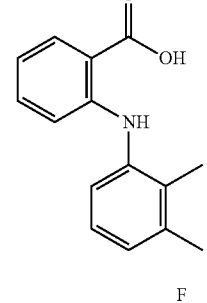 |
| Niflumic Acid | 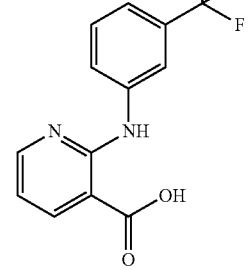 |

TABLE 1-continued

| Name | Structure |
|---|---|
| Tolfenamic Acid | 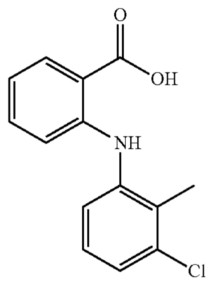 [SMILES: Cc1c(Cl)cccc1Nc1ccccc1C(=O)O] |
| Bendazac | 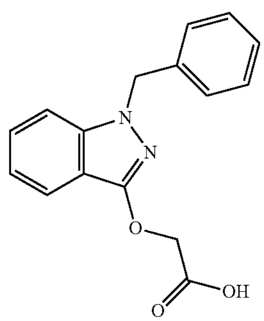 [SMILES: O=C(O)COc1nn(Cc2ccccc2)c2ccccc12] |
| Benoxaprofen | 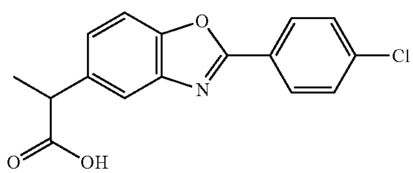 [SMILES: CC(C(=O)O)c1ccc2oc(-c3ccc(Cl)cc3)nc2c1] |
| Bermoprofen | 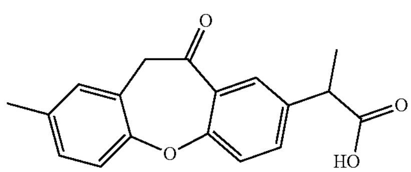 [SMILES: Cc1ccc2c(c1)CC(=O)c1cc(C(C)C(=O)O)ccc1O2] |
| Bucloxic Acid | 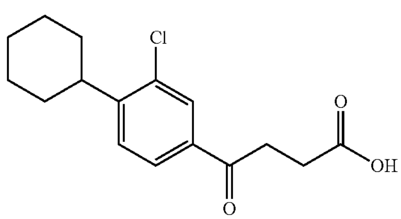 [SMILES: O=C(O)CCC(=O)c1ccc(C2CCCCC2)c(Cl)c1] |
| Butibufen | 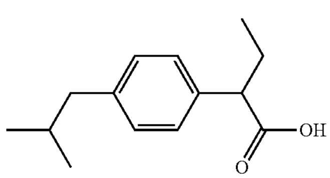 [SMILES: CCC(C(=O)O)c1ccc(CC(C)C)cc1] |

TABLE 1-continued

| Name | Structure |
|---|---|
| Cinmetacin | 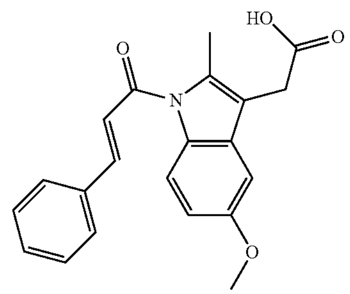 [SMILES: COc1ccc2c(c1)c(CC(=O)O)c(C)n2C(=O)/C=C/c1ccccc1] |
| Clidanac | 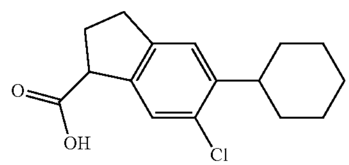 [SMILES: O=C(O)C1CCc2cc(C3CCCCC3)c(Cl)cc21] |
| Clopirac | 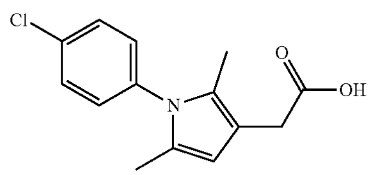 [SMILES: Cc1cc(CC(=O)O)c(C)n1-c1ccc(Cl)cc1] |
| Dexibuprofen | 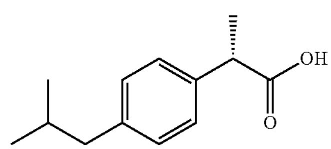 |
| Dexketoprofen | 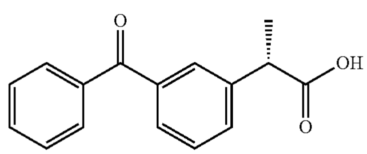 [SMILES: C[C@H](C(=O)O)c1cccc(C(=O)c2ccccc2)c1] |
| Felbinac | 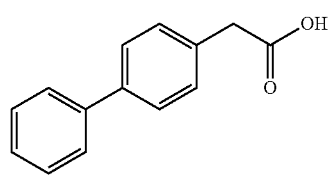 [SMILES: O=C(O)Cc1ccc(-c2ccccc2)cc1] |
| Fenbufen | 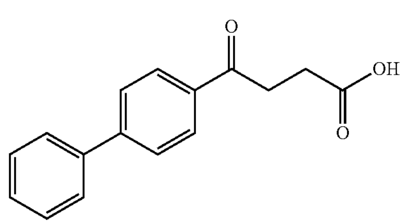 [SMILES: O=C(O)CCC(=O)c1ccc(-c2ccccc2)cc1] |
| Fenclozic Acid | 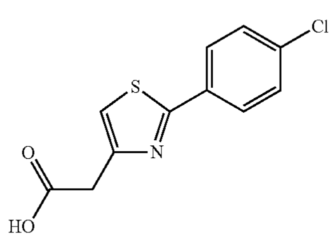 [SMILES: O=C(O)Cc1csc(-c2ccc(Cl)cc2)n1] |

TABLE 1-continued
| Name | Structure |
|---|---|
| Fenoprofen | 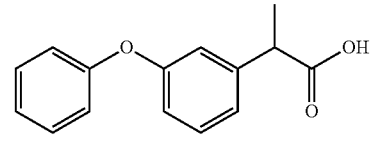 [SMILES: CC(C(=O)O)c1cccc(Oc2ccccc2)c1] |
| Fentiazac | 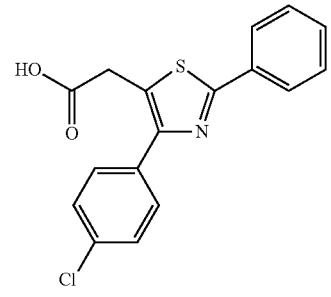 [SMILES: O=C(O)Cc1sc(-c2ccccc2)nc1-c1ccc(Cl)cc1] |
| Flunoxaprofen | 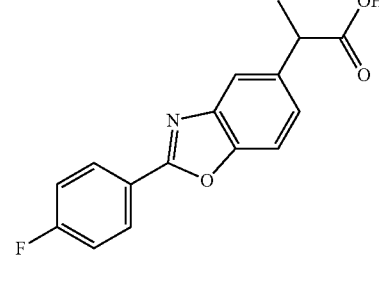 |
| Flunixin | 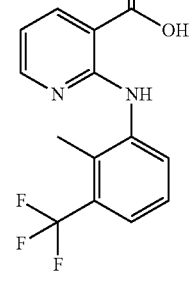 |
| Flurbiprofen | 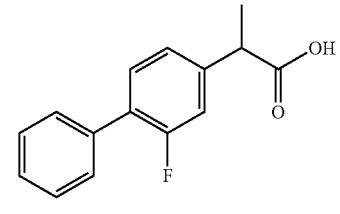 [SMILES: CC(C(=O)O)c1ccc(-c2ccccc2)c(F)c1] |
| Ibuprofen | 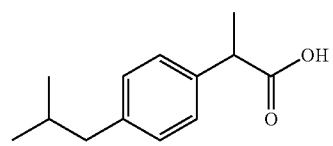 |

TABLE 1-continued

| Name | Structure |
| --- | --- |
| Indomethacin | 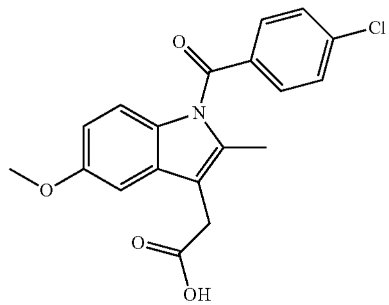 [SMILES: COc1ccc2c(c1)c(CC(=O)O)c(C)n2C(=O)c1ccc(Cl)cc1] |
| Isofezolac | 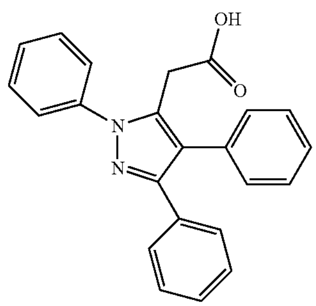 [SMILES: O=C(O)Cc1c(-c2ccccc2)c(-c2ccccc2)nn1-c1ccccc1] |
| Isoxepac | 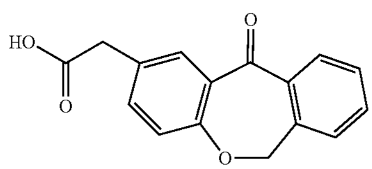 [SMILES: O=C(O)Cc1ccc2c(c1)C(=O)c1ccccc1CO2] |
| Licofelone | 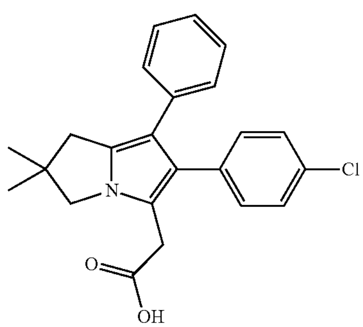 [SMILES: CC1(C)Cc2c(-c3ccccc3)c(-c3ccc(Cl)cc3)c(CC(=O)O)n2C1] |
| Lonazolac | 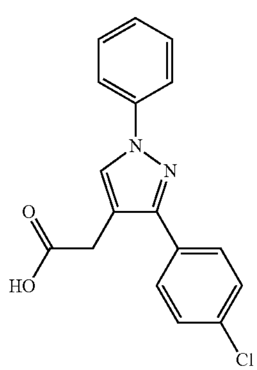 [SMILES: O=C(O)Cc1cn(-c2ccccc2)nc1-c1ccc(Cl)cc1] |

TABLE 1-continued

| Name | Structure |
| --- | --- |
| Lumiracoxib | 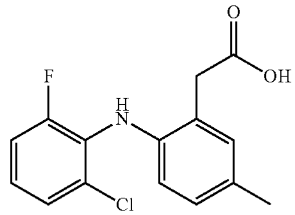 [SMILES: Cc1ccc(Nc2c(F)cccc2Cl)c(CC(=O)O)c1] |
| Metiazinic Acid | 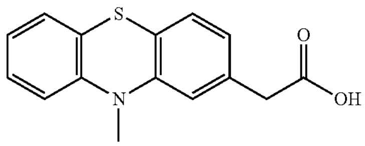 [SMILES: CN1c2ccccc2Sc2ccc(CC(=O)O)cc21] |
| Naproxen | 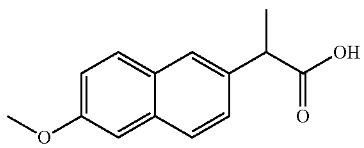 [SMILES: COc1ccc2cc(C(C)C(=O)O)ccc2c1] |
| Oxaprozin | 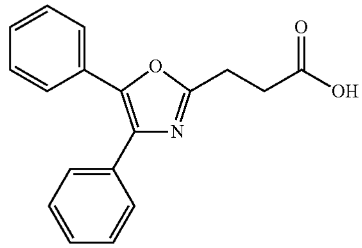 [SMILES: O=C(O)CCc1nc(-c2ccccc2)c(-c2ccccc2)o1] |
| Pirazolac | 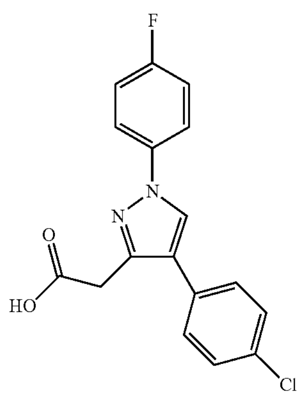 [SMILES: O=C(O)Cc1nn(-c2ccc(F)cc2)cc1-c1ccc(Cl)cc1] |
| Pirprofen | 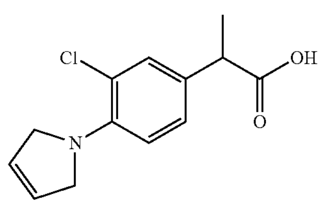 [SMILES: CC(C(=O)O)c1ccc(N2CC=CC2)c(Cl)c1] |
| Pranoprofen | 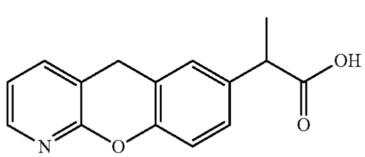 [SMILES: CC(C(=O)O)c1ccc2c(c1)Cc1cccnc1O2] |

TABLE 1-continued
| Name | Structure |
|---|---|
| Protizinic Acid | 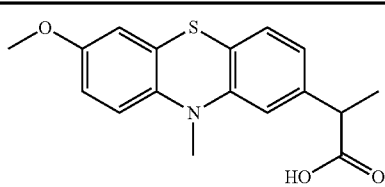 |
| Sulindac | 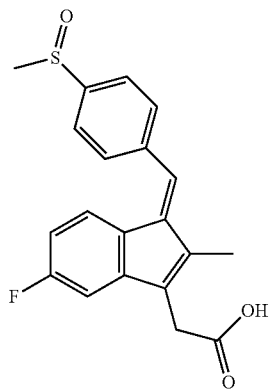 [SMILES: CC1=C(CC(=O)O)c2cc(F)ccc2/C1=C\c1ccc(S(C)=O)cc1] |
| Suprofen | 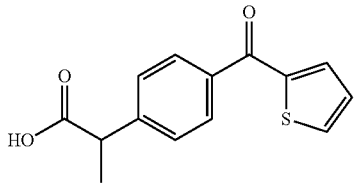 [SMILES: CC(C(=O)O)c1ccc(C(=O)c2cccs2)cc1] |
| Tiaprofenic Acid | 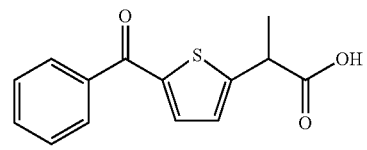 [SMILES: CC(C(=O)O)c1ccc(C(=O)c2ccccc2)s1] |
| Tolmetin | 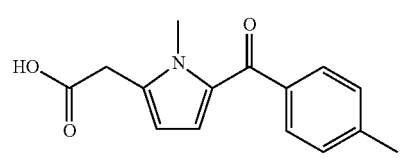 [SMILES: Cc1ccc(C(=O)c2ccc(CC(=O)O)n2C)cc1] |
| Ketoprofen | 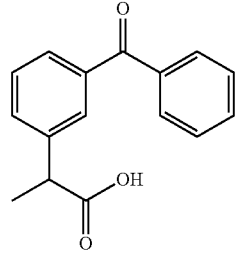 [SMILES: CC(C(=O)O)c1cccc(C(=O)c2ccccc2)c1] |
| Loxoprofen | 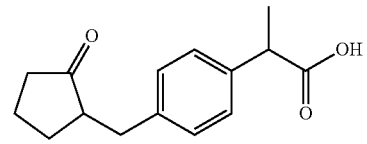 [SMILES: CC(C(=O)O)c1ccc(CC2CCCC2=O)cc1] |

TABLE 1-continued

| Name | Structure |
|---|---|
| Zaltoprofen | 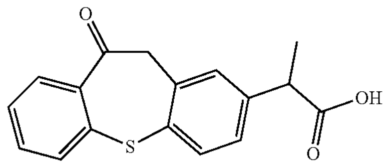 [SMILES: CC(C(=O)O)c1ccc2c(c1)CC(=O)c1ccccc1S2] |
| Balsalazide | 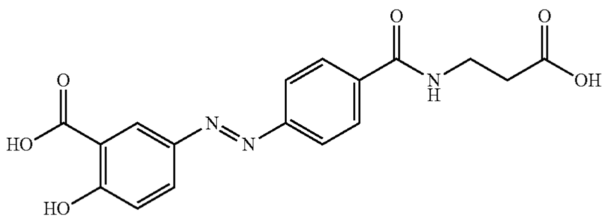 [SMILES: O=C(O)CCNC(=O)c1ccc(/N=N/c2ccc(O)c(C(=O)O)c2)cc1] |
| Fendosal | 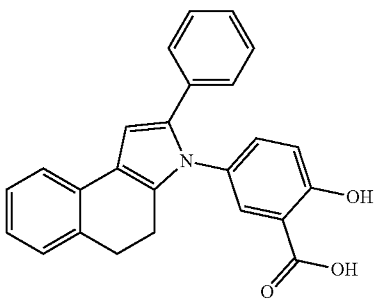 [SMILES: O=C(O)c1cc(-n2c(-c3ccccc3)cc3c2CCc2ccccc2-3)ccc1O] |
| Olsalazine | 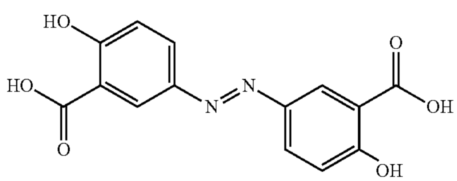 [SMILES: O=C(O)c1cc(/N=N/c2ccc(O)c(C(=O)O)c2)ccc1O] |
| Ximoprofen | 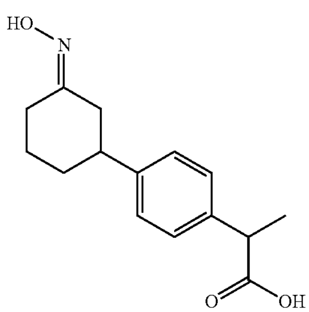 [SMILES: CC(C(=O)O)c1ccc(C2CCC/C(=N\O)C2)cc1] |
| Mesalamine | 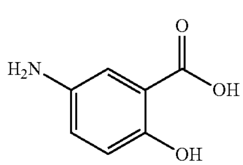 [SMILES: Nc1ccc(O)c(C(=O)O)c1] |
| Sulfasalazine | 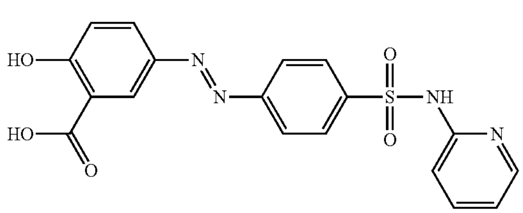 [SMILES: O=C(O)c1cc(/N=N/c2ccc(S(=O)(=O)Nc3ccccn3)cc2)ccc1O] |

TABLE 1-continued

| Name | Structure |
|---|---|
| Acetylsalicyl salicylic acid | 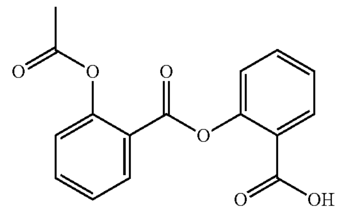 [SMILES: CC(=O)Oc1ccccc1C(=O)Oc1ccccc1C(=O)O] |
| Alclofenac | 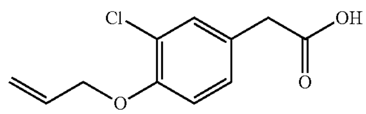 |
| Aspirin | 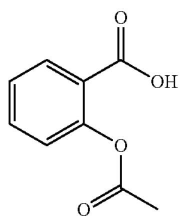 |
| 5-Bromosalicylic acid acetate | 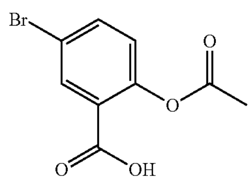 |
| Cinchophen | 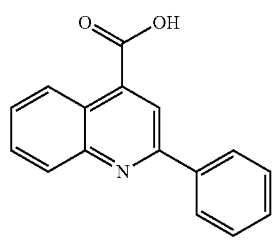 [SMILES: O=C(O)c1cc(-c2ccccc2)nc2ccccc12] |
| Diacerein | 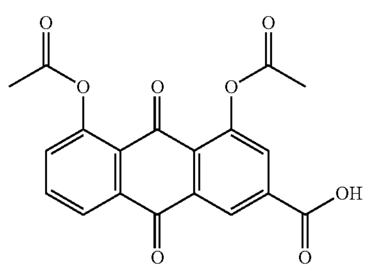 [SMILES: CC(=O)Oc1cccc2c1C(=O)c1c(OC(C)=O)cc(C(=O)O)cc1C2=O] |
| Dipyrocetyl | 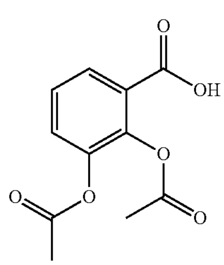 [SMILES: CC(=O)Oc1cccc(C(=O)O)c1OC(C)=O] |

TABLE 1-continued

| Name | Structure |
|---|---|
| Fosfosal | 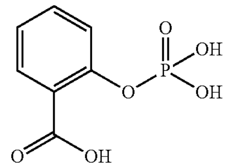 [SMILES: O=C(O)c1ccccc1OP(=O)(O)O] |
| Ibufenac | 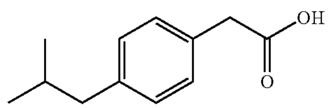 |
| Indoprofen | 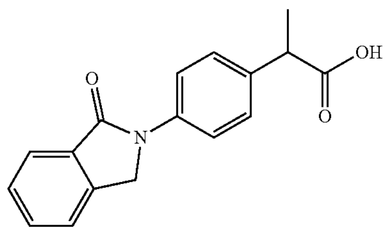 [SMILES: CC(C(=O)O)c1ccc(N2Cc3ccccc3C2=O)cc1] |
| Clometacin | 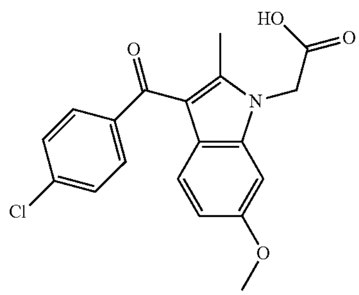 [SMILES: COc1ccc2c(C(=O)c3ccc(Cl)cc3)c(C)n(CC(=O)O)c2c1] |
| Ketorolac | 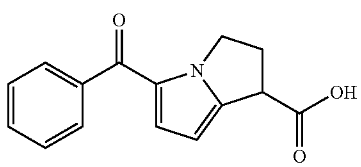 [SMILES: O=C(c1ccccc1)c1ccc2n1CCC2C(=O)O] |
| Zomepirac | 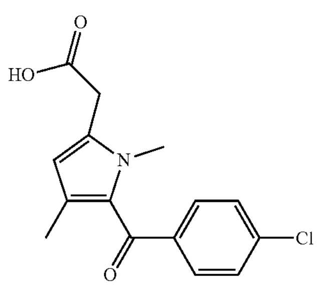 [SMILES: Cc1cc(CC(=O)O)n(C)c1C(=O)c1ccc(Cl)cc1] |
| Actarit | 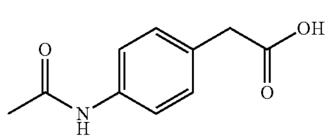 |
| Clonixin | 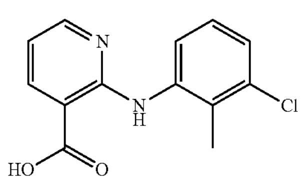 [SMILES: Cc1c(Cl)cccc1Nc1ncccc1C(=O)O] |

TABLE 1-continued

| Name | Structure |
|---|---|
| Salicylamide O-acetic acid | 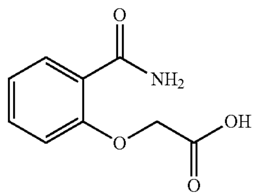 [SMILES: NC(=O)c1ccccc1OCC(=O)O] |
| Diflunisal | 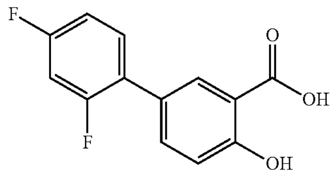 [SMILES: O=C(O)c1cc(-c2ccc(F)cc2F)ccc1O] |
| Gentisic acid | 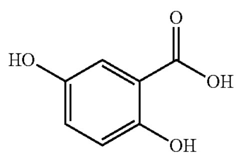 [SMILES: O=C(O)c1cc(O)ccc1O] |
| Salsalate | 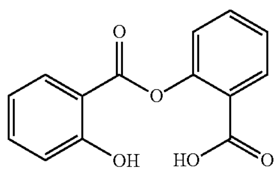 [SMILES: O=C(Oc1ccccc1C(=O)O)c1ccccc1O] |
| Mofezolac | 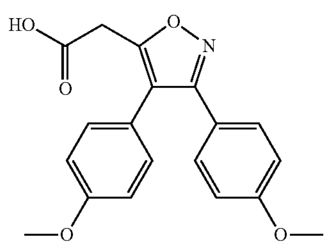 |

Substituted alkanoic acid NSAIDs such as those listed in Table 1 may be acetic acid or propionic acid derivatives. The present invention is generally applicable to the class of substituted alkanoic acid NSAID due to the structural similarity of the drug compounds in the alkanoic acid group that conjugates the drug to the aryl ester linkage. The performance of the polymer-NSAID conjugates of the invention in terms of release of the drug is therefore applicable across the range of drugs in this class.

In some forms of a polymer-NSAID conjugate of the invention as defined herein, D is the acid residue of an alkanoic acid NSAID selected from the group consisting of aceclofenac, alminoprofen, amfenac, carprofen, diclofenac, enfenamic acid, etodolac, flufenamic acid, meclofenamic acid, mefenamic acid, niflumic acid, tolfenamic acid, benoxaprofen, bermoprofen, bucloxic acid, butibufen, cinmetacin, clidanac, clopirac, dexibuprofen, dexketoprofen, felbinac, fenbufen, fenclozic acid, fenoprofen, fentiazac, flunoxaprofen, flunixin, flurbiprofen, ibuprofen, indomethacin, isofezolac, isoxepac, ketoprofen, licofelone, lonazolac, loxoprofen, lumiracoxib, metiazinic acid, mofezolac, naproxen, oxaprozin, pirazolac, pirprofen, pranoprofen, protizinic acid, sulindac, suprofen, tiaprofenic acid, tolmetin, bermoprofen, bucloxic acid, isoxepac, ketoprofen, loxoprofen, zaltoprofen, balsalazide, fendosal, olsalazine, ximoprofen, mesalamine, sulfasalazine, acetylsalicylsalicylic acid, alclofenac, aspirin, benoxaprofen, 5-bromosalicylic acid acetate, cinchophen, diacerein, dipyrocetyl, fosfosal, ibufenac, indoprofen, clometacin, ketorolac, zomepirac, actarit, clonixin, salicylamide O-acetic acid, diflunisal, gentisic acid, and salsalate.

In particular embodiments, D is the acid residue of an alkanoic acid NSAID selected from the group consisting of diclofenac, ketorolac, and indomethacin.

In one embodiment, the present invention provides a polymer-drug conjugate comprising as part of its polymer backbone a moiety of general formula (II):

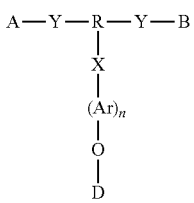

(II)

where:
A and B, which may be the same or different, each represent a biodegradable polymer backbone and are (i) attached to the —Y—R(X—(Ar)n-O-D)-Y— moiety as shown in formula (II) via a biodegradable moiety, and (ii) optionally, at least one of A and B comprises a hydrophilic group;
R comprises an optionally substituted aliphatic or an optionally substituted aryl;
Y at each occurrence is —O—;
X is a bond or a linking group;
Ar is optionally substituted aryl;
n is an integer selected from 0 and 1; and
D is a releasable drug of general formula (IIId):

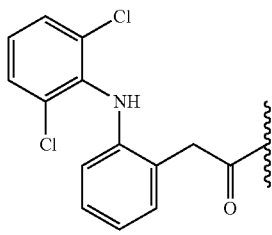

(IId)

where ⌇ represents where the drug is attached to the group —Ar—O—, with the proviso that when R is optionally substituted aliphatic then n is 1, and when R is optionally substituted aryl then n is 0 or 1.

In some embodiments, at least one of A and B comprises a hydrophilic group.

The present invention also relates to a polymer-NSAID conjugate obtained by polymerising a NSAID-monomer conjugate with at least one monomer comprising compatible chemical functionality.

The present invention also relates to a method for preparing a polymer-NSAID conjugate comprising the step of polymerising a NSAID-monomer conjugate with at least one monomer comprising compatible chemical functionality.

The present invention also relates to a NSAID-monomer conjugate for preparing a polymer-NSAID conjugate as described herein.

In embodiments of the invention, the NSAID-monomer conjugate has a structure of formula (IV):

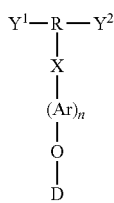

(IV)

where:
$Y^1$ and $Y^2$ each independently represent a terminal reactive functional group, or $Y^1$ and $Y^2$ together form part of a cyclic functional group capable of ring-opening;
R comprises an optionally substituted aliphatic or an optionally substituted aryl;
X is a bond or a linking group;
Ar is optionally substituted aryl;
D is the carboxylic acid residue of the ester formed with a substituted alkanoic acid NSAID; and
n is an integer selected from 0 and 1,
with the proviso then when R comprises optionally substituted aryl then n is 1, and when R comprises optionally substituted aryl then n is 0 or 1.

In accordance with one aspect the present invention also provides a polymer-NSAID conjugate obtained by polymerising a NSAID-monomer conjugate of formula (IV):

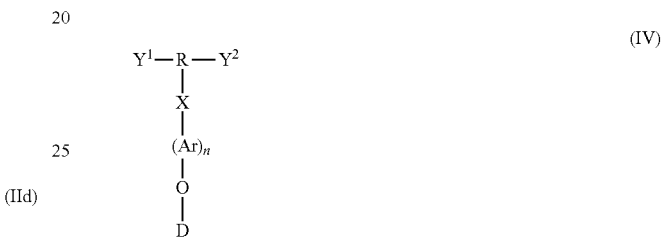

(IV)

where:
$Y^1$ and $Y^2$ each independently represent a terminal reactive functional group, or $Y^1$ and $Y^2$ together form part of a cyclic functional group capable of ring-opening;
R comprises an optionally substituted aliphatic or an optionally substituted aryl;
X is a bond or a linking group;
Ar is optionally substituted aryl;
D is the carboxylic acid residue of the ester formed with a substituted alkanoic acid NSAID; and
n is an integer selected from 0 and 1,
with the proviso then when R comprises optionally substituted aryl then n is 1, and when R comprises optionally substituted aryl then n is 0 or 1,
with at least one monomer comprising compatible chemical functionality.

In accordance with another aspect the present invention also provides a method for preparing a polymer-NSAID conjugate comprising the step of polymerising a NSAID-monomer conjugate of formula (IV)

(IV)

where:
$Y^1$ and $Y^2$ each independently represent a terminal reactive functional group, or $Y^1$ and $Y^2$ together with R form part of a cyclic functional group capable of ring-opening;

R comprises an optionally substituted aliphatic or an optionally substituted aryl;

X is a bond or a linking group;

Ar is optionally substituted aryl;

D is the carboxylic acid residue of the ester formed with a substituted alkanoic acid NSAID; and n is an integer selected from 0 and 1, with the proviso then when R comprises optionally substituted aryl then n is 1, and when R comprises optionally substituted aryl then n is 0 or 1, with at least one monomer comprising compatible chemical functionality.

In the NSAID-monomer conjugate of formula (IV), the groups R, X, Ar and D may be selected from any one of the groups described herein, subject to the provisos defined herein.

The acid residue of the drug is conjugated to a monomer via an aryl ester linking group. Examples of aryl ester groups (i.e. $R^2$—O-D or Ar—O-D groups) are discussed herein.

In some embodiments of a NSAID-monomer conjugate of formula (IV), R comprises an optionally substituted aliphatic and n is 1 such that the NSAID-monomer conjugate of formula (IV) has a structure of formula (IVa):

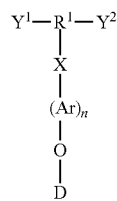

(IVa)

where:

Y$^1$ and Y$^2$ each independently represent a terminal reactive functional group, or Y$^1$ and Y$^2$ together with R form part of a cyclic functional group capable of ring-opening;

R$^1$ comprises an optionally substituted aliphatic;

X is a bond or a linking group;

Ar is an optionally substituted aryl; and

D is the carboxylic acid residue of the ester formed with a substituted alkanoic acid NSAID.

In some forms of a NSAID-monomer conjugate of formula (IVa) Ar comprises from 5 to 12 ring members. In some forms, Ar is an optionally substituted $C_5$-$C_{12}$ aryl (preferably optionally substituted phenyl).

In some embodiments of a NSAID-monomer conjugate of formula (IVa) the group —X—Ar—O— is —OC(O)—C5-12aryl-O—.

In some embodiments, the NSAID-monomer conjugate of formula (IVa) is of formula (IVb):

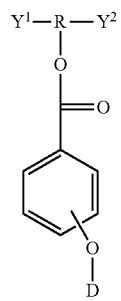

(IVb)

In some embodiments, the NSAID-monomer conjugate of formula (IV) is of formula (IVc):

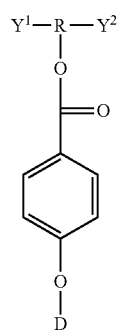

(IVc)

In some embodiments of a NSAID-monomer conjugate of formula (IV), R comprises an optionally substituted aryl such that the NSAID-monomer conjugate of formula (IV) has a structure of formula (IVd):

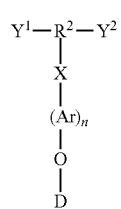

(IVd)

where:

Y$^1$ and Y$^2$ each independently represent a terminal reactive functional group, or Y$^1$ and Y$^2$ together with R form part of a cyclic functional group capable of ring-opening;

R$^2$ comprises an optionally substituted aryl;

X is a bond or a linking group;

Ar is an optionally substituted aryl;

D is the carboxylic acid residue of the ester formed with a substituted alkanoic acid NSAID; and n is an integer selected from 0 and 1, with the proviso that when n is 0 then X is a bond.

In some embodiments of a NSAID-monomer conjugate of formula (IVd), n is 0. In such embodiments X is preferably a bond such that the group —O-D is directly attached to R$^2$ as illustrated in formula (IVe):

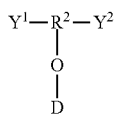
(IVe)

where Y¹, Y², R² and D are as defined in formula (IVd).

In other embodiments of a moiety of formula (IVd), n is 1. In such embodiments the group —O-D is attached to Ar as illustrated in formula (IVf):

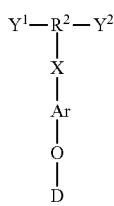
(IVf)

where Y¹, Y², R², X. Ar and D are as defined in formula (IVd).

In formulae (IVd), (IVe) and (IVf), R² comprises an optionally substituted aryl.

In particular embodiments, the NSAID-monomer conjugate of formula (IVd) is of formula (IVg):

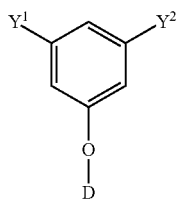
(IVg)

The groups "Y¹" and "Y²" in NSAID-monomer conjugates of the invention may each independently represent a terminal reactive functional group.

In some embodiments, Y¹ and Y² are independently selected from the group consisting hydroxy, isocyanate, anhydride, carboxylic acid, carboxylic acid ester, carboxylic acid halide and amine.

In some embodiments, Y¹ and Y² are each hydroxy. In that case, the NSAID-monomer conjugate of formula (IV) will be a diol having a structure of formula (IVh):

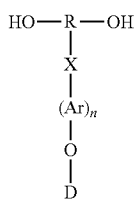
(IVh)

where: R, X, Ar, D and n are as defined herein, subject to the provisos defined herein.

In some embodiments, the NSAID-monomer conjugate of formula (IVh) may have a structure as shown in the following illustrations:

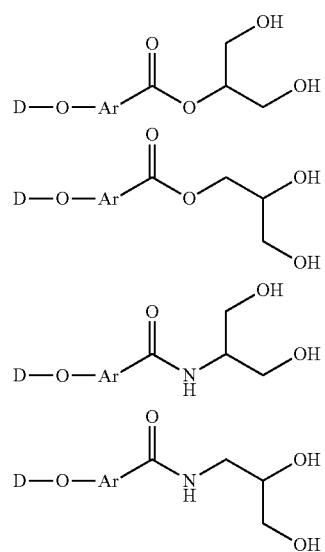

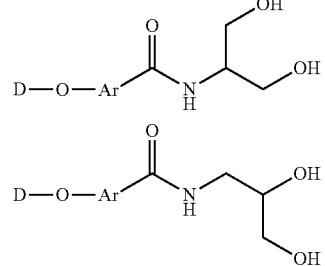

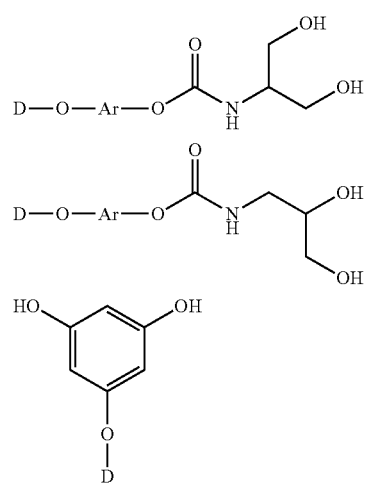

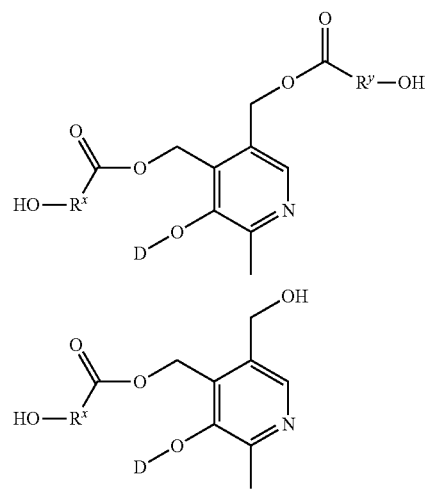

where $R^x$ and $R^y$ are each independently selected from optionally substituted aliphatic.

Some specific embodiments of NSAID-monomer conjugates of the invention are shown below:

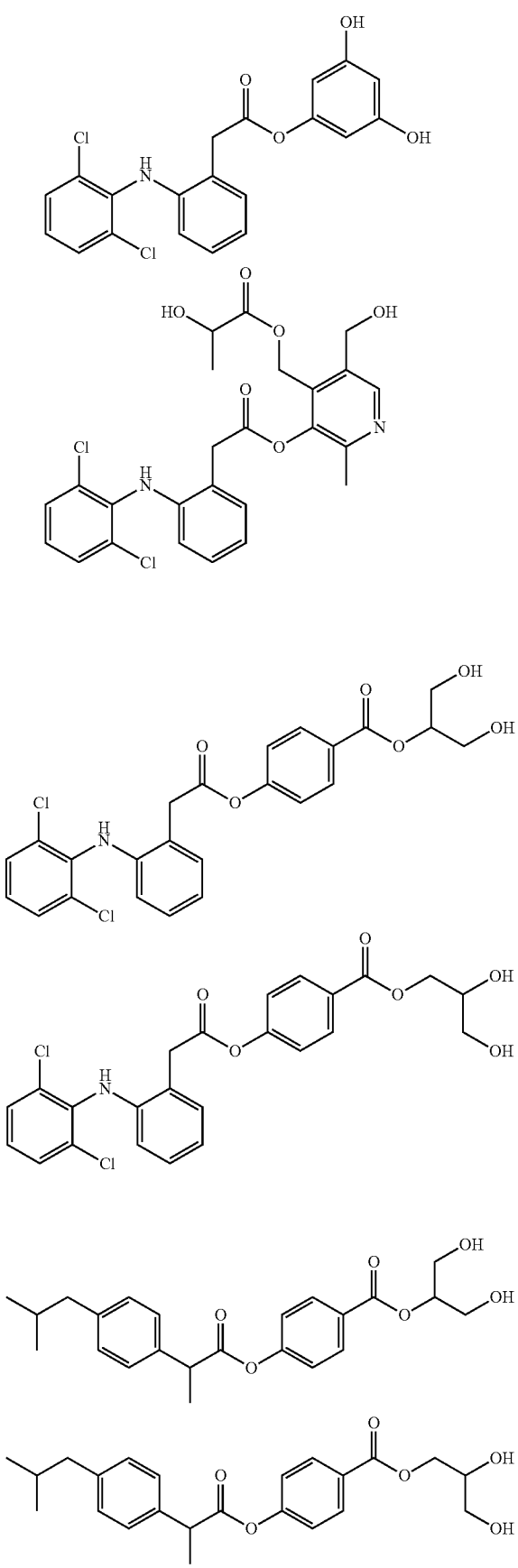
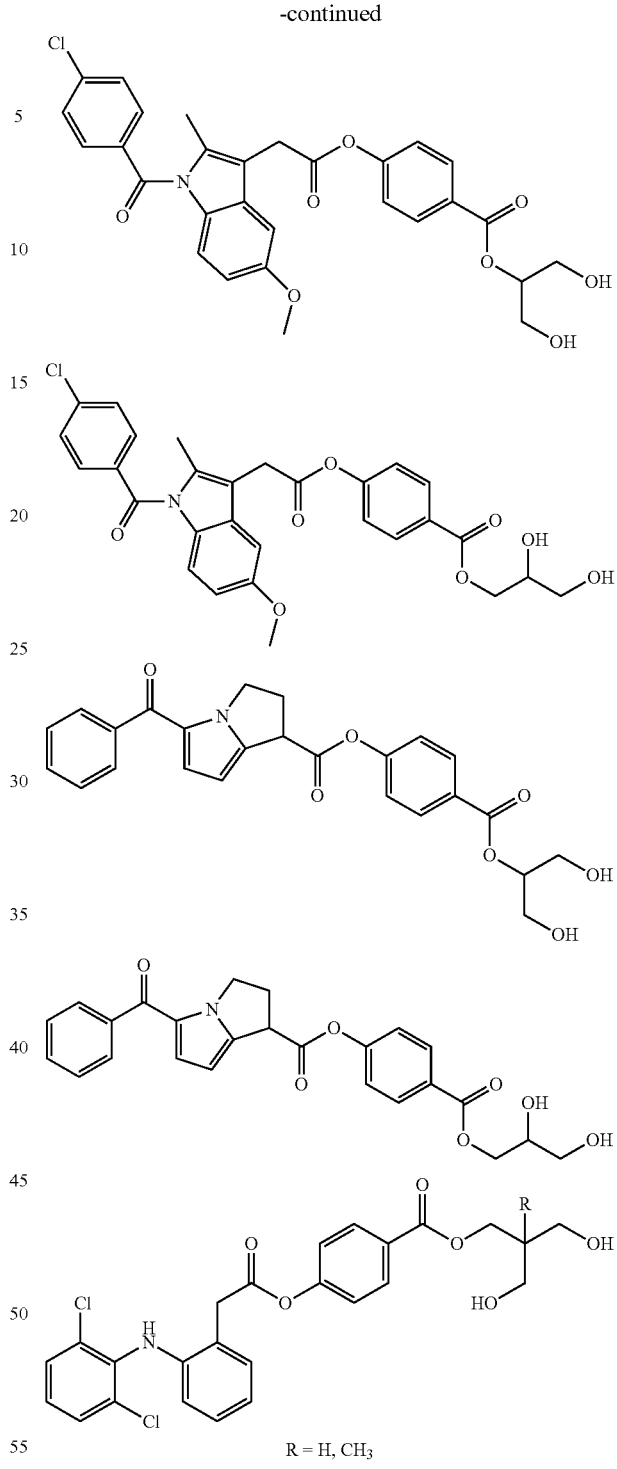

R = H, CH₃

Techniques, equipment and reagents well known in the art can advantageously be used to prepare the NSAID-monomer conjugates in accordance with the invention. For example, NSAID-monomer conjugates of formula (IV) may be synthesised using protecting group strategies known to one skilled in the relevant art.

Examples of general strategies for synthesising NSAID-monomer conjugates of formula (IV), which employ protecting group strategies, are represented in Scheme 1 below:

Scheme 1: Strategies for synthesising NSAID-monomer conjugates of formula (IV).
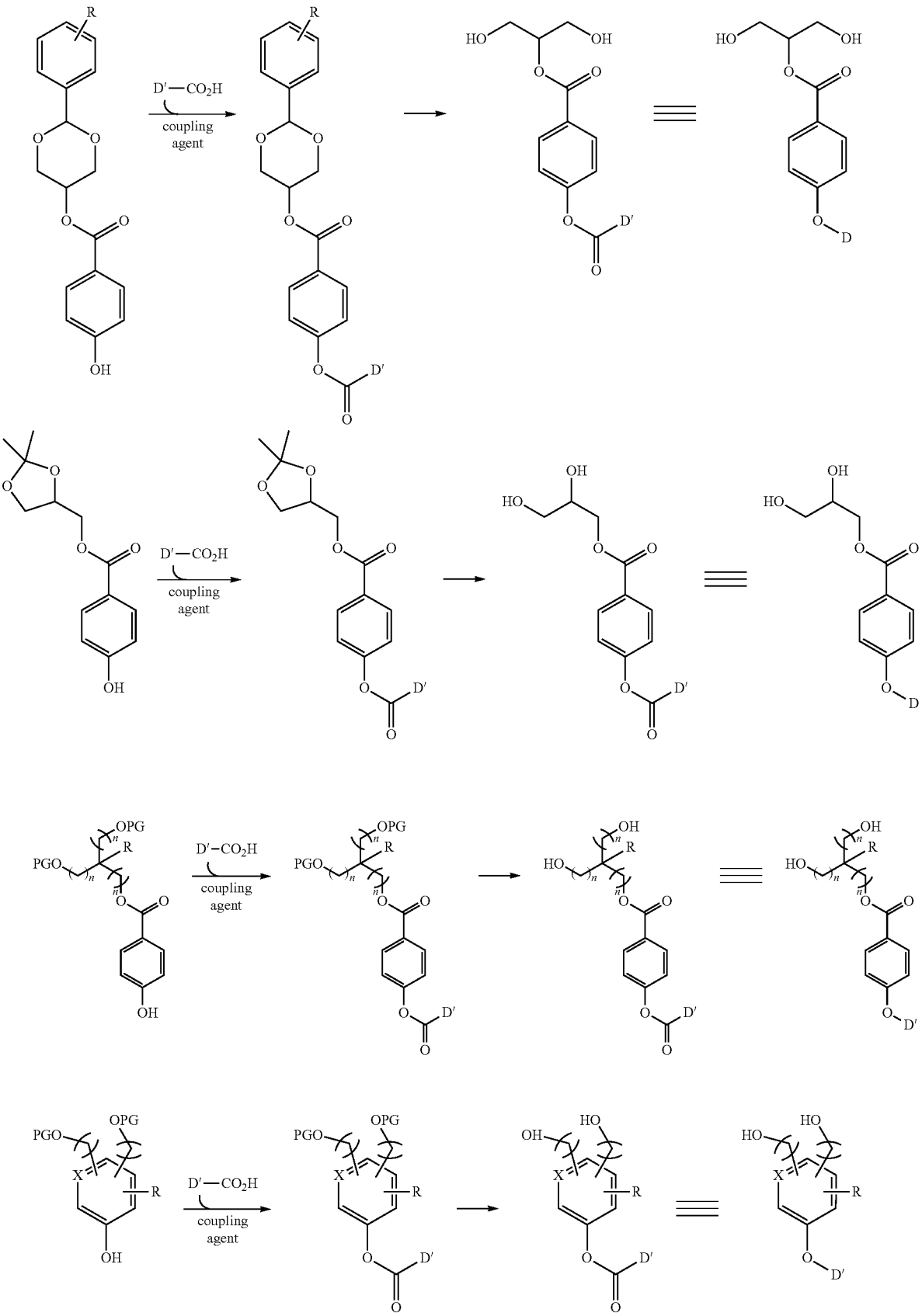

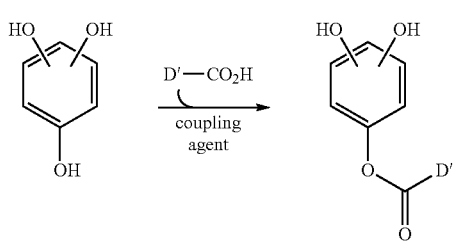 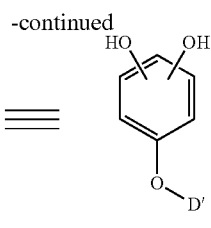

Diol NSAID-monomer conjugates of formula (IVh) with various "R" groups may be prepared by conjugating a substituted NSAID to a polyfunctional precursor molecule comprising at least two hydroxy groups. Examples of some precursor molecules useful for forming NSAID-monomer conjugates are shown below:

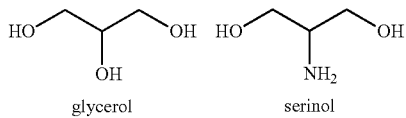

glycerol     serinol

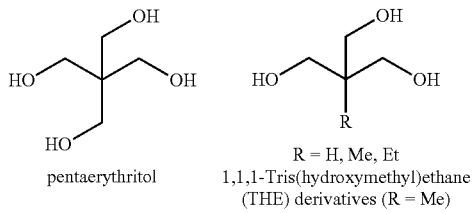

pentaerythritol     1,1,1-Tris(hydroxymethyl)ethane (THE) derivatives (R = Me)
                         R = H, Me, Et

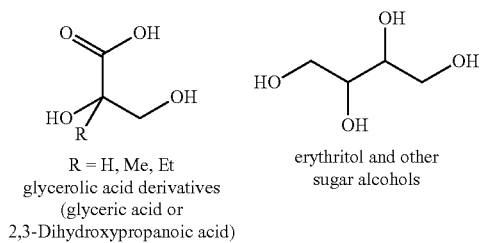

R = H, Me, Et
R = H = dihydroxy isobutyric acid R = Me = DMPA is a registered trademark of GEO Specialty Chemicals, Inc.

R = H, Me, Et
glycerolic acid derivatives (glyceric acid or 2,3-Dihydroxypropanoic acid)     erythritol and other sugar alcohols

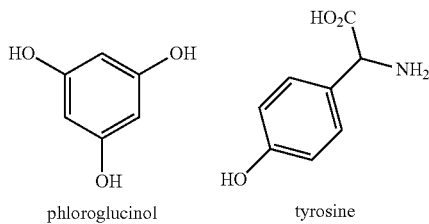

phloroglucinol     tyrosine

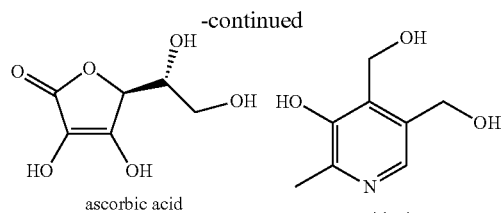

ascorbic acid     pyridoxine

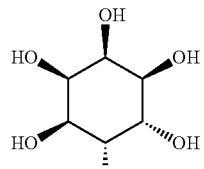 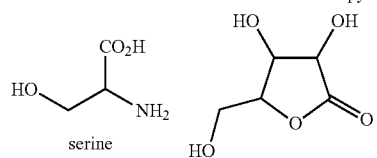

serine     ribonolactone

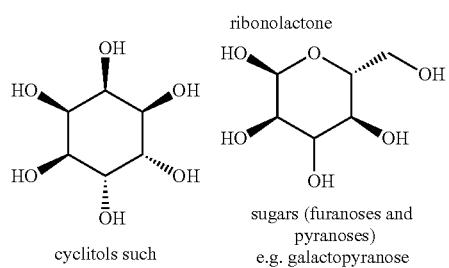

cyclitols such as inositol     sugars (furanoses and pyranoses) e.g. galactopyranose

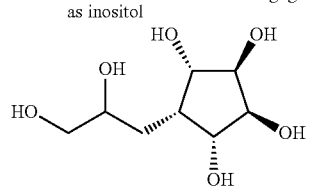

One skilled in the art would also understand that other types of polyfunctional precursor molecules, in addition to the polyhydroxy precursors shown above, may be used to form the NSAID-monomer conjugates. For example, polycarboxylic acid, polyamino, amino acid, hydroxy amino or hydroxy acid precursor molecules (where one or more of the hydroxy groups in the polyhydroxy compounds shown above are replaced with an amino group or carboxylic acid group) can be used to prepare NSAID-monomer conjugates of the invention. As an example, some polycarboxylic acid precursor molecules are as follows:

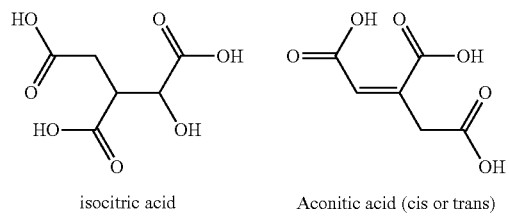

isocitric acid     Aconitic acid (cis or trans)

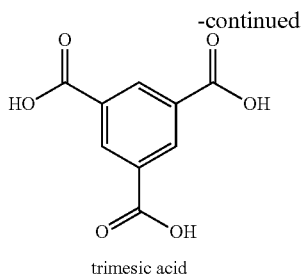

trimesic acid

Other polyfunctional precursor molecules that may be used to prepare NSAID-monomer conjugates of the invention include serine and dihydroxy isobutyric acid.

Polycarboxylic acid, polyamino, amino acid, hydroxy amino or hydroxy acid precursor molecules can be used to prepare dicarboxylic acid NSAID-monomer conjugates, diamino NSAID-monomer conjugates, amino acid NSAID-monomer conjugates, amino alcohol NSAID-monomer conjugates, or hydroxy acid NSAID-monomer conjugates, which NSAID-monomer conjugates are able to react with a suitable monomer comprising compatible chemical functionality to form polymer-NSAID conjugates of the invention.

The expression "at least one monomer comprising compatible chemical functionality" used herein typically refers to monomers comprising one or more chemical functional groups that are compatible with, and capable of undergoing reaction with a NSAID-monomer conjugate of formula (IV) during the polymerisation process.

NSAID-monomer conjugates of formula (IV) may homopolymerise, or copolymerise with one or more co-monomers. Thus, the expression "at least one monomer comprising compatible chemical functionality" refers to polymerisation of a NSAID-monomer conjugate with a monomer of the same type, or with one or more different types of co-monomers, provided that the monomer possesses compatible chemical functionality.

Homopolymerisation can occur when a NSAID-monomer conjugate of formula (IV) contains at least two different terminal reactive functional groups. For example, when $Y^1$ in formula (IV) is a hydroxy group and $Y^2$ a carboxylic acid functional group. Polymerisation of the hydroxy acid NSAID-monomer conjugate via condensation of the hydroxy and carboxylic acid functional groups therefore forms a polymer-NSAID conjugate comprising a polymer backbone with ester linkages. A polymer-NSAID conjugate comprising a polymer backbone with urethane linkages may be similarly formed by homopolymerisation of a NSAID-monomer conjugate comprising a hydroxy functional group and an isocyanate functional group.

Homopolymerisation with a ring-opening NSAID-monomer of formula (IV) can also occur after suitable initiation of the polymerisation reaction.

Copolymerisation can occur when a NSAID-monomer conjugate of formula (IV) contains two terminal reactive functional groups that are of the same type, for example, where $Y^1$ and $Y^2$ in formula (IV) are each hydroxy. Such NSAID-monomer conjugates polymerise with at least one co-monomer comprising compatible chemical functional groups capable of reacting with $Y^1$ and $Y^2$ in order to form a polymer-NSAID conjugate comprising a polymer backbone that is a copolymer.

Copolymerisation can further occur when a NSAID-monomer of formula (IV) undergoes ring-opening polymerisation in the presence of a suitable co-monomer to form polymer-NSAID conjugate comprising a polymer backbone that is a copolymer. In this instance, the co-monomer may or may not be a ring-opening monomer. Ring-opening co-monomers are generally cyclic co-monomers. The ring-opening co-monomer may comprise at least one cyclic compound selected from the group consisting of lactide, glycolide and -caprolactone.

In some embodiments, $Y^1$ and $Y^2$ in a NSAID-monomer conjugate of formula (IV) represent terminal hydroxy groups, such as shown in formula (IVh). Those skilled in the art will appreciate that hydroxy groups react with a variety of functional groups such as: isocyanate functionality to form carbamate or urethane linkages; carboxylic acid functionality to produce ester linkages; carboxylic acid halide functionality to produce ester linkages; ester functionality to produce trans-esterified ester linkages; and anhydride functionality (including cyclic anhydride groups) to produce ester linkages. The expression "compatible chemical functionality" can therefore refer to functionality or groups such as isocyanate, carboxylic acid, carboxylic acid halide, ester, amine and anhydride (including cyclic anhydride groups) groups.

Accordingly, the expression "at least one monomer comprising compatible chemical functionality" used herein typically refers to monomers comprising one or more compatible chemical functional groups selected from isocyanate, carboxylic acid, carboxylic acid halide, ester (including cyclic ester or lactone groups), anhydride (including cyclic anhydride groups), carbonate (including cyclic carbonate groups), amide (including cyclic amide or lactide groups) and amino groups, and combinations thereof. Examples of such monomers can be selected from the group consisting of a polyisocyanate, a polyol, a polyacid, a polyacid halide, a polyester, a polyanhydride, a polycarbonate, a polyamide, a polyamine, and combinations thereof. In embodiments of the invention the monomer comprising compatible functionality is selected from the group consisting of a diisocyanate, a diacid, a diacid halide, a diester (in particular, a divinyl ester), and a dianhydride.

For example, polymerisation of formula (IV) where both $Y^1$ and $Y^2$ are hydroxy groups with a diisocyanate produces a polyurethane. Such a polyurethane will typically comprise 50 mol % diol residue and 50 mol % diisocyanate residue. Where each diol monomer of formula (IV) comprises one drug moiety, the "loading" of the drug moiety in the polymer-NSAID conjugate may be designated as 50%.

In some embodiments, the present invention provides a method of preparing a polymer-NSAID conjugate according to any one of the embodiments described herein, the method comprising polymerising a NSAID-monomer of formula:

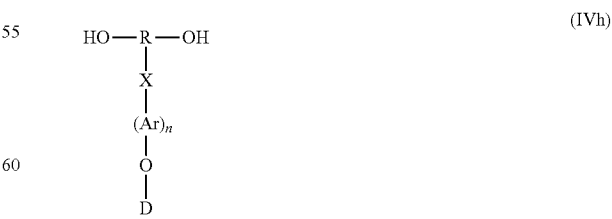

(IVh)

with monomer selected from the group consisting of: polyacid halides, polycarboxylic acids, polycarboxylic acid esters, polycarboxylic anhydrides, polyisocyanates, polyamines, cyclic esters and cyclic carbonates.

In some embodiments, the NSAID-monomer conjugate of formula (IVh) is polymerised with at least one monomer selected from the group consisting of: diacid halides, dicarboxylic acids, dicarboxylic acid esters in particular divinyl esters, dicarboxylic anhydrides, diisocyanates in particular hexamethylene diisocyanate (HDI), amino acid based diisocyanates (such as esters of lysine diisocyanate (for example ethyl ester of lysine diisocyanate (ELDI)) and divaline diisocyanate 1,3-propane diester (DVDIP)), lactones and cyclic carbonates.

Those skilled in the art will also recognise that polymerisation of a diol of formula (IV), (IVa), (IVb), (IVc), (IVd), (IVe), (IVf), (IVg) or (IVh) (where $Y^1$ and $Y^2$ are each hydroxy) with a polyisocyanate, polyacid or polyester may also take place in the presence of one or more other types of polyols, lactones or lactides (e.g. polyester polyols). In some embodiments, a diol NSAID-monomer conjugate as described herein is polymerised with a polyisocyanate and at least one co-monomer selected from the group consisting of a polyacid, a polyester and a polyester polyol. The structures of the one or more other types of polyols may or may not comprise one or more drug moieties. The polymer-NSAID conjugates so-formed may or may not have a drug loading of less than 50 mol %. For example where a diol NSAID-monomer is polymerised in the presence of an equimolar amount of polyester polyol and 2 molar equivalents of diisocyanate, the polyurethane so-formed will typically comprise the residues of the three components in the ratio of 1:1:2. Such conjugates are contemplated by the present invention. Such polymer systems may provide a useful means of modifying the physical properties of the polymer conjugates.

In forming the polymer-NSAID conjugates in accordance with the invention, the polymerisation of a NSAID-monomer conjugate of formulae described herein and a monomer comprising compatible chemical functionality can occur in a process that results in the incorporation of a hydrophilic group in the polymer-NSAID conjugate. The inclusion of a hydrophilic group can help to impart hydrophilic character to the polymer backbone structure of polymer-NSAID conjugates of the invention.

In some embodiments, in preparing polymer-NSAID conjugates of the invention, the polymerisation of a NSAID-monomer conjugate of formulae described herein and a monomer comprising compatible chemical functionality occurs in the presence of one or more hydrophilic compounds that are capable of providing a hydrophilic group.

The hydrophilic compound may be a hydrophilic co-monomer that is capable of reacting with at least one selected from the group consisting of an NSAID-monomer conjugate of formulae described herein and a monomer comprising compatible chemical functionality, to provide a hydrophilic group in the polymer-NSAID conjugate.

In some embodiments, co-monomers employed in the method for preparing polymer-NSAID conjugates of the invention comprise at least one active-hydrogen group.

In some embodiments, the polymerisation of a NSAID-monomer conjugate as described herein with a monomer comprising compatible functionality and a monomer comprising at least one active-hydrogen group results in the incorporation of a hydrophilic group in the polymer backbone of the polymer-NSAID conjugate.

In some embodiments, a NSAID-monomer conjugate as described herein is polymerised with a monomer comprising compatible functionality and a macromonomer, whereby the polymerisation results in incorporation of a hydrophilic group derived from the macromonomer in the polymer backbone of the polymer-NSAID conjugate. Macromonomers capable of providing hydrophilic groups are described herein.

In some embodiments, the macromonomer comprises a plurality of active-hydrogen groups. The active-hydrogen groups may be selected from hydroxy, amine and carboxylic acid groups, and combinations thereof.

Active-hydrogen groups, as well as monomers comprising active-hydrogen groups are described herein. Such monomers will generally contain at least one functional group capable of reacting with at least one selected from the group consisting of the monomer-NSAID conjugate of formula (IV) and the monomer comprising compatible chemical functionality. That is, the active-hydrogen group containing monomer is capable of reacting with the monomer-NSAID conjugate of formula (IV) and/or the monomer comprising compatible chemical functionality. The active-hydrogen group containing monomer may contain at least two reactive functional groups.

In some embodiments, monomers adapted to provide hydrophilic groups (such as active-hydrogen group containing monomers) comprise at least one reactive functional group selected from the group consisting of hydroxy, isocyanate, carboxylic acid, carboxylic acid halide, ester, anhydride (including cyclic anhydride groups), amide, and amino groups, and combinations thereof, and are capable of reacting with at least one selected from the group consisting of a NSAID-monomer conjugate of formula (IV) and a monomer comprising compatible chemical functionality.

Monomers employed to provide hydrophilic groups (for example, a macromonomer) are generally pre-formed, then added to the mixture of monomers used to prepare the polymer-NSAID conjugate.

In some embodiments, a monomer capable of providing a hydrophilic group (such as an active-hydrogen group containing monomer) may be added to a monomer mixture comprising a NSAID-monomer conjugate of formula (IV) (such as a diol where $Y^1$ and $Y^2$ are each hydroxy) and at least one monomer (such as a polyisocyanate, polyacid or polyester polyol) comprising compatible chemical functionality. In such instances, it is preferable that the monomer providing the hydrophilic group comprises at least two functional groups that are capable of reacting with the functional groups of the monomer comprising compatible chemical functionality to thereby incorporate a hydrophilic group into the polymer-NSAID conjugate as a part of the polymer backbone.

In one set of embodiments, reaction between an monomer-NSAID conjugate of formula (IV) and a monomer comprising compatible chemical functionality in the presence of an active-hydrogen group containing monomer results in the incorporation of a hydrophilic group in the polymer backbone.

The hydrophilic group may be incorporated in the polymer backbone of the polymer-NSAID conjugate, or it may be incorporated in a pendant group covalently bound to the polymer backbone.

In some embodiments the polymer-NSAID conjugates of the invention may be formed by polymerising a diol NSAID-monomer conjugate of formula (IV) (where $Y^1$ and $Y^2$ are each hydroxy) with a co-monomer comprising a hydrophilic polymeric or oligomeric unit and at least two terminal groups comprising compatible chemical functionality. In such instances, the terminal groups of the co-monomer are capable of reacting with the hydroxy groups in the monomer of formula (IV), resulting in the incorporation of the polymeric or oligomeric unit as a hydrophilic group into the polymer backbone of the polymer-NSAID conjugate.

In one set of embodiments, the polymeric or oligomeric unit of the co-monomer comprises at least one active hydrogen group and may comprise a plurality of active hydrogen groups.

In some embodiments of a polymer-NSAID conjugate of the invention, the polymer backbone comprises a copolymer selected from the group consisting of poly(urethane-ethers), poly(ester-ethers), poly(urethane-esters), and poly(ester-urethanes). The ether or ester component of the copolymer may provide a hydrophilic group in the polymer backbone In some embodiments the ether component may be introduced to the polymer backbone by polymerising a polyether polyol as an active-hydrogen group containing monomer (for example, a PEG macromonomer), with a NSAID-monomer conjugate of the invention and at least one monomer comprising compatible chemical functionality.

In some embodiments the ester component may be introduced to the polymer backbone by polymerising a polyester polyol as an active-hydrogen group containing monomer, with a NSAID-monomer conjugate of the invention and at least one monomer comprising compatible chemical functionality.

In some embodiments, a monomer capable of providing a hydrophilic group (such as an active-hydrogen group containing monomer) may be polymerised in situ during synthesis of the polymer-NSAID conjugate of the invention, resulting in the subsequent incorporation of a hydrophilic polymeric or oligomeric group in the polymer backbone of the conjugate.

In some embodiments the polymer-NSAID conjugates of the invention may be formed by polymerising a monomer mixture comprising a diol of formula (IVh), at least one monomer comprising compatible chemical functionality, and at least one co-monomer capable of providing a hydrophilic group. The co-monomer may be an active-hydrogen group containing monomer. The co-monomer will generally comprise reactive functional groups that are capable of reacting with the diol of formula (IVh) and/or the monomer comprising compatible chemical functionality. In this manner, the co-monomer can be incorporated in the resulting polymer-NSAID conjugate to provide a hydrophilic group in the polymer backbone of the conjugate.

The present invention also provides a method for preparing a polymer-NSAID conjugate comprising as part of its polymer backbone a moiety of general formula (II):

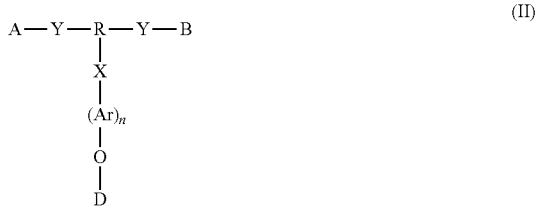

where:
A and B, which may be the same or different, each represent a biodegradable polymer backbone and are (i) attached to the —Y—R(X—(Ar)n-O-D)-Y— moiety as shown in formula (II) via a biodegradable moiety, and (ii) optionally, at least one of A and B comprises a hydrophilic group;

R comprises an optionally substituted aliphatic or an optionally substituted aryl;
Y at each occurrence is independently selected from the group consisting of —O—, —C(O)— and —NR$^a$—, where R$^a$ is H or $C_1$-$C_4$ alkyl;
X is a bond or a linking group;
Ar is an optionally substituted aryl;
D is the carboxylic acid residue of the ester formed with a substituted alkanoic acid NSAID; and
n is 0 or 1,
with the proviso then when R comprises optionally substituted aliphatic then n is 1, and when R comprises optionally substituted aryl then n is 0 or 1.
said process comprising a step of polymerising a NSAID-monomer conjugate of formula (IV):

where:
$Y^1$ and $Y^2$ each independently represent a reactive functional group, or $Y^1$ and $Y^2$ together form part of a cyclic group capable of ring-opening; and
R, X, Ar, D and n are as defined above;
with at least one monomer comprising compatible chemical functionality.

In one embodiment, a polymer-NSAID conjugate of the invention is obtained by polymerising a NSAID-monomer conjugate of formula (IV), (IVa), (IVb), (IVc), (IVd), (IVe), (IVf), (IVg) or (IVh) in the presence of at least one monomer comprising compatible chemical functionality selected from the group consisting of a polyisocyanate, a polyol, a polyacid, a polyester, a poly(ester-ether), a polyanhydride, a polyamine, and combinations thereof.

In one embodiment, a polymer-NSAID conjugate of the invention is obtained by polymerising a NSAID-monomer conjugate of formula (IV), (IVa), (IVb), (IVc), (IVd), (IVe), (IVf), (IVg) or (IVh) in the presence of a polyisocyanate and at least one selected from the group consisting of a polyacid, a polyester, a polyester polyol, a polyester hydroxy acid and a polyether polyol.

In one embodiment, a polymer-NSAID conjugate of the invention is obtained by polymerising a NSAID-monomer conjugate of formula (IV), (IVa), (IVb), (IVc), (IVd), (IVe), (IVf), (IVg) or (IVh) in the presence of a polyisocyanate and at least one selected from the group consisting of a polyester polyol, a polyester hydroxy acid, and a polyether polyol.

Polymerisation of a NSAID-monomer conjugate of formula ((IV), (IVa), (IVb), (IVc), (IVd), (IVe), (IVf), (IVg) or (IVh) in the presence of a polyisocyanate, polyacid, polyester, polyester polyol, or polyether polyol may also take place in the presence of one or more types of hydroxy acid. In this instance, the hydroxy acid may condense to form a hydroxy and/or carboxylic acid terminated ester linked macromonomer, which can react with the polyisocyanate, polyacid, polyester, polyester polyol, polyether polyol or a conjugate of formula (IV), (IVa), (IVb), (IVc), (IVd), (IVe), (IVf), (IVg) or (IVh) and be incorporated into the polymer backbone. The hydroxy acid may also be capable of reacting directly with the polyisocyanate, polyacid, polyester, polyester polyol, polyether polyol or a NSAID-monomer conjugate of formula (IV), (IVa), (IVb), (IVc), (IVd), (IVe), (IVf), (IVg) or (IVh).

Suitable polyisocyanates that may be used to prepare the polymer-NSAID conjugates include aliphatic, aromatic and cycloaliphatic polyisocyanates and combinations thereof. Specific polyisocyanates may be selected from the group consisting of m-phenylene diisocyanate, p-phenylene diisocyanate, 2,4-toluene diisocyanate, 2,6-toluene diisocyanate, 1,6-hexamethylene diisocyanate, 1,4-hexamethylene diisocyanate, 1,3-cyclohexane diisocyanate, 1,4-cyclohexane diisocyanate, hexahydro-toluene diisocyanate and its isomers, isophorone diisocyanate, dicyclo-hexylmethane diisocyanates, 1,5-napthylene diisocyanate, 4,4'-diphenylmethane diisocyanate, 2,4'diphenylmethane diisocyanate, 4,4'-biphenylene diisocyanate, 3,3'-dimethoxy-4,4'-biphenylene diisocyanate, 3,3'-dimethyl-diphenylpropane-4,4'-diisocyanate, 2,4,6-toluene triisocyanate, 4,4'-dimethyl-diphenylmethane-2,2',5,5'-tetraisocyanate, polymethylene polyphenyl polyisocyanates, divaline diisocyanate 1,3-propane diester, and alkyl esters of lysine diisocyanate (preferably ethyl ester of lysine diisocyanate) and combinations thereof. Preferred polyisocyanates include 1,6-hexamethylene diisocyanate and alkyl esters of lysine diisocyanate (preferably ethyl ester of lysine diisocyanate) and divaline diisocyanate 1,3-propane diester (DVDIP).

Suitable polyacids may be selected from the group consisting of oxalic acid, fumaric acid, maleic acid, succinic acid, glutaric acid, adipic acid, pimelic acid, suberic acid, azelaic acid, sebacic acid, phthalic acid, dodecanediacid, isophthalic acid, terephthalic acid, dodecylsuccinic acid, napthalene-2,6-dicarboxylic acid, naphthalene-2,7-dicarboxylic acid, cyclohexane dicarboxylic acid, itaconic acid, malonic acid, mesaconic acid, and combinations thereof. Preferred polyacids include maleic acid and succinic acid.

Suitable polyester polyols may be selected from the group consisting of polycaprolactone diol (PCLD), poly(DL lactide) (DLLA) and poly(lactic acid-co-glycolic acid) (PLGA), and combinations thereof.

Suitable polyether polyols may be selected from the group consisting of poly(ethylene glycol) (PEG), poly(propylene glycol), and combinations thereof.

Suitable hydroxy acids include lactic acid and glycolic acid, and combinations thereof.

Techniques, equipment and reagents well known in the art can advantageously be used to prepare the polymer-NSAID conjugates in accordance with the invention.

For example, polyurethanes might be prepared batch wise by mixing all components together and waiting until an exotherm occurs followed by casting the mixture into a container. The mixture can be subsequently heated to drive the reaction. When adopting this approach, the components to be mixed might first be made up into two parts before mixing: Part-1 might include a NSAID-monomer conjugate in accordance with the invention, a hydrophilic polymer, and one or more of: a polyol (e.g. polyester polyol), a chain extender, blowing agent (eg water), catalyst, and surfactants etc. Part-2 will generally comprise the polyisocyanate. Part-1 or Part-2 can also contain other additives such as fillers, etc.

The polyurethanes might also be prepared as a prepolymer that is subsequently reacted with a chain extender. For example, through suitable adjustment of molar ratios, an isocyanate terminated pre-polymer may be prepared by mixing Parts −1 and −2 mentioned above. The isocyanate terminated polymer could then be reacted with a chain extender/branching molecule such as a short chain diol (e.g. 1,4-butanediol) or polyol (such as a triol). Alternatively, through suitable adjustment of molar ratios, the prepolymer could be produced such that it was hydroxy terminated. This hydroxy terminated prepolymer could then be reacted with a polyisocyanate to produce the desired polyurethane.

Variables such as the choice of co-monomers and the means to produce the polymers can also assist with the production of polymer-NSAID conjugates with desirable properties For example, using polyesters such as PLGA and polyethers such as poly(ethylene glycol) may increase the hydrophilicity of the resulting conjugates. In addition, poly (ester-ethers) such as PDOO may increase the crystallinity as well as the hydrophilicity of the polymer-NSAID conjugates.

The polyurethane forming reactions can be carried out in a range of different equipment including batch kettles, static mixers, reactive injection moulders or extruders. It also may be advantageous to heat the reagents prior to or during the reaction process to improve their solubility or to enhance their reactivity. The reaction process may also be conducted in solvent.

Polyesters might be prepared batch wise by mixing all components together with heating and continued stirring. A condensate of the reaction such as water or low molecular weight alcohol (depending if acids or esters are used as the co-monomer) can be removed by distillation. To promote further reaction produce higher molecular weight polyester the temperature may be increased and vacuum applied.

A polycondensation catalyst well known to those skilled in the art can be included in the reaction mixture to increase the rate of polymerisation.

The reaction may also be conducted in an appropriate solvent to help increase the rate of polymerisation. The solvent will generally be selected to have only minimal solubility with the condensate (e.g. water or low molecular weight alcohol). For example the reaction may be carried out in toluene and a toluene/condensate mixture distilled off continuously and the condensate allowed to separate in a Dean-Stark trap.

Where the polyesters are prepared using a carboxylic acid halide monomer, those skilled in the art will appreciate that the condensation reaction is driven by the removal of HX (where X is a halide). For example, if a di-acid chloride co-monomer is reacted with the NSAID-monomer conjugate of formula (IV), HCl will be liberated from the reaction. Such a reaction may be carried out in solution at an elevated temperature to drive the reaction. It is also possible to add an appropriate base to form a salt with the liberated acid halide. For example an excess of triethyl amine may be included in a reaction mixture containing a 1:1 molar ratio of a di-acid chloride co-monomer and the NSAID-monomer conjugate of formula (IV). The reaction will afford the desired polymer-NSAID conjugate and a triethyl-amine hydrochloride salt.

With all such polycondensation reactions, it is possible to some extent to control the molecular weight of the resulting polyester, its degree of branching (through control of monomer functionality) and its end group functionality by adjustment of the molar ratio's and the functionality of the monomers used in the reaction.

In some instances it may be desirable to produce lower molecular weight polyesters that could be used as polymer-NSAID conjugate polyester polyols for reaction with polyisocyanates and perhaps other reagents for the production of polyester-urethanes.

A poly(urethane-ester) might be prepared by polymerising a diisocyanate with a hydroxy terminated polyester polyol macromer. In that case, the polyester polyol macromer will be formed from monomeric units that are coupled via a biodegradable ester moiety, and the polymerisation of it with the diisocyanate will give rise to the poly(urethane-ester) having monomeric units that are all coupled via a biodegradable urethane or ester moiety. A suitable polyester polyol may be poly(lactic acid-co-glycolic acid) (PLGA).

A poly(ester-urethane) might be prepared by polymerising an isocyanate terminated polyurethane macromer with an ester containing monomer or macromonomer. An ester containing macromonomer might be formed from the condensation of two or more hydroxy acids. In one form, the ester containing monomer is an ester linked dimer of two hydroxy acids. Suitable hydroxy acids include lactic acid, glycolic acid, and combinations thereof. The polyurethane macromer will be formed from monomeric units that are coupled via a biodegradable urethane moiety, and the polymerisation of it with the ester containing macromonomer will give rise to the poly(ester-urethane) having monomeric units that are all coupled via a biodegradable urethane or ester moiety.

Careful selection of co-monomers/reaction conditions etc may also be required for a given NSAID-monomer conjugate in order to produce a polymer conjugate with appropriate drug loading as well as have mechanical properties, bioactive release rate, formability etc.

The polymer backbone of the polymer-NSAID conjugates of the present invention may have a molecular weight of about 250 Daltons to about 6,000,000 Daltons. The molecular weight of the polymer-NSAID conjugates may be selected to suit a particular application. In the case of polymer-NSAID conjugates in the form of fibres for use in wound the molecular weight is preferably from 1000 to 200,000 Daltons. In the case of polymer-NSAID conjugates in the form of an intra-articular implant to treat osteoarthritis the molecular weight is preferably from 200,000 to 6,000,000 Daltons. The polymers of the present invention can accommodate high drug loadings, minimising the amount of material required to deliver a dose of the drug. A drug loading selected from the group consisting of at least 10% by weight, at least 20% by weight, and at least 30% by weight relative to the total weight of the polymer may be achieved.

The drug loading may also be expressed in terms of its mol % relative to the total number of moles of monomer that forms the polymer. Generally, the polymer-NSAID conjugate will comprise at least 10, at least 25, at least 35, at least 45 or up to 50 mol % of the drug, relative to the total number of moles of monomer that form the polymer.

In some embodiments, the polymer-NSAID conjugate will comprise up to 10, up to 20, up to 30, up to 40 and even up to 50 mol % of conjugated drug, relative to the total number of moles of monomer that form the polymer.

The substituted alkanoic acid NSAID is releasable from the polymer-NSAID conjugate. Generally, release of the drug will occur via a hydrolysis reaction. Hydrolysis of the aryl ester linkage under appropriate conditions allows the substituted alkanoic acid NSAID to be released from the conjugate. One skilled in the art would be able to determine appropriate conditions under which an aryl ester will hydrolyse to release the drug.

Hydrolysis of the aryl ester linkage may be influenced by the pH of the surrounding environment. For example, a more alkaline environment (pH 8.0 or higher) such as found in wound exudate may help to promote hydrolysis of the ester linkage and hence drug release.

Despite the drug being releasable from the NSAID-monomer conjugate of the invention, it will be appreciated that the intention of the present invention is for the drug to be released after the monomer has been polymerised to form polymer.

It has been found that the polymer-NSAID conjugates according to the invention are particularly useful in applications where controlled delivery of the drug is required. Accordingly, the polymer-NSAID conjugate of the invention can provide for a controlled release drug delivery system. By "controlled" release is meant that release of a dose of the drug is controlled in a manner that enables the drug to be released over a desired period of time or at a desired point in time. Controlled release may be zero order release, first order release, or delayed release of the drug.

In some embodiments, the drug may be released from the polymer-NSAID conjugate such that it provides for a sustained release drug delivery system. By "sustained" release is meant that a dose of the drug is released over a prolonged period of time, for example, over several days to weeks. This can enable a therapeutic effect to be maintained during a course of treatment over a desired period of time. This can be advantageous as it avoids the need for repeated administrations of the conjugate during the treatment.

In other embodiments, the drug may be released from the polymer-NSAID conjugate such that it provides for a rapid release drug delivery system. By "rapid" release is meant that a dose of the drug is released over a relatively short period of time, for example, over a few days. This enables a rapid initial therapeutic effect to be obtained, which can be advantageous if fast alleviation of symptoms is desired. In some embodiments the initial rapid release may be followed by more sustained release of the drug, which may enable the therapeutic effect of the drug to be maintained over a period of time.

In other embodiments, the drug may be released from the polymer-NSAID conjugate such that it provides for a delayed release drug delivery system. By "delayed" release is meant that a desired dose of the drug is not released until a period of time has elapsed, for example, a few hours, few days or few weeks. The delayed release may be followed by more sustained release of the drug. The delayed release may be useful if the polymer-NSAID conjugate is to be used in combination therapy with a complementary therapeutic agent. In such combination therapy, the complementary therapeutic agent may provide an initial rapid therapeutic effect, which may then be followed by more sustained release of a dose of drug from the conjugate. The delayed release may also be useful to provide therapy at a period of time following administration. For example, delayed release may be useful to provide for drug to be released some time after a surgical intervention.

In some embodiments, a polymer-NSAID conjugate of the invention that employs an aryl ester to conjugate the NSAID is capable of releasing the drug at a level of at least about 1 µg/mg of material/24 hours. In embodiments of the invention, the drug is released at a level of at least about 5 µg/mg of material/24 hours.

In another aspect, the present invention also provides a drug delivery system comprising a polymer-NSAID conjugate as described herein. The drug delivery system is also referred to herein as a "NSAID delivery system". The drug delivery system can facilitate administration of a substituted alkanoic acid NSAID to a subject.

The composition of the drug delivery system can have an important influence on release of the conjugated drug. To encourage drug release the drug delivery system of the invention will, in some embodiments, comprise a hydrophilic component.

The hydrophilic component may be mixed or blended with a polymer-NSAID conjugate of the invention, or it may be incorporated in the polymer-NSAID conjugate as part of the chemical structure of the conjugate. Surprisingly, it has been found that the inclusion of a hydrophilic component can aid drug release from the polymer-NSAID conjugate.

In some embodiments, the hydrophilic component may be provided by at least one selected from the group consisting of (i) the polymer-NSAID conjugate comprising at least one hydrophilic group, and (ii) at least one hydrophilic molecule in admixture with the polymer-NSAID conjugate. The drug delivery system may also comprise a combination of (i) and (ii).

In one set of embodiments, the hydrophilic component is provided by, or derived from, at least one selected from the group consisting of low molecular weight diols (preferably $C_2$-$C_4$ diols such as ethylene glycol, propane diol, propylene glycol, butane diol etc), low molecular weights triols (for example glycerol etc), low molecular weights polyols (for example sugar alcohols such as mannitol, xylitol and sorbitol etc), amino acids, amino alcohols (e.g. ethanolamine, choline, etc) lactic acid, glycolic acid, hydroxy acids (preferably hydroxybutyric acid), 1,5-dioxepan-2-one, glycerol acetate and glycerol phosphate, or combinations thereof.

In some embodiments, the hydrophilic component is at least one selected from the group consisting of poly(ethylene glycol), poly(lactic acid-co-glycolic acid) (PLGA), poly(1,5-dioxepan-2-one) (PDOO), poly(glycerol acetate) (PGAc), poly(hydroxy butyrate), poly(glycerol phosphate), an amino acid polymer, and combinations thereof. In one form of a NSAID delivery system of the invention, the hydrophilic component is poly(ethylene glycol).

The some embodiments of a NSAID delivery system, the hydrophilic component is provided by a hydrophilic group present in the polymer-NSAID conjugates of the invention. Hydrophilic groups and polymer-NSAID conjugates comprising hydrophilic groups are described herein.

When a polymer-NSAID conjugate comprises a hydrophilic group, the hydrophilic group may be incorporated in the conjugate as part of the polymer backbone structure (in-chain hydrophilic group), or it may be in a pendant group that is covalently attached to and pendant from the polymer backbone. The polymer conjugates may also comprise a combination of in-chain and pendant hydrophilic groups. The hydrophilic group may be provided by or derived from a monomer comprising at least one active-hydrogen containing group, and may comprise a oligomeric or polymeric moiety comprising a plurality of active-hydrogen groups. Active-hydrogen groups are described herein. Such polymer-drug conjugates may be incorporated in a drug delivery system of the invention to provide for controlled drug release.

In some embodiments, polymer-NSAID conjugates comprising a hydrophilic group as a part of the polymer backbone and/or in a pendant group comprise at least one oligomeric or polymeric moiety selected from the group consisting of poly(ethylene glycol), poly(lactic acid-co-glycolic acid) (PLGA), poly(1,5-dioxepan-2-one) (PDOO), poly(glycerol acetate) (PGAc), poly(hydroxy butyrate), poly(glycerol phosphate), an amino acid polymer (such as polylysine, polyglutamic acid, etc), or an amino acid oligomer, or combination of, or a copolymer of, such polymeric or oligomeric moieties.

In some embodiments, a drug delivery system of the invention comprises at least one hydrophilic molecule in admixture with the polymer-NSAID conjugate. The hydrophilic molecule may be at least one selected from the group consisting of a hydrophilic low molecular weight compound, a hydrophilic oligomer and a hydrophilic polymer. In such embodiments, the polymer-NSAID conjugate may or may not comprise a hydrophilic group as described herein.

A hydrophilic low molecular weight compound may have a molecular weight selected from the group consisting of no more than about 300 Daltons (Da), no more than about 200 Daltons (Da), and no more than about 100 Daltons (Da).

When the drug delivery system comprises a polymer-NSAID conjugate of the invention in admixture with a hydrophilic molecule, the hydrophilic molecule may be at least one selected from the group consisting of low molecular weight diols (preferably $C_2$-$C_4$ diols such as ethylene glycol, propane diol, propylene glycol, butane diol etc), low molecular weights triols (for example glycerol etc), low molecular weights polyols (for example mannitol, xylitol and sorbitol etc), amino acids, amino alcohols (for example ethanolamine, choline, etc), lactic acid, glycolic acid, hydroxy acids (preferably hydroxybutyric acid), 1,5-dioxepan-2-one, glycerol acetate and glycerol phosphate, and combinations thereof.

In one form, the drug delivery system comprises a polymer-NSAID conjugate in admixture with at least one hydrophilic polymer or hydrophilic oligomer. The hydrophilic polymer or oligomer may be derived from at least one monomer selected from the group consisting of low molecular weight diols (preferably $C_2$-$C_4$ diols such as ethylene glycol, propane diol, propylene glycol, butane diol etc), low molecular weights triols (for example glycerol etc), low molecular weights polyols (for example mannitol, xylitol and sorbitol etc), amino acids, amino alcohols (for example ethanolamine, choline, etc), lactic acid, glycolic acid, hydroxy acids (preferably hydroxybutyric acid), 1,5-dioxepan-2-one, glycerol acetate and glycerol phosphate, and combinations thereof. The hydrophilic polymer or oligomer may comprise a single type of monomeric unit. The hydrophilic polymer or oligomer may be a copolymer comprising a combination of two or more different types monomeric units derived from such monomers.

In some embodiments, the drug delivery system comprises a polymer-NSAID conjugate in admixture with at least one hydrophilic polymer selected from the group consisting of poly(ethylene glycol), poly(lactic acid-co-glycolic acid) (PLGA), poly(1,5-dioxepan-2-one) (PDOO), poly(glycerol acetate) (PGAc), poly(hydroxy butyrate), poly(glycerol phosphate), an amino acid polymer, combinations thereof, and copolymers thereof. In one set of embodiments, the hydrophilic polymer is poly(ethylene glycol).

The drug delivery system may comprise a single type of hydrophilic component, or it may comprise a combination of two or more different types of hydrophilic components. For example, the drug delivery system may comprise a single type of hydrophilic polymer, or a combination of two or more different types of hydrophilic polymer, in admixture with the polymer-NSAID conjugate.

Hydrophilic polymers incorporated in the NSAID delivery system in admixture with a polymer-NSAID conjugate may have a molecular weight in the range of from about 200 to about 15,000, preferably in the range of from about 200 to about 10,000. In a preferred embodiment, the drug delivery system comprises a polymer-NSAID conjugate of the invention in admixture with poly(ethylene glycol). The poly(ethylene glycol) preferably has a molecular weight in the range of from about 200 to about 3,000, more preferably from about 1000 to about 3000.

One advantage of the present invention is that the use of a hydrophilic component in combination with a polymer-NSAID conjugate comprising an aryl ester linked substituted alkanoic acid NSAID can help promote drug release from the polymer conjugate. Drug release from polymer-NSAID conjugate of the invention is believed to be more effective, compared to polymer-NSAID conjugates that do not employ an aryl ester linkage to conjugate the NSAID to a polymer backbone.

Without wishing to be limited by theory, it is believed that a hydrophilic component in the vicinity of the pendant drug moiety can help to facilitate drug release by attracting water molecules to the vicinity of the aryl ester linkage, thereby triggering hydrolysis of the aryl ester linkage and resulting in drug release.

In some embodiments, increased proportions of hydrophilic component may assist to enhance and/or control the rate of drug release. In this manner, the present invention can provide a further avenue for controlling drug release by modifying the quantity or relative proportion of hydrophilic component. For example, it may be possible to finely control the rate of NSAID release for an intended application by modifying the amount or relative proportion of hydrophilic component.

The composition of the hydrophilic component in the drug delivery system may also influence the release kinetics of the drug.

For instance, it has been found that drug release from polymer-NSAID conjugates of the invention can commence immediately rather than with a delay, and can proceed with zero order kinetics when the polymer conjugate is associated with poly(ethylene glycol), where the poly(ethylene glycol) is either in an admixture with the polymer-NSAID conjugate, or when it is incorporated as a hydrophilic group in the polymer-NSAID conjugate.

In some embodiments, a drug delivery system of the invention may provide for substantially zero-order release of the drug that starts immediately after administration.

Immediate release provides for the earliest possible start to treatment. Zero order release can help ensure that a steady amount of drug is released over time. In some embodiments, the polymer-NSAID conjugate of the invention provides for zero-order release of a therapeutically effective amount of the drug over a period of time of at least 5 days, at least 10 days, at least 20 days, at least 30 days, at least 60 days, or at least 90 days. A zero order release profile may be achieved even when the polymer-NSAID conjugate is fully dissolved in or miscible with the physiological medium.

Zero order release of the NSAID from a polymer-based drug delivery system is surprising, as such release kinetics is usually not observed with conventional blend technologies. Drug delivery systems prepared with conventional blend technologies often suffer from a "burst effect", where a higher than optimal dose of drug is initially released. The burst effect can be undesirable, as overdosing on the drug can result.

In other embodiments, a therapeutically effective amount of the drug can be released from the polymer-NSAID conjugate or the drug delivery system in over a relatively short period of time, typically a matter of days. In some embodiments, rapid release can be considered to be release of more than 50% of the available drug within 7 days after treatment starts.

The ability to control NSAID release is desirable in many applications. For example, some sites have a limited volume for administration of drug and require a device or drug delivery system with a high drug loading to ensure the volume of the device or system can be kept to a minimum. Despite the limited volume it is desirable to be able to deliver the drug to the site continuously and in a controlled manner over an extended period of time.

Studies of drug release from monomer-drug conjugates of general formula (IV) comprising diclofenac, ketorolac, ibuprofen or indomethacin as the conjugated NSAID have shown that the active drug (diclofenac, ketorolac, ibuprofen or indomethacin) as the main or sole drug released from the conjugate.

Studies of drug release from monomer-drug conjugates of general formula (IV) comprising the diclofenac as the conjugated NSAID have shown that a significant by-product of the hydrolysis reaction releasing the drug from the monomer-drug conjugate is a lactam having the structure illustrated below:

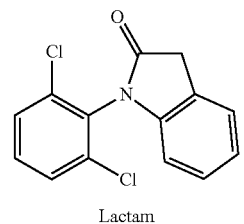

Lactam

Therefore, in releasing the drug (D) from the polymer-drug conjugate of formula (I), it might be expected that by-products such as the above lactam shown above would also formed. However, in vitro studies have found that very little lactam is released from the polymer-drug conjugate. In particular, less than 50%, preferably less than 20% and more preferably less than 10% of the released drug is in the form of the lactam.

Polymer-NSAID conjugates and drug delivery systems of the invention may be formulated in a pharmaceutical composition. In this regard, the polymer-NSAID conjugate or drug delivery system may be blended with a pharmacologically acceptable carrier. By "pharmacologically acceptable" is meant that the carrier is suitable for administration to a subject in its own right. In other words, administration of the carrier to a subject will not result in unacceptable toxicity, including allergenic responses and disease states. The term "carrier" refers to the vehicle with which the conjugate is contained prior to being administered.

In some embodiments, the carrier is a pharmaceutically acceptable solvent. A suitable pharmaceutically acceptable solvent may be an aqueous solvent, such as water.

Another suitable solvent is a non-ionic surfactant, such as polysorbate 20 or polysorbate 40. The polymer-NSAID conjugate of the invention and the drug delivery system of the invention may advantageously be soluble in the solvent.

Polymer-NSAID conjugates and drug delivery systems of the invention may be prepared in suitable forms for administration to a subject.

The form of the polymer-NSAID conjugate or the drug delivery system may be adjusted to be suited to the required application such as a coating, film, pellet, fibres, laminate, foam etc. The delivery system may in its simplest form be the conjugate provided in a desired shape, for example a rod or more intricate shape. To promote surface area contact of the conjugate with a biological environment, the conjugate may also be provided in the form of a coating on substrate, or as an article have porosity (e.g. an open cell foam).

Different physical structures can have different masses, which can result in different rates of drug release from essentially the same polymer composition.

The adjustment of the form of the polymer to suit the application and further to adjust the form to further control the drug release profile can provide an additional advantage over purely compositional and polymer structural means to control the release profile of the drug.

Polymer-NSAID conjugates and drug delivery systems in accordance with the invention or materials containing a polymer-NSAID conjugate or a drug delivery system in accordance with the invention can be formed into an article or device. The article or device may be fabricated in a range of forms. Suitably, the article or device is a medical device. The polymer-drug conjugates in accordance with the invention can also be incorporated or made into coatings for target in vitro and in vivo applications.

Implantable articles or devices comprising a polymer-NSAID conjugate of the invention or a drug delivery system of the invention desirably have material properties that ensure the subject does not experience any discomfort after the article or device is implanted.

For example, administration of a solid implant inside the synovium of a load bearing joint is likely to damage joint cartilage. In such applications, the implant may desirably be in a liquid or semi-solid state or rapidly dissolve after administration, yet still provide control over NSAID delivery.

In some embodiments, the medical device can be suitably shaped to facilitate delivery to the eye. One such device is a rod-shaped implant able to be housed within the lumen of a 20 to 30 gauge needle. The outer diameter of the implant would be less than 0.5 mm, preferably about 0.4 mm and more preferably 0.3 mm. The length of the implant can be selected to deliver the required dose of drug.

The resultant implant could be a solid, a semi-solid or even a gel. A solid implant would comprise material with a glass transition temperature (as measured by differential scanning calorimetry) above 37° C., a semi-solid would have a glass transition temperature at or just below 25-37° C. A gel could be formed by appropriate formulation of the drug-polymer conjugate or the drug delivery system with an appropriate plasticiser. Alternatively, the resultant implant could be a liquid at room temperature (25° C.) temperature and form a gel immediately after administration, such as a thermoset gel that is a liquid at room temperature but forms a gel at 37° C.

The rod-shaped implant can be of a number of different structural forms. Firstly the rod-shaped implant can consist solely of the polymer-NSAID conjugate or as a blend with an appropriate polymer (for example PEG, PGLA or a degradable polyurethane).

Another possibility is to make the rod-shaped implant as a bi-component structure where the polymer-NSAID conjugate or the drug delivery system can either be incorporated in the outer or inner layers. Incorporating the polymer-NSAID conjugate or the drug delivery system in the outer layer could be done to give a measured dose. Additionally the inner layer biodegradable polymer could be to provide structural integrity to allow the delivery via the needle. Additionally the inner polymer could be designed to degrade either faster or slower than the polymer-NSAID conjugate or drug delivery system layer. This could be to alter the rate of biodegradation or the implant.

In some embodiments, the medical device is suitably a topical product. In specific embodiments, the topical product is a wound dressing. Wound dressings may be in the form of a woven or non-woven mat. In some embodiments, the wound dressing consists of or comprises fibres formed from or comprising the polymer-NSAID conjugates of the invention. Fibre based structures can in turn be knitted, woven, spun bonded or formed into non-woven mats etc. Additionally, fibre structures could be formed with a binder resin into composite structures. The fibres could be formed by melt extrusion, wet spinning or the polymer-NSAID conjugate could be over-coated or dispersed within fibres by bi-component fibre extrusion, dip or spray coating etc. Other suitable procedures for forming wound dressings has been described by T. N. Yudanova and I. V. Reshetov in "Modern Wound Dressings: Manufacturing and Properties", *Pharmaceutical Chemistry Journal*, 2006, vol 40 (2), 85-92.

Possible means for producing the rods or fibres described above include:
  Melt extrusion of the polymer-NSAID conjugate or a drug delivery system or a material containing the polymer-NSAID conjugate through an appropriate die.
  Simultaneous bi-component extrusion of the polymer-NSAID conjugate and other materials forming the outer or inner layers through an appropriate die.
  Sequential overcoating extrusion of one polymer later with another. For example a core polymer fibre of PLGA could be melt overcoated with a polymer containing the drug polymer conjugate.
  It is also possible to coat an appropriate inner polymer carrier material (e.g. PLGA) with a liquid or solid form of the polymer-NSAID conjugate or the drug delivery system.

In some embodiments, fibres formed from or comprising the polymer-NSAID conjugates of the invention can be woven into a bandage or other wound care product. Fibres may also be incorporated as an additional component of continuous film bandages. Bandages or wound care products comprising such fibres are then able to be applied to wounds where they may act to absorb moisture from the wound exudate. The absorbed moisture can initiate hydrolysis of the aryl ester linkage conjugating the drug moiety to the polymer backbone of the conjugates of the invention and thereby trigger release of the NSAID at the wound site. The present invention may therefore have particular benefit to wound applications.

Hydrolysis of the aryl ester linkage conjugating the NSAID to the polymer backbone of the polymer-conjugates of the invention can be influenced by pH. As a result, one benefit of the invention is that release of the NSAID may be controlled by the pH of the local environment. A wound exudate generally has a high pH (typically pH 8.0 to 9.0), compared to normal physiological pH (pH 7.4). The application of a bandage or other wound care product comprising a polymer-NSAID conjugate or a drug delivery system of the invention to a wound may therefore provide benefits in terms of higher drug release while the wound is active. As the wound heals, the pH of the exudate decreases. As a result, polymer-NSAID conjugates and drug delivery systems of the present invention may be used to prepare wound-responsive bandages and other wound care products, which release higher amounts of drug while the wound is active and less of the drug as the wound begins to heal.

Accordingly, another aspect of the present invention provides use of a polymer-NSAID conjugate or a drug delivery system as described herein in the manufacture of a wound care product for the treatment of a wound in a subject. In some embodiments, the wound care product is a wound dressing. Examples of wound dressings include absorptive wound dressings and foam wound dressings.

The present invention also provides a method for treating a wound in a subject, the method comprising the step of applying a wound care product comprising a polymer-NSAID conjugate or a drug delivery system as described herein to the wound. In some embodiments, the wound care product is a wound dressing. Examples of wound dressings include absorptive wound dressings and foam wound dressings.

A pharmaceutical composition comprising polymer-NSAID conjugates and drug delivery systems of the invention may be formulated in a pharmaceutical composition for the treatement of osteo-arthritis (OA). OA affects all joints of the body but in particular load-bearing joints such as the knee, hip or ankle. To deliver an NSAID directly to such a joint with conventional sustained release technologies would require the use of a solid implant. Solid implants cannot be administered to a load bearing joint because of the risk of cartilage damage. Polymer-NSAID conjugates and drug delivery systems of the invention are soluble in physiological medium or can form a substance having a gel-like state in physiological medium. As a result, the present invention can address one or more problems associated with conventional treatments by allowing sustained release of a NSAID from a soluble, liquid, gel or semi-solid NSAID-polymer conjugate.

Accordingly, polymer-NSAID conjugates and drug delivery systems of the invention may be formulated in a composition for intra-articular delivery. Such compositions may be injected at the desired site of delivery. Suitable compositions may be in the form of a liquid or an injectable gel.

In one form of the invention the polymer-NSAID conjugate or drug delivery system may be formulated as a liquid. The liquid may be in a form that is suitable for administration by injection to a desired site of treatment. The liquid may comprise from 1% and up to 100% by weight of polymer-NSAID conjugate. In some embodiments, the polymer-NSAID conjugate or NSAID delivery system may be in liquid form at temperatures above room temperature or a solid at room temperature and liquid at physiological temperature (in humans approximately 37° C.). The substituted alkanoic acid NSAID is therefore releasable from the liquid polymer-NSAID conjugate. The liquid or solid form of the polymer-NSAID conjugate may be capable of being dissolved in the physiological medium.

Accordingly, another aspect of the present invention provides use of a polymer-NSAID conjugate or a drug delivery system as described herein in the manufacture of a medicament for the treatment of osteo-arthritis in a subject. In embodiments of the invention, the medicament is in an injectable form.

The present invention also provides a method for treating osteo-arthritis in a subject, the method comprising the step of administering a medicament comprising a polymer-NSAID conjugate or a drug delivery system as described herein to an intra-articular joint of the subject. In embodiments of the invention, the medicament is in an injectable form.

In this specification "optionally substituted" is taken to mean that a group may or may not be substituted or fused (so as to form a condensed polycyclic group) with one, two, three or more of organic and inorganic groups (i.e. the optional substituent) including those selected from: alkyl, alkenyl, alkynyl, carbocyclyl, aryl, heterocyclyl, heteroaryl, acyl, aralkyl, alkaryl, alkheterocyclyl, alkheteroaryl, alkcarbocyclyl, halo, haloalkyl, haloalkenyl, haloalkynyl, haloaryl, halocarbocyclyl, haloheterocyclyl, haloheteroaryl, haloacyl, haloarylalkyl, hydroxy, hydroxyalkyl, hydroxyalkenyl, hydroxyalkynyl, hydroxycarbocyclyl, hydroxyaryl, hydroxyheterocyclyl, hydroxyheteroaryl, hydroxyacyl, hydroxyaralkyl, alkoxyalkyl, alkoxyalkenyl, alkoxyalkynyl, alkoxycarbocyclyl, alkoxyaryl, alkoxyheterocyclyl, alkoxyheteroaryl, alkoxyacyl, alkoxyaralkyl, alkoxy, alkenyloxy, alkynyloxy, aryloxy, carbocyclyloxy, aralkyloxy, heteroaryloxy, heterocyclyloxy, acyloxy, haloalkoxy, haloalkenyloxy, haloalkynyloxy, haloaryloxy, halocarbocyclyloxy, haloaralkyloxy, haloheteroaryloxy, haloheterocyclyloxy, haloacyloxy, nitro, nitroalkyl, nitroalkenyl, nitroalkynyl, nitroaryl, nitroheterocyclyl, nitroheteroayl, nitrocarbocyclyl, nitroacyl, nitroaralkyl, amino ($NH_2$), alkylamino, dialkylamino, alkenylamino, alkynylamino, arylamino, diarylamino, aralkylamino, diaralkylamino, acylamino, diacylamino, heterocyclamino, heteroarylamino, carboxy, carboxyester, amido, alkylsulphonyloxy, arylsulphenyloxy, alkylsulphenyl, arylsulphenyl, thio, alkylthio, alkenylthio, alkynylthio, arylthio, aralkylthio, carbocyclylthio, heterocyclylthio, heteroarylthio, acylthio, sulfoxide, sulfonyl, sulfonamide, aminoalkyl, aminoalkenyl, aminoalkynyl, aminocarbocyclyl, aminoaryl, aminoheterocyclyl, aminoheteroaryl, aminoacyl, aminoaralkyl, thioalkyl, thioalkenyl, thioalkynyl, thiocarbocyclyl, thioaryl, thioheterocyclyl, thioheteroaryl, thioacyl, thioaralkyl, carboxyalkyl, carboxyalkenyl, carboxyalkynyl, carboxycarbocyclyl, carboxyaryl, carboxyheterocyclyl, carboxyheteroaryl, carboxyacyl, carboxyaralkyl, carboxyesteralkyl, carboxyesteralkenyl, carboxyesteralkynyl, carboxyestercarbocyclyl, carboxyesteraryl, carboxyesterheterocyclyl, carboxyesterheteroaryl, carboxyesteracyl, carboxyesteraralkyl, amidoalkyl, amidoalkenyl, amidoalkynyl, amidocarbocyclyl, amidoaryl, amidoheterocyclyl, amidoheteroaryl, amidoacyl, amidoaralkyl, formylalkyl, formylalkenyl, formylalkynyl, formylcarbocyclyl, formylaryl, formylheterocyclyl, formylheteroaryl, formylacyl, formylaralkyl, acylalkyl, acylalkenyl, acylalkynyl, acylcarbocyclyl, acylaryl, acylheterocyclyl, acylheteroaryl, acylacyl, acylaralkyl, sulfoxidealkyl, sulfoxidealkenyl, sulfoxidealkynyl, sulfoxidecarbocyclyl, sulfoxidearyl, sulfoxideheterocyclyl, sulfoxideheteroaryl, sulfoxideacyl, sulfoxidearalkyl, sulfonylalkyl, sulfonylalkenyl, sulfonylalkynyl, sulfonylcarbocyclyl, sulfonylaryl, sulfonylheterocyclyl, sulfonylheteroaryl, sulfonylacyl, sulfonylaralkyl, sulfonamidoalkyl, sulfonamidoalkenyl, sulfonamidoalkynyl, sulfonamidocarbocyclyl, sulfonamidoaryl, sulfonamidoheterocyclyl, sulfonamidoheteroaryl, sulfonamidoacyl, sulfonamidoaralkyl, nitroalkyl, nitroalkenyl, nitroalkynyl, nitrocarbocyclyl, nitroaryl, nitroheterocyclyl, nitroheteroaryl, nitroacyl, nitroaralkyl, cyano, sulfate and phosphate groups.

In some embodiments, it may be desirable that a group (for example the R group) is optionally substituted with a polymer chain. An example of such a polymer chain includes a polyester, polyurethane, or copolymers thereof. Such a polymer chain may, or may not, have one or more drugs appended thereto. For example, the R group of the formulae disclosed herein may be substituted with a polymer chain. The skilled worker will recognise that the R group may therefore represent a point of branching of the polymer backbone within the drug polymer conjugate of the present invention. If R is substituted with a polymer chain, that polymer chain should also be bioerodible and not contain any repeat units that are coupled with a non-bioerodible moiety as described herein.

Preferred optional substituents include the aforementioned reactive functional groups or moieties, polymer chains and alkyl, (e.g. $C_{1-6}$ alkyl such as methyl, ethyl, propyl, butyl, cyclopropyl, cyclobutyl, cyclopentyl or cyclohexyl), hydroxyalkyl (e.g. hydroxymethyl, hydroxyethyl, hydroxypropyl), alkoxyalkyl (e.g. methoxymethyl, methoxyethyl, methoxypropyl, ethoxymethyl, ethoxyethyl, ethoxypropyl etc) alkoxy (e.g. $C_{1-6}$ alkoxy such as methoxy, ethoxy, propoxy, butoxy, cyclopropoxy, cyclobutoxy), halo, trifluoromethyl, trichloromethyl, tribromomethyl, hydroxy, phenyl (which itself may be further substituted e.g., by $C_{1-6}$ alkyl, halo, hydroxy, hydroxy$C_{1-6}$ alkyl, $C_{1-6}$ alkoxy, halo$C_{1-6}$ alkyl, cyano, nitro $OC(O)C_{1-6}$ alkyl, and amino), benzyl (wherein benzyl itself may be further substituted e.g., by $C_{1-6}$ alkyl, halo, hydroxy, hydroxy$C_{1-6}$alkyl, $C_{1-6}$ alkoxy, halo$C_{1-6}$ alkyl, cyano, nitro $OC(O)C_{1-6}$ alkyl, and amino), phenoxy (wherein phenyl itself may be further substituted e.g., by $C_{1-6}$ alkyl, halo, hydroxy, hydroxy$C_{1-6}$ alkyl, $C_{1-6}$ alkoxy, halo$C_{1-6}$ alkyl, cyano, nitro $OC(O)C_{1-6}$ alkyl, and amino), benzyloxy (wherein benzyl itself may be further substituted e.g., by $C_{1-6}$ alkyl, halo, hydroxy, hydroxy$C_{1-6}$ alkyl, $C_{1-6}$ alkoxy, halo$C_{1-6}$ alkyl, cyano, nitro $OC(O)C_{1-6}$ alkyl, and amino), amino, alkylamino (e.g. $C_{1-6}$ alkyl, such as methylamino, ethylamino, propylamino etc), dialkylamino (e.g. $C_{1-6}$ alkyl, such as dimethylamino, diethylamino, dipropylamino), acylamino (e.g. $NHC(O)CH_3$), phenylamino (wherein phenyl itself may be further substituted e.g., by $C_{1-6}$ alkyl, halo, hydroxy hydroxy$C_{1-6}$ alkyl, $C_{1-6}$ alkoxy, halo$C_{1-6}$ alkyl, cyano, nitro $OC(O)C_{1-6}$ alkyl, and amino), nitro, formyl, —C(O)-alkyl (e.g. $C_{1-6}$ alkyl, such as acetyl), O—C(O)-alkyl (e.g. $C_{1-6}$alkyl, such as acetyloxy), benzoyl (wherein the phenyl group itself may be further substituted e.g., by $C_{1-6}$ alkyl, halo, hydroxy hydroxy$C_{1-6}$ alkyl, $C_{1-6}$ alkoxy, halo$C_{1-6}$ alkyl, cyano, nitro $OC(O)C_{1-6}$ alkyl, and amino), replacement of $CH_2$ with C=O, $CO_2H$, $CO_2$alkyl (e.g. $C_{1-6}$ alkyl such as methyl ester, ethyl ester, propyl ester, butyl ester), $CO_2$phenyl (wherein phenyl itself may be further substituted e.g., by $C_{1-6}$ alkyl, halo, hydroxy, hydroxy $C_{1-6}$ alkyl, $C_{1-6}$ alkoxy, halo $C_{1-6}$ alkyl, cyano, nitro $OC(O)C_{1-6}$ alkyl, and amino), $CONH_2$, CONHphenyl (wherein phenyl itself may be further substituted e.g., by $C_{1-6}$ alkyl, halo, hydroxy, hydroxy $C_{1-6}$ alkyl, $C_{1-6}$ alkoxy, halo $C_{1-6}$ alkyl, cyano, nitro $OC(O)C_{1-6}$ alkyl, and amino), CONHbenzyl (wherein benzyl itself may be further substituted e.g., by $C_{1-6}$ alkyl, halo, hydroxy hydroxy $C_{1-6}$ alkyl, $C_{1-6}$ alkoxy, halo $C_{1-6}$ alkyl, cyano, nitro $OC(O)C_{1-6}$ alkyl, and amino), CONHalkyl (e.g. $C_{1-6}$ alkyl such as methyl ester, ethyl ester, propyl ester, butyl amide) CONHdialkyl (e.g. $C_{1-6}$ alkyl)aminoalkyl (e.g., HN $C_{1-6}$ alkyl-, $C_{1-6}$alkylHN—$O_{1-6}$ alkyl- and $(C_{1-6}$ alkyl$)_2$N—$O_{1-6}$ alkyl-), thioalkyl (e.g., HS $C_{1-6}$ alkyl-), carboxyalkyl (e.g., $HO_2CC_{1-6}$ alkyl-), carboxyesteralkyl (e.g., $C_{1-6}$ alkyl$O_2CC_{1-6}$ alkyl-), amidoalkyl (e.g., $H_2N(O)CC_{1-6}$ alkyl-, $H(C_{1-6}$ alkyl)N(O)$CC_{1-6}$ alkyl-), formylalkyl (e.g., $OHCC_{1-6}$alkyl-), acylalkyl (e.g., $C_{1-6}$ alkyl(O)$CC_{1-6}$ alkyl-), nitroalkyl (e.g., $O_2NC_{1-6}$ alkyl-), sulfoxidealkyl (e.g., $R^3(O)SC_{1-6}$ alkyl, such as $C_{1-6}$ alkyl(O)$SC_{1-6}$ alkyl-), sulfonylalkyl (e.g., $R^3(O)_2SC_{1-6}$ alkyl—such as $C_{1-6}$ alkyl(O)$_2SC_{1-6}$ alkyl-), sulfonamidoalkyl (e.g., $_2$HRN(O)$SC_{1-6}$ alkyl, $H(C_{1-6}$alkyl)N(O)$SC_{1-6}$alkyl-).

As used herein, the term "aliphatic", used either alone or in compound words denotes straight chain saturated and unsaturated hydrocarbyl. Examples of aliphatic groups include alkanes, alkenes, and alkynes.

As used herein, the term "alicyclic", used either alone or in compound words denotes cyclic non-aromatic hydrocarbyl. An example of an alicyclic group is cyclohexane.

As used herein, the term "alkyl", used either alone or in compound words denotes straight chain, branched or cyclic alkyl, for example $C_{1-40}$ alkyl, or $C_{1-20}$ or $C_{1-10}$ Examples of straight chain and branched alkyl include methyl, ethyl, n-propyl, isopropyl, n-butyl, sec-butyl, t-butyl, n-pentyl, 1,2-dimethylpropyl, 1,1-dimethyl-propyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, heptyl, 5-methylhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethyl-pentyl, 1,2,3-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5-, 6- or 7-methyloctyl, 1-, 2-, 3-, 4- or 5-ethylheptyl, 1-, 2- or 3-propylhexyl, decyl, 1-, 2-, 3-, 4-, 5-, 6-, 7- and 8-methylnonyl, 1-, 2-, 3-, 4-, 5- or 6-ethyloctyl, 1-, 2-, 3- or 4-propylheptyl, undecyl, 1-, 2-, 3-, 4-, 5-, 6-, 7-, 8- or 9-methyldecyl, 1-, 2-, 3-, 4-, 5-, 6- or 7-ethylnonyl, 1-, 2-, 3-, 4- or 5-propyloctyl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1-2-pentylheptyl, tridecyl, tetradecyl, pentadecyl, hexadecyl, heptadecyl, octadecyl, nonoadecyl, eicosyl and the like. Examples of cyclic alkyl include mono- or polycyclic alkyl groups such as cyclopropyl, cyclobutyl, cyclopentyl, cyclohexyl, cycloheptyl, cyclooctyl, cyclononyl, cyclodecyl and the like. Where an alkyl group is referred to generally as "propyl", butyl" etc, it will be understood that this can refer to any of straight, branched and cyclic isomers where appropriate. An alkyl group may be optionally substituted by one or more optional substituents as herein defined.

As used herein, term "alkenyl" denotes groups formed from straight chain, branched or cyclic hydrocarbon residues containing at least one carbon to carbon double bond including ethylenically mono-, di- or polyunsaturated alkyl or cycloalkyl groups as previously defined, for example $C_{2-40}$ alkenyl, or $C_{2-20}$ or $C_{2-10}$. Thus, alkenyl is intended to include propenyl, butylenyl, pentenyl, hexaenyl, heptaenyl, octaenyl, nonaenyl, decenyl, undecenyl, dodecenyl, tridecenyl, tetradecenyl, pentadecenyl, hexadecenyl, heptadecenyl, octadecenyl, nondecenyl, eicosenyl hydrocarbon groups with one or more carbon to carbon double bonds. Examples of alkenyl include vinyl, allyl, 1-methylvinyl, butenyl, isobutenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1,4-pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl and 1,3,5,7-cyclooctatetraenyl. An alkenyl group may be optionally substituted by one or more optional substituents as herein defined.

As used herein the term "alkynyl" denotes groups formed from straight chain, branched or cyclic hydrocarbon residues containing at least one carbon-carbon triple bond including ethylenically mono-, di- or polyunsaturated alkyl or cycloalkyl groups as previously defined, for example, $C_{2-40}$ alkenyl, or $C_{2-20}$ or $C_{2-10}$. Thus, alkynyl is intended to include propynyl, butylynyl, pentynyl, hexaynyl, heptaynyl, octaynyl, nonaynyl, decynyl, undecynyl, dodecynyl, tridecynyl, tetradecynyl, pentadecynyl, hexadecynyl, heptadecynyl, octadecynyl, nondecynyl, eicosynyl hydrocarbon groups with one or more carbon to carbon triple bonds.

Examples of alkynyl include ethynyl, 1-propynyl, 2-propynyl, and butynyl isomers, and pentynyl isomers. An alkynyl group may be optionally substituted by one or more optional substituents as herein defined.

An alkenyl group may comprise a carbon to carbon triple bond and an alkynyl group may comprise a carbon to carbon double bond (i.e. so called ene-yne or yne-ene groups).

As used herein, the term "aryl" (or "carboaryl") denotes any of single, polynuclear, conjugated and fused residues of aromatic hydrocarbon ring systems. Examples of aryl include phenyl, biphenyl, terphenyl, quaterphenyl, naphthyl, tetrahydronaphthyl, anthracenyl, dihydroanthracenyl, benzanthracenyl, dibenzanthracenyl, phenanthrenyl, fluorenyl, pyrenyl, idenyl, azulenyl, chrysenyl. Preferred aryl include phenyl and naphthyl. An aryl group may be optionally substituted by one or more optional substituents as herein defined.

As used herein, the terms "alkylene", "alkenylene", and "arylene" are intended to denote the divalent forms of "alkyl", "alkenyl", and "aryl", respectively, as herein defined.

The term "halogen" ("halo") denotes fluorine, chlorine, bromine or iodine (fluoro, chloro, bromo or iodo). Preferred halogens are chlorine, bromine or iodine.

The term "carbocyclyl" includes any of non-aromatic monocyclic, polycyclic, fused or conjugated hydrocarbon residues, preferably $C_{3-20}$ (e.g. $C_{3-10}$ or $C_{3-8}$). The rings may be saturated, e.g. cycloalkyl, or may possess one or more double bonds (cycloalkenyl) and/or one or more triple bonds (cycloalkynyl). Particularly preferred carbocyclyl moieties are 5-6-membered or 9-10 membered ring systems. Suitable examples include cyclopropyl, cyclobutyl, cyclopentyl, cyclohexyl, cycloheptyl, cyclooctyl, cyclononyl, cyclodecyl, cyclopentenyl, cyclohexenyl, cyclooctenyl, cyclopentadienyl, cyclohexadienyl, cyclooctatetraenyl, indanyl, decalinyl and indenyl.

The term "heterocyclyl" when used alone or in compound words includes any of monocyclic, polycyclic, fused or conjugated hydrocarbon residues, preferably $C_{3-20}$ (e.g. $C_{3-10}$ or $C_{3-8}$) wherein one or more carbon atoms are replaced by a heteroatom so as to provide a non-aromatic residue. Suitable heteroatoms include O, N, S, P and Se, particularly O, N and S. Where two or more carbon atoms are replaced, this may be by two or more of the same heteroatom or by different heteroatoms. The heterocyclyl group may be saturated or partially unsaturated, i.e. possess one or more double bonds. Particularly preferred heterocyclyl are 5-6 and 9-10 membered heterocyclyl. Suitable examples of heterocyclyl groups may include azridinyl, oxiranyl, thiiranyl, azetidinyl, oxetanyl, thietanyl, 2H-pyrrolyl, pyrrolidinyl, pyrrolinyl, piperidyl, piperazinyl, morpholinyl, indolinyl, imidazolidinyl, imidazolinyl, pyrazolidinyl, thiomorpholinyl, dioxanyl, tetrahydrofuranyl, tetrahydropyranyl, tetrahydropyrrolyl, tetrahydrothiophenyl, pyrazolinyl, dioxalanyl, thiazolidinyl, isoxazolidinyl, dihydropyranyl, oxazinyl, thiazinyl, thiomorpholinyl, oxathianyl, dithianyl, trioxanyl, thiadiazinyl, dithiazinyl, trithianyl, azepinyl, oxepinyl, thiepinyl, indenyl, indanyl, 3H-indolyl, isoindolinyl, 4H-quinolazinyl, chromenyl, chromanyl, isochromanyl, pyranyl and dihydropyranyl.

The term "heteroaryl" includes any of monocyclic, polycyclic, fused or conjugated hydrocarbon residues, wherein one or more carbon atoms are replaced by a heteroatom so as to provide an aromatic residue. Preferred heteroaryl have 3-20 ring atoms, e.g. 3-10. Particularly preferred heteroaryl are 5-6 and 9-10 membered bicyclic ring systems. Suitable heteroatoms include, O, N, S, P and Se, particularly O, N and S. Where two or more carbon atoms are replaced, this may be by two or more of the same heteroatom or by different heteroatoms. Suitable examples of heteroaryl groups may include pyridyl, pyrrolyl, thienyl, imidazolyl, furanyl, benzothienyl, isobenzothienyl, benzofuranyl, isobenzofuranyl, indolyl, isoindolyl, pyrazolyl, pyrazinyl, pyrimidinyl, pyridazinyl, indolizinyl, quinolyl, isoquinolyl, phthalazinyl, 1,5-naphthyridinyl, quinozalinyl, quinazolinyl, quinolinyl, oxazolyl, thiazolyl, isothiazolyl, isoxazolyl, triazolyl, oxadialzolyl, oxatriazolyl, triazinyl, and furazanyl.

The term "acyl" either alone or in compound words denotes a group containing the agent C=O (and not being a carboxylic acid, ester or amide) Preferred acyl includes $C(O)-R^x$, wherein $R^x$ is hydrogen or an alkyl, alkenyl, alkynyl, aryl, heteroaryl, carbocyclyl, or heterocyclyl residue. Examples of acyl include formyl, straight chain or branched alkanoyl (e.g. $C_{1-20}$) such as, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl and icosanoyl; cycloalkylcarbonyl such as cyclopropylcarbonyl cyclobutylcarbonyl, cyclopentylcarbonyl and cyclohexylcarbonyl; aroyl such as benzoyl, toluoyl and naphthoyl; aralkanoyl such as phenylalkanoyl (e.g. phenylacetyl, phenylpropanoyl, phenylbutanoyl, phenylisobutylyl, phenylpentanoyl and phenylhexanoyl) and naphthylalkanoyl (e.g. naphthylacetyl, naphthylpropanoyl and naphthylbutanoyl]; aralkenoyl such as phenylalkenoyl (e.g. phenylpropenoyl, phenylbutenoyl, phenylmethacryloyl, phenylpentenoyl and phenylhexenoyl and naphthylalkenoyl (e.g. naphthylpropenoyl, naphthylbutenoyl and naphthylpentenoyl); aryloxyalkanoyl such as phenoxyacetyl and phenoxypropionyl; arylthiocarbamoyl such as phenylthiocarbamoyl; arylglyoxyloyl such as phenylglyoxyloyl and naphthylglyoxyloyl; arylsulfonyl such as phenylsulfonyl and napthylsulfonyl; heterocycliccarbonyl; heterocyclicalkanoyl such as thienylacetyl, thienylpropanoyl, thienylbutanoyl, thienylpentanoyl, thienylhexanoyl, thiazolylacetyl, thiadiazolylacetyl and tetrazolylacetyl; heterocyclicalkenoyl such as heterocyclicpropenoyl, heterocyclicbutenoyl, heterocyclicpentenoyl and heterocyclichexenoyl; and heterocyclicglyoxyloyl such as thiazolyglyoxyloyl and thienylglyoxyloyl. The $R^x$ residue may be optionally substituted as described herein.

The term "sulfoxide", either alone or in a compound word, refers to a group $-S(O)R^y$ wherein $R^y$ is selected from hydrogen, alkyl, alkenyl, alkynyl, aryl, heteroaryl, heterocyclyl, carbocyclyl, and aralkyl. Examples of preferred $R^y$ include $C_{1-20}$alkyl, phenyl and benzyl.

The term "sulfonyl", either alone or in a compound word, refers to a group $S(O)_2-R^y$, wherein $R^y$ is selected from hydrogen, alkyl, alkenyl, alkynyl, aryl, heteroaryl, heterocyclyl, carbocyclyl and aralkyl. Examples of preferred $R^y$ include $C_{1-20}$alkyl, phenyl and benzyl.

The term "sulfonamide", either alone or in a compound word, refers to a group $S(O)NR^yR^y$ wherein each $R^y$ is independently selected from hydrogen, alkyl, alkenyl, alkynyl, aryl, heteroaryl, heterocyclyl, carbocyclyl, and aralkyl. Examples of preferred $R^y$ include $C_{1-20}$alkyl, phenyl and benzyl. In a preferred embodiment at least one $R^y$ is hydrogen. In another form, both $R^y$ are hydrogen.

The term, "amino" is used here in its broadest sense as understood in the art and includes groups of the formula $NR^AR^B$ wherein $R^A$ and $R^B$ may be any independently selected from hydrogen, alkyl, alkenyl, alkynyl, aryl, carbocyclyl, heteroaryl, heterocyclyl, aralkyl, and acyl. $R^A$ and $R^B$, together with the nitrogen to which they are attached, may also form a monocyclic, or polycyclic ring system e.g. a 3-10 membered ring, particularly, 5-6 and 9-10 membered systems. Examples of "amino" include $NH_2$, NHalkyl (e.g. $C_{1-20}$alkyl), NHaryl (e.g. NHphenyl), NHaralkyl (e.g. NHbenzyl), NHacyl (e.g. NHC(O)$C_{1-20}$alkyl, NHC(O)phenyl), Nalkylalkyl (wherein each alkyl, for example $C_{1-20}$, may be the same or different) and 5 or 6 membered rings, optionally containing one or more same or different heteroatoms (e.g. O, N and S).

The term "amido" is used here in its broadest sense as understood in the art and includes groups having the formula C(O)NR$^A$R$^B$, wherein $R^A$ and $R^B$ are as defined as above. Examples of amido include C(O)$NH_2$, C(O)NHalkyl (e.g. $C_{1-20}$alkyl), C(O)NHaryl (e.g. C(O)NHphenyl), C(O)NHaralkyl (e.g. C(O)NHbenzyl), C(O)NHacyl (e.g. C(O)NHC(O)$C_{1-20}$alkyl, C(O)NHC(O)phenyl), C(O)Nalkylalkyl (wherein each alkyl, for example $C_{1-20}$, may be the same or different) and 5 or 6 membered rings, optionally containing one or more same or different heteroatoms (e.g. O, N and S).

The term "carboxy ester" is used here in its broadest sense as understood in the art and includes groups having the formula $CO_2R^z$, wherein $R^z$ may be selected from groups including alkyl, alkenyl, alkynyl, aryl, carbocyclyl, heteroaryl, heterocyclyl, aralkyl, and acyl. Examples of carboxy ester include $CO_2C_{1-20}$alkyl, $CO_2$aryl (e.g. $CO_2$phenyl), $CO_2$aralkyl (e.g. $CO_2$ benzyl).

The term "heteroatom" or "hetero" as used herein in its broadest sense refers to any atom other than a carbon atom which may be a member of a cyclic organic group.

Particular examples of heteroatoms include nitrogen, oxygen, sulfur, phosphorous, boron, silicon, selenium and tellurium, more particularly nitrogen, oxygen and sulfur.

It is understood that the compounds of the present invention (including monomers and polymers) may exist in one or more stereoisomeric forms (eg enantiomers, diastereomers). The present invention includes within its scope all of these stereoisomeric forms either isolated (in for example enantiomeric isolation), or in combination (including racemic mixtures).

The invention will now be described with reference to the following non-limiting examples and figures:

BRIEF DESCRIPTION OF THE FIGURES

Preferred embodiments of the invention will herein be illustrated by way of example only with reference to the accompanying drawings in which.

Figure 1:
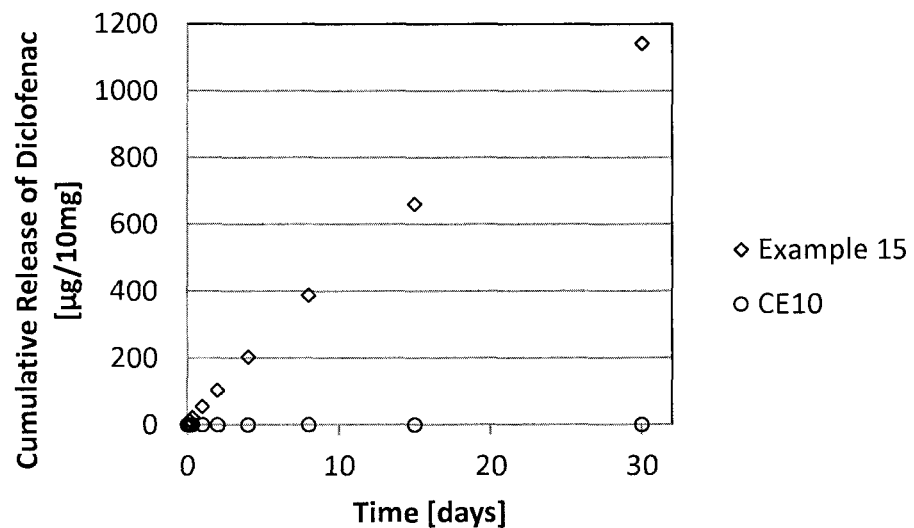
FIG. 1 is a graph illustrating the cumulative release of the NSAID diclofenac over time from a polymer-NSAID conjugate comprising the NSAID conjugated via an aryl ester and a hydrophilic group in accordance with an embodiment of the invention and a comparative polymer-NSAID conjugate comprising an NSIAD conjugated via an alkyl ester.

The following examples are intended to illustrate the scope of the invention and to enable reproduction and comparison. They are not intended to limit the scope of the disclosure in any way.

Examples

Automated flash chromatography was performed on a Teledyne ISCO CombiFlash $R_f$ 200 on silica gel using a combination of one or two of the following solvents: EtOAc, Pet. Spirit, DCM or MeOH.

Experimental Procedures

Procedure 1: General Procedure for HBTU Coupling

To a stirring suspension of carboxylic acid (1.0 eq.) in anhydrous DCM, HBTU (~1.2 eq.), the alcohol/glycerol derivative (~1.6 eq.) and triethylamine (~4.3 eq.) are added successively. The mixture is stirred at room temperature for 3 days, with the exclusion of light, or until the reaction is complete. The reaction mixture is washed with sat. $NaHCO_3$, follow by 0.1M HCl and brine. The organic phase is then dried over $Na_2SO_4$, filtered, concentrated and dried in vacuo.

Procedure 2: General Procedure for De-Acetylation

Ammonium acetate (~8 eq.) is added to a solution of acetate derivative (1.0 eq.) in 75% aqueous methanol. The mixture is stirred at room temperature for 16 hrs. The solvent is removed in vacuo. The residue is extracted with ethyl acetate. The organic phase is then dried over $Na_2SO_4$, filtered, concentrated and dried in vacuo.

Procedure 3: General Procedure for DCC Coupling

To a mixture of carboxylic acid (1.0 eq.), 4-dimethylaminopyridine (~0.05 eq.) and alcohol/glycerol derivative (~1.0 eq.) in anhydrous DCM, a solution of N,N'-dicyclohexylcarbodiimide (DCC) (~1.25 eq.) in anhydrous DCM (20 mL) is added dropwise at 0° C. The reaction mixture is stirred at 0° C. for 2 hours and slowly warmed to room temperature and stirred for 16 h or until the reaction is complete. The reaction mixture is passed through a thin bed of Celite to remove the by-product, DCU. Solvent is removed under reduced pressure.

Procedure 4: General Procedure for BOP-Cl Coupling

To a stirring suspension of carboxylic acid (1.0 eq.) in anhydrous DCM, bis(2-oxo-3-oxazolidinyl)phosphinic chloride (BOP-Cl) (~1.02 eq.), the alcohol/glycerol derivative (~1.06 eq.) and triethylamine (~2.0 eq.) are added successively. The mixture is stirred at room temperature for 16 hrs or until the reaction is complete. The reaction mixture is washed with sat. $NaHCO_3$, follow by water and brine. The organic phase is then dried over $Na_2SO_4$ filtered, concentrated and dried in vacuo.

Procedure 5: General Procedure for Benzylidene Acetal/Acetonide Deprotection a) Benzylidene acetal/acetonide protected derivative (~1 mmol) is dissolved in 80% acetic acid (20 mL) and stirred at 40° C. or 80° C. until the reaction is complete. The solvent is removed under reduced pressure and the residue is co-evaporated with toluene and dried in vacuo.

b) Benzylidene acetalacetonide protected derivative (~1 mmol) is dissolved in ethyl acetate containing a hydrogenation catalyst (10% w/w palladium on carbon) and is hydrogenated at 1 atmosphere of hydrogen (balloon) for 16 h at room temperature or until the reaction is complete. The reaction mixture is passed through a thin bed of Celite, concentrated and dried in vacuo.

Preparation of Intermediates

Intermediate A: 2-Phenyl-1,3-dioxan-5-yl 4-hydroxybenzoate

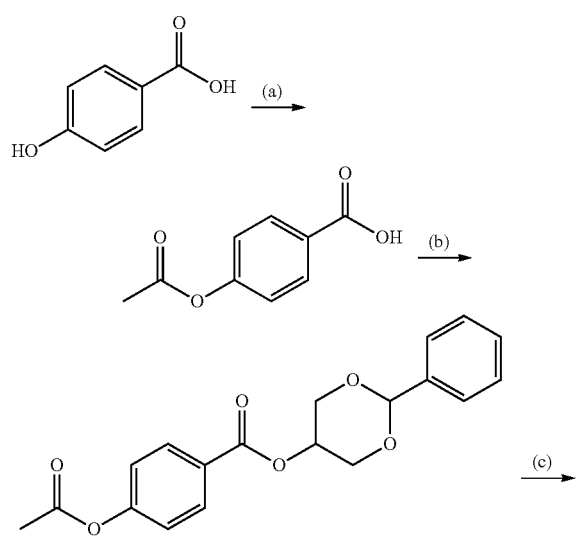

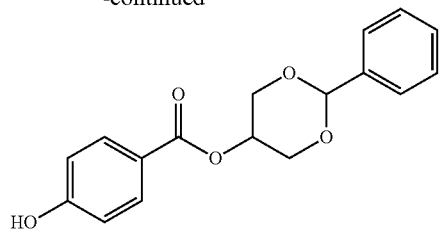

a) p-Hydroxybenzoic acid (1.081 g, 7.8 mmol) was dissolved in a 5:1 mixture of toluene: THF (50 mL). Pyridine (0.65 mL, 8.1 mmol) and acetic anhydride were added slowly at 0° C. The reaction mixture was stirred at room temperature for 16 hrs. Solvent was removed in vacuo. 4-Acetoxybenzoic acid was obtained in quantitative yield as a white solid and used without further purification. LC-MS: $M+H^+=181.0$, $M+Na^+=203.0$. $^1H$ NMR (400 MHz, $CDCl_3$): δ (ppm) 11.9 (br, 1H, COOH), 8.13 (d, 2H, ArH), 7.17 (d, 2H, ArH), 2.31 (s, 3H).

b) The general procedure for HBTU coupling (Procedure 1) was followed, using 4-acetoxybenzoic acid (5.245 g, 29.1 mmol), triethylamine (16 mL, 115.0 mmol), HBTU (11.500 g, 30.3 mmol) and 1,3-O-benzylidene glycerol (6.305 g, 34.9 mmol) in anhydrous dichloromethane (120 mL). The crude mixture was passed through a thin layer of silica gel to give 2-phenyl-1,3-dioxan-5-yl 4-acetoxybenzoate in 77% yield as a white solid. ESI-MS: $M+Na^+=365.1$. $^1H$ NMR (400 MHz, $CDCl_3$): δ (ppm) 8.19 (d, 2H), 7.40~7.49 (m, 5H), 7.17 (m, 2H), 5.61 (s, 1H), 4.41 (m, 1H), 4.3~4.1 (m, 4H), 2.31 (s, 3H). $^{13}C$ NMR (50 MHz, $CDCl_3$) δ 168.76, 165.52, 154.55, 137.93, 131.51, 129.12, 128.32, 128.27, 126.08, 121.63, 101.34, 69.07, 66.56, 21.11.

c) The general procedure for de-acetylation (Procedure 2) was followed, using ammonium acetate (13.806 g, 179.2 mmol), 2-phenyl-1,3-dioxan-5-yl 4-acetoxybenzoate (7.635 g, 22.0 mmol) in 75% aqueous methanol (250 mL). Recrystallization from DCM and dried in vacuo to give the title compound (Intermediate A) in 75% yield as a white powder. LC-MS: $M+Na^+=323.1$; $^1H$ NMR (400 MHz, Acetone-$d_6$): δ (ppm) 7.98 (d, 2H, ArH), 7.30~7.5 (m, 5H, ArH), 6.96 (d, 2H, ArH), 5.69 (s, 1H, CHPh), 4.92 (m, 1H, COOCH), 4.4~4.2 (m, 4H, $(CH_2O)_2$).

Intermediate B: (2,2-Dimethyl-1,3-dioxolan-4-yl)methyl 4-hydroxybenzoate

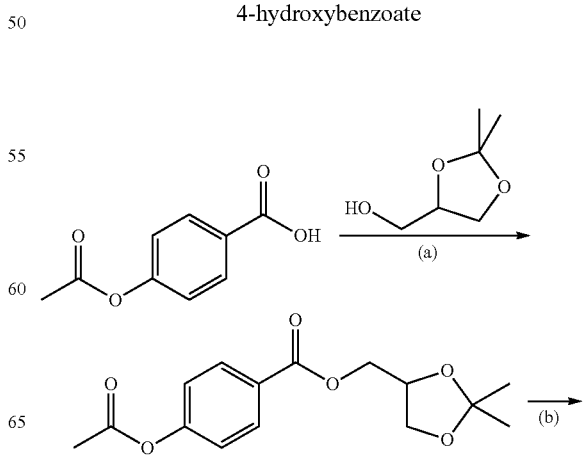

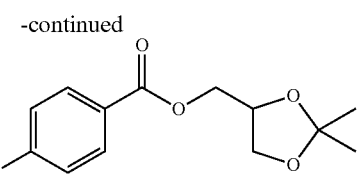

a) The general procedure for HBTU coupling (Procedure 1) was followed, using 4-acetoxy benzoic acid (4.501 g, 25.0 mmol), (±)-2,2-dimethyl-1,3-dioxolane-4-methanol (solketal, 3.304 g, 25.0 mmol), triethylamine (10.11 g, 13.91 ml, 100.0 mmol) and HBTU (9.48 g, 25.0 mmol) in anhydrous DCM. The crude mixture was passed through a thin layer of silica gel eluting with 30% ethyl acetate:hexanes to give (2,2-dimethyl-1,3-dioxolan-4-yl)methyl 4-acetoxybenzoate in 37% yield (2.706 g) as a pale yellow oil. $^1$H NMR (400 MHz, CDCl$_3$): δ (ppm) 8.11-8.04 (m, 2H), 7.21-7.10 (m, 2H), 4.50-4.26 (m, 3H), 4.20-4.01 (m, 1H), 3.91-3.81 (m, 1H), 2.31 (s, 3H), 1.45 (s, 3H), 1.38 (s, 3H).

b) The general procedure for de-acetylation (Procedure 2) was followed, using ammonium acetate (0.599 g, 7.77 mmol) and (2,2-dimethyl-1,3-dioxolan-4-yl)methyl 4-acetoxybenzoate (2.164 g, 7.35 mmol) in 80% aqueous methanol. The title compound (Intermediate B) was obtained in quantitative yield (1.96 g) as a white solid. $^1$H NMR (400 MHz, Acetone) δ (ppm) 7.97-7.85 (m, 2H), 6.96-6.86 (m, 2H), 4.49-4.37 (m, 1H), 4.36-4.22 (m, 2H), 4.13 (dd, J=8.4, 6.5 Hz, 1H), 3.86 (dd, J=8.4, 6.0 Hz, 1H), 1.36 (s, 3H), 1.30 (s, 3H). $^{13}$C NMR (101 MHz, Acetone) δ 165.43, 161.84, 131.65, 121.34, 115.16, 109.10, 73.75, 66.03, 64.46, 26.16, 24.72.

Intermediate C:
(5-Methyl-2-phenyl-1,3-dioxan-5-yl)methyl 4-hydroxybenzoate

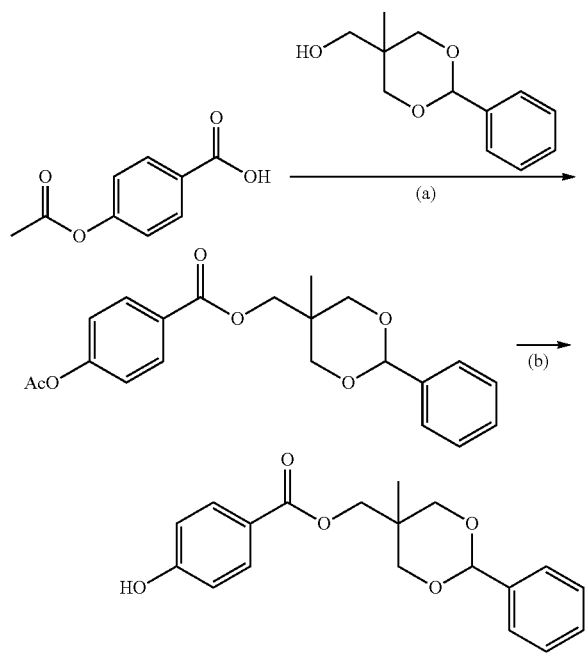

a) The general procedure for HBTU coupling (Procedure 1) was followed, using 4-acetoxy benzoic acid (3.03 g, 16.8 mmol), HBTU (6.30 g, 16.6 mmol), (5-methyl-2-phenyl-1,3-dioxan-5-yl)methanol (prepared according to the method of William et. al., *Tetrahedron Lett.* 2008, 49, 2091) (3.49 g, 16.8 mmol) and triethylamine (6.76 g, 66.8 mmol) in anhydrous DCM (150 mL). The crude mixture was passed through a thin layer of silica gel eluting with ethyl acetate. Followed by purification on the automated flash chromatography system using 0%-50% EtOAc in Pet. Spirit gradient elution gave (5-methyl-2-phenyl-1,3-dioxan-5-yl)methyl 4-acetoxybenzoate (780 mg, 2.11 mmol, 13%). IR v$_{max}$ (cm$^{-1}$): 2964, 2855, 1759, 1719, 1604, 1506, 1468, 1271, 1194, 1161, 1098, 1015, 914, 760, 700. $^1$H NMR (400 MHz): δ (ppm) 0.90 (s, 3H), 2.33 (s, 3H), 3.74 (d, J=11.9 Hz, 2H), 4.16 (d, J=11.9 Hz, 2H), 4.65 (s, 2H), 5.48 (s, 1H), 7.16-7.19 (m, 2H), 7.34-7.40 (m, 3H), 7.49-7.52 (m, 2H), 8.06-8.10 (m, 2H). $^{13}$C NMR (100 MHz): δ 17.5, 21.3, 34.2, 67.3, 73.6, 102.2, 121.8, 126.3, 127.9, 128.5, 129.2, 131.3, 138.1, 154.5, 165.8, 169.0.

b) The general procedure for de-acetylation (Procedure 2) was followed, using ammonium acetate (355 mg, 50.1 mmol) and (5-methyl-2-phenyl-1,3-dioxan-5-yl)methyl 4-acetoxybenzoate (340 mg, 0.92 mmol) in 75% MeOH/H$_2$O (10 mL) at room temperature for 64.5 hrs. The title compound, (5-methyl-2-phenyl-1,3-dioxan-5-yl)methyl 4-hydroxybenzoate (Intermediate C) was obtained in 93% yield (280 mg, 0.85 mmol) as a white solid without further purification. $^1$H NMR (400 MHz): δ (ppm) 0.90 (s, 3H), 3.73 (d, J=11.9 Hz, 2H), 4.16 (d, J=11.9 Hz, 2H), 4.61 (s, 2H), 5.48 (s, 1H), 6.37 (s, 1H), 6.83-6.87 (m, 2H), 7.35-7.37 (m, 3H), 7.49-7.51 (m, 2H), 7.94-7.98 (m, 2H). $^{13}$C NMR (100 MHz): δ 17.4, 34.1, 66.8, 73.5, 102.1, 115.2, 122.8, 126.2, 128.4, 129.1, 131.9, 137.9, 159.8, 166.2.

Synthesis of NSAID-Monomer Conjugates

Example 1

1,3-Dihydroxypropan-2-yl 4-(2-(2-((2,6-dichlorophenyl)amino)phenyl)acetoxy)benzoate (DCF-PHB-2-MG)

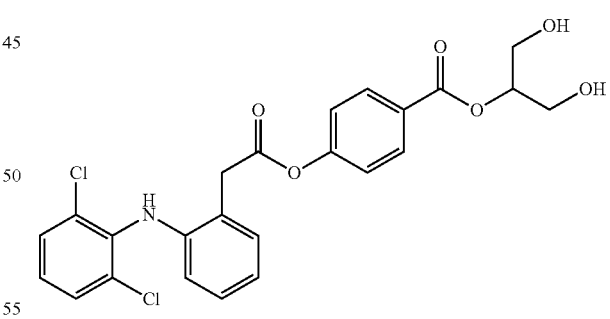

a) The general procedure for DCC coupling (Procedure 3) was followed, using diclofenac (4.152 g, 14.0 mmol), DCC (3.713 g, 17.9 mmol), DMAP (0.191 g, 1.6 mmol) and 2-phenyl-1,3-dioxan-5-yl 4-hydroxybenzoate (Intermediate A) (4.239 g, 14.1 mmol) in anhydrous DCM. The crude mixture was purified via column chromatography on silica gel (20% ethyl acetate/hexanes, followed by 30% ethyl acetate/hexanes as eluent) to give 2-phenyl-1,3-dioxan-5-yl 4-(2-(2-((2,6-dichlorophenyl)amino)phenyl)acetoxy)benzoate in 62% yield as a white solid. $^1$H NMR (200 MHz, CDCl$_3$) δ (ppm) 8.32-8.05 (m, 2H), 7.64-7.47 (m, 2H), 7.47-7.28 (m, 6H), 7.28-7.11 (m, 4H), 7.11-6.88 (m, 2H), 6.78-6.49 (m, 2H), 5.62 (s, 1H), 5.05-4.84 (m, 1H), 4.52-4.16 (m, 4H), 4.08 (s, 2H). $^{13}$C NMR (50 MHz, CDCl$_3$) δ 170.05, 165.47, 154.41, 142.67, 137.68, 131.55, 131.03, 129.45, 129.12, 128.85, 128.32, 126.07, 124.17, 123.56, 122.37, 121.63, 118.62, 101.37, 69.08, 66.58, 38.56. ESI-MS: m/z 581 (1%, M$^+$, C$_{31}$H$_{25}$$^{37}$Cl$_2$NO$_6$), 579 (4%, M$^+$, C$_{31}$H$_{25}$$^{37}$Cl$^{35}$ClNO$_6$), 577 (6%, M$^+$, C$_3$, H$_{25}$$^{35}$Cl$_2$NO$_6$), 543 (3), 541 (5), 280 (14), 279 (24), 277 (32), 214 (68), 121 (100), 105 (33). IR ν$_{max}$ (cm$^{-1}$): 3388, 3361, 2857, 1720, 1453, 1275, 1231, 1162, 1081, 1013, 767, 742.

b) The general procedure for benzylidene acetal/acetonide deprotection (Procedure 5b) was followed, using 2-phenyl-1,3-dioxan-5-yl 4-(2-(2-((2,6-dichlorophenyl)amino)phenyl)acetoxy)benzoate (3.206 g, 5.5 mmol) and 10% w/w palladium on carbon (0.301 g) in ethyl acetate (55 mL). The crude mixture was passed through a thin layer of silica gel (50% ethyl acetate/hexanes, followed by 10% methanol/chloroform as eluents) to give the title compound, 1,3-dihydroxypropan-2-yl 4-(2-(2-((2,6-dichlorophenyl)amino)phenyl)acetoxy)benzoate (DCF-PHB-2-MG) in 67% yield as an off-white solid. $^1$H NMR (200 MHz, CDCl$_3$) δ (ppm) 8.26-7.86 (m, 2H), 7.34 (d, J=8.0 Hz, 3H), 7.23-7.09 (m, 3H), 7.07-6.88 (m, 2H), 6.70-6.48 (m, 2H), 5.14 (p, J=4.7 Hz, 1H), 4.07 (s, 2H), 3.94 (d, J=4.7 Hz, 4H), 2.50 (bs, 2H). $^{13}$C NMR (50 MHz, CDCl$_3$) δ 170.10, 154.43, 142.66, 137.63, 131.38, 131.03, 129.44, 128.85, 128.41, 127.54, 124.21, 123.48, 122.37, 121.71, 118.59, 75.81, 62.43, 38.53. ESI-MS: m/z 493 (2%, M$^+$, C$_{24}$H$_{21}$$^{37}$Cl$_2$NO$_6$), 491 (6%, M$^+$, C$_{24}$H$_{21}$$^{37}$Cl$^{35}$ClNO$_6$), 489 (8%, M$^+$, C$_{24}$H$_{21}$$^{35}$Cl$_2$NO$_6$), 280 (22), 279 (36), 278 (34), 277 (49), 250 (20), 216 (40), 214 (100), 121 (83). IR ν$_{max}$ (cm$^{-1}$): 3541, 3326, 2981, 1741, 1703, 1504, 1453, 1302, 1230, 1121, 750.

Example 2

1,3-Dihydroxypropan-2-yl 4-((2-(4-isobutylphenyl)propanoyl)oxy)benzoate (IBP-PHB-2-MG)

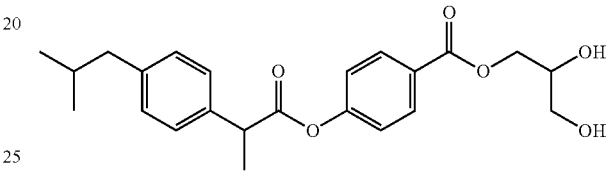

a) The general procedure for DCC coupling (Procedure 3) was followed, using Ibuprofen (3.67 g, 0.0178 mol), DCC (4.77 g, 0.0231 mol), 2-phenyl-1,3-dioxan-5-yl 4-hydroxybenzoate (Intermediate A) (5.53 g, 0.0184 mol) and DMAP (0.324 g, 2.66 mmol) in anhydrous DCM (200 mL). The crude mixture was purified via column chromatography on silica gel (20% ethyl acetate/hexanes, followed by 30% ethyl acetate/hexanes as eluents) to give 2-phenyl-1,3-dioxan-5-yl 4-((2-(4-isobutylphenyl)propanoyl)oxy)benzoate in 71% yield (5.98 g) as a white solid. $^1$H NMR (400 MHz, CDCl$_3$) δ (ppm) 0.90 (s, 3H), 0.91 (s, 3H), 1.60 (d, J=7.2 Hz, 3H), 1.82 (m, 1H), 2.47 (d, J=7.2 Hz, 2H), 3.92 (q, J=7.2 Hz, 1H), 4.24 (dd, J=1.6, 13.2, 2H), 4.39 (dd, J=1.6, 13.2, 2H), 4.94 (p, J=1.2 Hz, 1H), 5.61 (s, 1H), 7.08 (m, 4H), 7.29 (m, 5H), 7.52 (m, 2H), 8.03 (m, 2H).

b) The general procedure for benzylidene acetal/acetonide deprotection (Procedure 5a) was followed, using 2-phenyl-1,3-dioxan-5-yl 4-((2-(4-isobutylphenyl)propanoyl)oxy)benzoate (3.00 g, 6.34 mmol) in 80% acetic acid (100 mL) at 80° C. for 16 h. The title compound, 1,3-dihydroxypropan-2-yl 4-((2-(4-isobutylphenyl)propanoyl)oxy)benzoate (IBP-PHB-2-MG) was obtained in 91% yield (2.31 g) as a clear oil. $^1$H NMR (400 MHz, CDCl$_3$) δ (ppm) 0.90 (d, J=9.2 Hz, 6H), 1.60 (d, J=7.2 Hz, 3H), 1.82 (m, 1H), 2.47 (d, J=7.2 Hz, 2H), 3.92 (m, 4H), 5.13 (p, J=4.8 Hz, 1H), 7.08 (m, 4H), 7.27 (m, 2H), 7.95 (m, 2H).

Example 3

2,3-Dihydroxypropyl 4-((2-(4-isobutylphenyl)propanoyl)oxy)benzoate (IBP-PHB-1-MG)

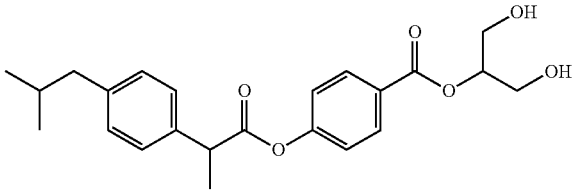 [SMILES: CC(C)Cc1ccc(C(C)C(=O)Oc2ccc(C(=O)OC(CO)CO)cc2)cc1]

a) The general procedure for BOP-Cl coupling (Procedure 4) was followed, using ibuprofen (0.402 g, 1.95 mmol), (2,2-dimethyl-1,3-dioxolan-4-yl)methyl 4-hydroxybenzoate (Intermediate B) (0.522 g, 2.06 mmol), BOP-Cl (0.518 g, 2.03 mmol) and triethylamine (0.55 mL, 0.40 g, 3.95 mmol) in anhydrous DCM (15 mL). The crude mixture was purified on the automated flash chromatography system using 0%-40% EtOAc in pet. spirit gradient elution to give (2,2-dimethyl-1,3-dioxolan-4-yl)methyl 4-((2-(4-isobutylphenyl)propanoyl)oxy)benzoate as a clear colourless oil in 75% yield. $^1$H NMR (400 MHz, CDCl$_3$): δ (ppm) 8.13-7.99 (m, 2H), 7.38-7.27 (m, 2H), 7.22-7.11 (m, 2H), 7.11-7.01 (m, 2H), 4.50-4.39 (m, 1H), 4.39-4.26 (m, 2H), 4.23-4.02 (m, 1H), 3.94 (q, J=7.1 Hz, 1H), 3.85 (dd, J=8.5, 5.9 Hz, 1H), 2.47 (d, J=7.2 Hz, 2H), 1.94-1.78 (m, 1H), 1.67-1.56 (m, 3H), 1.44 (s, 3H), 1.38 (s, 3H), 0.92 (s, 3H), 0.90 (s, 3H). $^{13}$C NMR (101 MHz, CDCl$_3$) δ 172.79, 165.68, 154.86, 141.14, 136.99, 131.35, 129.72, 127.35, 127.31, 121.66, 110.00, 73.78, 66.48, 65.24, 45.42, 45.16, 30.31, 26.86, 25.49, 22.51, 18.57.

b) The general procedure for benzylidene acetal/acetonide deprotection (Procedure 5a) was followed, using (2,2-dimethyl-1,3-dioxolan-4-yl)methyl-4-((2-(4-isobutylphenyl)propanoyl)oxy)benzoate (0.250 g, 0.57 mmol) in 80% aqueous acetic acid (10 mL). The mixture was heated at 40° C. for 4 hours. The crude mixture was purified on the automated flash chromatography system using 25%-100% EtOAc in pet. spirit gradient elution to give the title compound in 73% yield (0.166 g) as a clear colourless oil. ESI-MS: m/z 423.2 ([M+Na]$^+$). $^1$H NMR (400 MHz, CDCl$_3$) δ (ppm) 8.08-7.96 (m, 2H), 7.36-7.26 (m, 2H), 7.20-7.11 (m, 2H), 7.11-6.97 (m, 2H), 4.45-4.31 (m, 2H), 4.07-3.99 (m, 1H), 3.94 (q, J=7.1 Hz, 1H), 3.69 (ddd, J=17.3, 11.5, 4.9 Hz, 2H), 2.54 (s, 2H), 2.47 (d, J=7.2 Hz, 2H), 1.96-1.75 (m, 1H), 1.60 (d, J=7.2 Hz, 3H), 0.91 (s, 3H), 0.90 (s, 3H). $^{13}$C NMR (101 MHz, CDCl$_3$) δ 172.85, 166.28, 154.95, 141.15, 136.93, 131.36, 129.72, 127.30, 127.17, 121.73, 70.39, 65.93, 63.48, 45.41, 45.15, 30.29, 22.50, 18.55.

Example 4

2,3-Dihydroxypropyl 4-(2-(2-((2,6-dichlorophenyl)amino)phenyl)acetoxy)benzoate (DCF-PHB-1-MG)

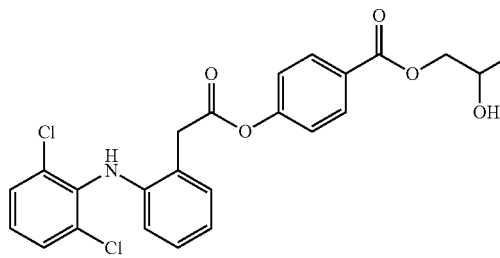

a) The general procedure for DCC coupling (Procedure 3) was followed, using diclofenac (0.802 g, 2.71 mmol), DMAP (0.022 g, 0.18 mmol), DCC (0.698 g, 3.38 mmol) and (2,2-dimethyl-1,3-dioxolan-4-Mmethyl 4-hydroxybenzoate (Intermediate B) (0.688 g, 2.7 mmol) in anhydrous DCM (25 mL). The crude mixture was purified on the automated flash chromatography system using 5%-50% EtOAc in pet. spirit gradient elution to give (2,2-dimethyl-1,3-dioxolan-4-yl)methyl 4-(2-(2-((2,6-dichlorophenyl)amino)phenyl)acetoxy)benzoate in 53% yield (0.764 g) as a clear colourless oil. ESI-MS: m/z 553.0 ([M+Na]$^+$). $^1$H NMR (400 MHz, CDCl$_3$) δ 8.14-8.03 (m, 2H), 7.39-7.28 (m, 3H), 7.24-7.12 (m, 3H), 7.06-6.90 (m, 2H), 6.67 (s, 1H), 6.59 (d, J=8.0 Hz, 1H), 4.50-4.30 (m, 3H), 4.19-4.10 (m, 1H), 4.07 (s, 2H), 3.91-3.81 (m, 1H), 1.45 (s, 3H), 1.38 (s, 3H). $^{13}$C NMR (101 MHz, CDCl$_3$) δ 170.21, 165.59, 154.46, 142.80, 137.79, 131.46, 131.16, 129.58, 129.00, 128.54, 127.70, 124.35, 123.66, 122.51, 121.79, 118.73, 110.00, 73.75, 65.32, 60.50, 38.68, 26.86, 25.47, 14.31.

b) The general procedure for benzylidene acetal/acetonide deprotection (Procedure 5a) was followed, using (2,2-dimethyl-1,3-dioxan-4-yl)methyl 4-(2-(2-((2,6-dichlorophenyl)amino)phenyl)acetoxy)benzoate (0.700 g, 1.32 mmol) in 80% aqueous acetic acid (15 mL). The mixture was heated at 70° C. for 19.5 h before the solvent was removed under reduced pressure. The crude material was purified on the automated chromatography system using 15%-95% EtOAc in pet. spirit gradient elution to give the title compound. LC-MS: M+H$^+$=492.2. $^1$H NMR (400 MHz): δ 8.11-8.05 (m, 2H), 7.36-7.31 (m, 2H), 7.21-7.16 (m, 3H), 7.02 (td, J=7.6, 0.8 Hz, 1H), 6.99 (t, J=8.0 Hz, 1H), 6.67 (s, 1H), 6.59 (d, J=8.0 Hz, 1H), 4.43 (dd, J=11.6, 4.9 Hz, 2H), 4.38 (dd, J=11.6, 6.0 Hz, 1H), 4.09-4.02 (m, 3H), 3.76 (dd, J=11.5, 3.9 Hz, 1H), 3.66 (dd, J=11.5, 5.8 Hz, 1H).

Example 5

1,3-Dihydroxypropan-2-yl 4-(2-(1-(4-chlorobenzoyl)-5-methoxy-2-methyl-1H-indol-3-yl)acetoxy)benzoate (IND-PHB-2-MG)

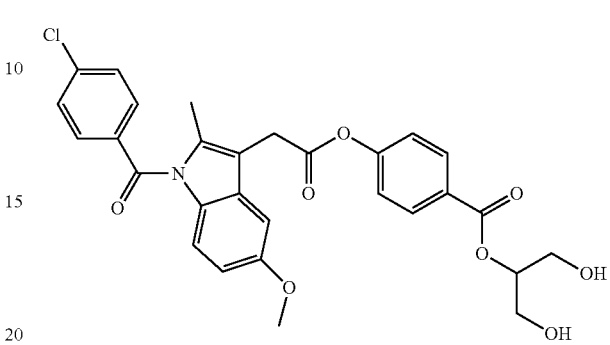

a) The general procedure for HBTU coupling (Procedure 1) was followed, using indomethacin (1.065 g, 2.98 mmol), 2-phenyl-1,3-dioxan-5-yl 4-hydroxybenzoate (Intermediate A) (1.094 g, 3.64 mmol), HBTU (1.308 g, 3.45 mmol) and triethylamine (1.62 mL, 1.18 g, 11.6 mmol) in anhydrous DCM (50 mL). The crude mixture was purified on the automated flash chromatography system using 0%-45% EtOAc in pet. spirit gradient elution to give 2-phenyl-1,3-dioxan-5-yl 4-(2-(1-(4-chlorobenzoyl)-5-methoxy-2-methyl-1H-indol-3-yl)acetoxy)benzoate in 52% yield as an off-white solid. $^1$H NMR (400 MHz, CDCl$_3$) δ (ppm) 8.20-8.03 (m, 2H), 7.69-7.56 (m, 2H), 7.52-7.37 (m, 4H), 7.37-7.24 (m, 3H), 7.14-7.04 (m, 2H), 7.00-6.90 (m, 1H), 6.86-6.77 (m, 1H), 6.70-6.42 (m, 1H), 5.54 (s, 1H), 4.91-4.79 (m, 1H), 4.45-4.12 (m, 4H), 3.85 (s, 2H), 3.76 (s, 3H), 2.39 (s, 3H). $^{13}$C NMR (101 MHz, CDCl$_3$) δ 168.73, 168.33, 165.51, 156.17, 154.56, 139.43, 137.90, 136.36, 133.78, 131.56, 131.23, 130.87, 130.42, 129.19, 128.38, 127.66, 126.09, 121.51, 115.08, 111.85, 111.63, 101.40, 101.18, 69.11, 66.63, 55.77, 30.59, 13.44.

b) The general procedure for benzylidene acetal/acetonide deprotection (Procedure 5a) was followed, using 2-phenyl-1,3-dioxan-5-yl 4-(2-(1-(4-chlorobenzoyl)-5-methoxy-2-methyl-1H-indol-3-yl)acetoxy)benzoate (0.365 g, 0.57 mmol) in 80% aqueous acetic acid (15 mL). The mixture was heated at 80° C. for 5 hrs. The crude mixture was purified on the automated flash chromatography system using 40%-100% EtOAc in pet. spirit gradient elution to give the title compound, 1,3-dihydroxypropan-2-yl 4-(2-(1-(4-chlorobenzoyl)-5-methoxy-2-methyl-1H-indol-3-yl)acetoxy)benzoate (IND-PHB-2-MG) in 15% yield as a pale yellow solid. $^1$H NMR (400 MHz, CDCl$_3$) δ 8.14-7.99 (m, 2H), 7.77-7.60 (m, 2H), 7.54-7.37 (m, 2H), 7.19-7.07 (m, 2H), 7.03 (d, J=2.4 Hz, 1H), 6.92-6.82 (m, 1H), 6.69 (dd, J=9.1, 2.5 Hz, 1H), 5.11 (p, J=4.8 Hz, 1H), 3.95-3.86 (m, 6H), 3.82 (s, 3H), 2.44 (s, 3H). $^{13}$C NMR (101 MHz, CDCl$_3$) δ 169.03, 168.55, 165.93, 156.34, 154.75, 139.64, 136.59, 133.91, 131.59, 131.53, 131.41, 131.06, 130.60, 129.38, 127.68, 121.76, 115.27, 111.94, 111.77, 101.46, 76.00, 62.44, 55.95, 30.71, 13.62.

Example 6

2,3-Dihydroxypropyl 4-(2-(1-(4-chlorobenzoyl)-5-methoxy-2-methyl-1H-indol-3-yl)acetoxy)benzoate (IND-PHB-1-MG)

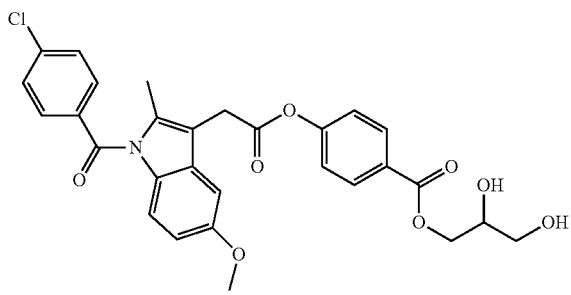 [SMILES: COc1ccc2c(c1)c(CC(=O)Oc1ccc(C(=O)OCC(O)CO)cc1)c(C)n2C(=O)c1ccc(Cl)cc1]

a) The general procedure for HBTU coupling (Procedure 1) was followed, using indomethacin (0.655 g, 1.83 mmol) (2,2-dimethyl-1,3-dioxolan-4-yl)methyl 4-hydroxybenzoate (Intermediate B) (0.556 g, 2.21 mmol), HBTU (0.703 g, 1.85 mmol) and triethylamine (1.02 mL, 0.742 g, 7.33 mmol) in anhydrous DCM (30 mL). The crude mixture was purified on the automated flash chromatography system using 0%-50% EtOAc in pet. spirit gradient elution to give a mixture of (2,2-dimethyl-1,3-dioxolan-4-yl)methyl 4-(2-(1-(4-chlorobenzoyl)-5-methoxy-2-methyl-1H-indol-3-yl)acetoxy)benzoate and by-products. The mixture was used directly without further purification.

b) The general procedure for benzylidene acetal/acetonide deprotection (Procedure 5a) was followed, using the mixture of (2,2-dimethyl-1,3-dioxolan-4-yl)methyl 4-(2-(1-(4-chlorobenzoyl)-5-methoxy-2-methyl-1H-indol-3-yl)acetoxy)benzoate and by-products in 80% aqueous acetic acid (5 mL). The mixture was heated at 80° C. for 16 hrs. The crude mixture was purified on the automated flash chromatography system using 55%-100% EtOAc in pet. spirit gradient elution to give the title compound, 2,3-dihydroxypropyl 4-(2-(1-(4-chlorobenzoyl)-5-methoxy-2-methyl-1H-indol-3-yl)acetoxy)benzoate (IND-PH B-1-MG) in 12% yield as a pale yellow solid. $^1$H NMR (400 MHz, CDCl$_3$) δ (ppm) 8.15-7.96 (m, 2H), 7.78-7.60 (m, 2H), 7.58-7.42 (m, 2H), 7.22-7.10 (m, 2H), 7.03 (d, J=2.5 Hz, 1H), 6.88 (d, J=9.0 Hz, 1H), 6.70 (dd, J=9.0, 2.5 Hz, 1H), 4.56-4.32 (m, 2H), 4.08-3.98 (m, 1H), 3.97-3.88 (m, 3H), 3.83 (s, 3H), 3.71 (ddd, J=17.2, 11.4, 4.9 Hz, 2H), 2.46 (s, 3H). $^{13}$C NMR (101 MHz, CDCl$_3$) δ 168.86, 168.46, 166.22, 156.29, 154.73, 139.60, 136.52, 133.86, 131.48, 131.36, 130.99, 130.52, 129.32, 127.41, 121.73, 115.20, 111.91, 111.68, 101.36, 70.42, 66.01, 63.49, 55.89, 13.55.

Example 7

4-(((1,3-Dihydroxypropan-2-yl)oxy)carbonyl)phenyl 5-benzoyl-2,3-dihydro-1H-pyrrolizine-1-carboxylate (KTC-PHB-2-MG)

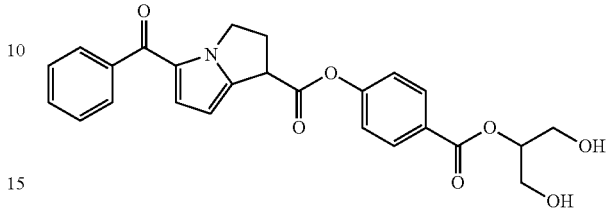

a) The general procedure for DCC coupling (Procedure 3) was followed, using ketorolac (1.52 g, 5.95 mmol), DMAP (32 mg, 0.26 mmol), DCC (1.27 g, 6.16 mmol) and 2-phenyl-1,3-dioxan-5-yl 4-hydroxybenzoate (Intermediate A) (1.85 g, 6.16 mmol) in anhydrous THF (10 mL). The mixture was purified on the automatic flash chromatography system using 20%-100% EtOAc in pet. spirit gradient elution to give 4-(((2-phenyl-1,3-dioxan-5-yl)oxy)carbonyl) phenyl 5-benzoyl-2,3-dihydro-1H-pyrrolizine-1-carboxylate in 45% yield (1.44 g, 2.68 mmol) as a brownish solid. $^1$H NMR (400 MHz): δ (ppm) 8.23-8.19 (m, 2H), 7.85-7.83 (m, 2H), 7.56-7.52 (m, 3H), 7.48-7.45 (m, 2H), 7.42-7.36 (m, 3H), 7.23-7.19 (m, 2H), 6.87 (d, J=4.0 Hz, 1H), 6.25 (dd, J=4.0, 0.8 Hz, 1H), 5.63 (s, 1H), 4.96 (s, 1H), 4.65 (ddd, J=12.3, 8.5, 5.7 Hz, 1H), 4.53 (ddd, J=12.2, 8.4, 5.8 Hz, 1H), 4.42 (dd, J=12.8, 0.8 Hz, 2H), 4.35 (dd, J=8.9, 5.6 Hz, 1H), 4.27 (dd, J=13.0, 1.5 Hz, 2H), 3.13-3.05 (m, 1H), 2.98-2.90 (m, 1H). $^{13}$C NMR (100 MHz): δ 185.3, 169.3, 165.6, 154.6, 141.3, 139.3, 138.0, 131.8, 131.7, 129.3, 129.1, 128.5, 128.4, 128.0, 126.2, 125.2, 121.6, 103.5, 101.5, 69.3, 66.9, 47.7, 42.9, 31.0. IR $v_{max}$ (cm$^{-1}$): 3062, 2982, 2928, 2857, 1762, 1716, 1675, 1623, 1577, 1505, 1465, 1399, 1269, 1200, 1143, 1118, 1082, 1016, 865, 724, 669.

b) The general procedure for benzylidene acetal/acetonide deprotection (Procedure 5a) was followed, using 4-(((2-phenyl-1,3-dioxan-5-yl)oxy)carbonyl)phenyl 5-benzoyl-2,3-dihydro-1H-pyrrolizine-1-carboxylate (357 mg, 0.642 mmol) in 80% acetic acid (15 mL). The mixture was heated at 70° C. for 25 hrs. The crude mixture was passed through a thin layer of silica gel (30% EtOAc/pet.spirit, followed by 10% MeOH/DCM as eluents).

The MeOH/DCM washings were concentrated and dried in vacuo. The residue was purified on the automated flash chromatography system using 0-10% MeOH in DCM gradient elution to give the title compound, 4-(((1,3-dihydroxypropan-2-yl)oxy)carbonyl)phenyl 5-benzoyl-2,3-dihydro-1H-pyrrolizine-1-carboxylate (KTC-PHB-2-MG) in 35% yield (105 mg, 0.234 mmol) as a yellow solid. $^1$H NMR (400 MHz): δ (ppm) 2.12 (m, 2H), 2.89-2.98 (m, 1H), 3.04-3.12 (m, 1H), 3.98 (t, J=4.7 Hz, 4H), 4.35 (dd, J=8.9, 5.6 Hz, 1H), 4.53 (ddd, J=12.2, 8.4, 5.8 Hz, 1H), 4.65 (ddd, J=12.3, 8.5, 5.7 Hz, 1H), 5.17 (p, J=4.7 Hz, 1H), 6.24 (dd, J=4.0, 0.8 Hz, 1H), 6.87 (d, J=4.0 Hz, 1H), 7.19-7.22 (m, 2H), 7.45-7.49 (m, 2H), 7.53-7.57 (tt, J=7.2, 1.2 Hz, 1H), 7.81-7.86 (m, 2H), 8.10-8.13 (m, 2H). $^{13}$C NMR (100 MHz): δ 30.9, 42.9, 47.7, 62.7, 76.1, 103.5, 121.7, 125.2, 127.7, 127.8, 128.4, 129.1, 131.6, 131.7, 139.2, 141.2, 154.6, 165.8, 169.3, 185.3. IR $v_{max}$ (cm$^{-1}$): 3391, 2934, 1713, 1660, 1607, 1571, 1509, 1493, 1431, 1398, 1272, 1165, 1116, 1048, 892, 769, 725.

c) The general procedure for benzylidene acetal/acetonide deprotection (Procedure 5a) was followed, using 4-(((2,2-dimethyl-1,3-dioxolan-4-yl)methoxy)carbonyl)phenyl-5-benzoyl-2,3-dihydro-1H-pyrrollizine-1-carboxylate (0.3 g, 0.61 mmol) in 80% acetic acid. The mixture was heated at 42° C. for 3 h. The crude mixture was purified on the automated flash chromatography system using 0%-10% MeOH in DCM gradient elution to give the title compound, 4-((2,3-Dihydroxypropoxy)carbonyl)phenyl 5-benzoyl-2,3-dihydro-1H-pyrrolizine-1-carboxylate (KTC-PHB-1-MG) in 68% yield as clear pale yellow oil. ESI-MS: M+H$^+$=450.1; $^1$H NMR (400 MHz, CDCl$_3$) δ (ppm) 8.15-8.05 (m, 2H), 7.88-7.79 (m, 2H), 7.59-7.51 (m, 1H), 7.46 (tt, J=6.7, 1.4 Hz, 2H), 7.25-7.16 (m, 2H), 6.87 (d, J=4.0 Hz, 1H), 6.24 (dd, J=4.0, 0.8 Hz, 1H), 4.73-4.60 (m, 1H), 4.59-4.29 (m, 4H), 4.13-4.01 (m, 1H), 3.72 (ddd, J=17.2, 11.5, 4.9 Hz, 2H), 3.18-2.84 (m, 2H). $^{13}$C NMR (101 MHz, CDCl$_3$) δ 185.32, 169.31, 166.18, 154.6, 141.28, 139.18, 131.71, 131.58, 129.05, 128.36, 127.68, 127.66, 125.22, 121.66, 103.48, 70.42, 66.05, 63.50, 47.68, 42.85, 30.89.

Example 8

4-((2,3-Dihydroxypropoxy)carbonyl)phenyl 5-benzoyl-2,3-dihydro-1H-pyrrolizine-1-carboxylate (KTC-PHB-1-MG)

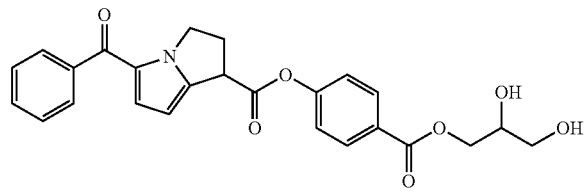 [SMILES: O=C(OCC(O)CO)c1ccc(OC(=O)C2CCn3c(C(=O)c4ccccc4)ccc32)cc1]

a) The general procedure for BOP-Cl coupling (Procedure 4) was followed, using ketorolac (0.399 g, 1.57 mmol), BOP-Cl (0.398 g, 1.57 mmol), (2,2-dimethyl-1,3-dioxolan-4yl)methyl-4-hydroxybenzoate (Intermediate B) (0.395 g, 1.57 mmol) and triethylamine (0.317 g, 0.436 mL, 3.13 mmol) in anhydrous DCM (10 mL). The crude mixture was purified by on the automated flash chromatography system using 0%-5% MeOH in DCM gradient elution to give 4-(((2,2-dimethyl-1,3-dioxolan-4-yl)methoxy)carbonyl)phenyl-5-benzoyl-2,3-dihydro-1H-pyrrollizine-1-carboxylate in 69% yield as a clear oil. LC-MS: M+H$^+$=490.2; $^1$H NMR (400 MHz, CDCl$_3$) δ 8.34-7.94 (m, 2H), 7.94-7.80 (m, 2H), 7.57-7.39 (m, 3H), 7.23-7.16 (m, 2H), 6.87 (d, J=4.0 Hz, 1H), 6.24 (dd, J=4.0, 0.7 Hz, 1H), 4.65 (ddd, J=12.3, 8.5, 5.8 Hz, 1H), 4.59-4.28 (m, 5H), 4.14 (dd, J=8.5, 6.3 Hz, 1H), 3.86 (dd, J=8.5, 5.8 Hz, 1H), 3.08 (ddt, J=14.1, 8.5, 5.7 Hz, 1H), 3.00-2.86 (m, 1H), 1.45 (s, 3H), 1.39 (s, 3H). $^{13}$C NMR (101 MHz, CDCl$_3$) δ 185.25, 169.31, 165.58, 154.48, 141.26, 139.23, 131.68, 131.57, 129.05, 128.42, 128.35, 127.86, 127.69, 125.12, 122.00, 121.58, 110.06, 103.44, 73.78, 66.48, 65.38, 47.68, 42.86, 32.42, 30.90, 26.88, 26.32, 25.50.

Example 9

3,5-Dihydroxyphenyl 2-(2-((2,6-dichlorophenyl)amino)phenyl)acetate (DCF-phloroglucinol ester)

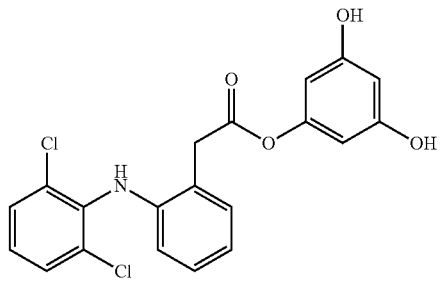 [SMILES: O=C(Cc1ccccc1Nc1c(Cl)cccc1Cl)Oc1cc(O)cc(O)c1]

The general procedure for DCC coupling (Procedure 3) was followed; using diclofenac (0.579 g, 1.95 mmol), DMAP (0.016 g, 0.13 mmol), phloroglucinol dihydrate (0.319 g, 1.96 mmol) and DCC (0.510 g, 2.47 mmol) in anhydrous DCM (25 mL), The crude mixture was purified on the automated flash chromatography system using 0%-50% EtOAc in pet. spirit gradient elution to give the title compound, 3,5-dihydroxyphenyl 2-(2-((2,6-dichlorophenyl)amino)phenyl)acetate (DCF-phloroglucinol ester) ESI-MS: m/z 450.0 ([M+2Na]$^+$) and benzene-1,3,5-triyl tris(2-(2-((2,6-dichlorophenyl)amino)phenyl)acetate). $^1$H NMR (400 MHz, CDCl$_3$) δ (ppm) 7.45-7.22 (m, 5H), 7.15 (td, J=7.8, 1.5 Hz, 1H), 7.05-6.92 (m, 2H), 6.87 (s, 1H), 6.61 (s, 1H), 6.57 (d, J=8.0 Hz, 1H), 4.00 (s, 2H). $^{13}$C NMR (101 MHz, CDCl$_3$) δ 169.79, 150.98, 142.67, 137.71, 131.02, 129.49, 128.83, 128.38, 124.13, 123.53, 122.40, 118.67, 113.16, 38.43. The mixture was used without further purification.

In an alternate method:
(i) The general procedure for DCC coupling (Procedure 3) is followed; using diclofenac (1 eq), DMAP (0.1 eq), 3,5-bis(benzyloxy)phenol (prepared using the procedure described by Stoltz et. al., Org. Lett. 2010, 12, 1224) (1 eq.) and DCC (1.25 eq) in anhydrous DCM (25 mL). The mixture is concentrated under reduced pressure and the crude material is purified via column chromatography on silica gel (0-50% ethyl acetate/petrol gradient elution) to give 3,5-bis(benzyloxy)phenyl 2-(2-((2,6-dichlorophenyl)amino)phenyl)acetate.

ii) To a solution of 3,5-bis(benzyloxy)phenyl 2-(2-((2,6-dichlorophenyl)amino)phenyl)acetate in EtOAc is added 10% Pd/C. A hydrogen balloon is attached to the system and the reaction is stirred under 1 atm H$_2$ at room temperature until the reaction is complete by TLC analysis. The reaction mixture is then filtered through Celite and concentrated under reduced pressure. The crude product is purified by flash chromatography (0-100% EtOAc/petrol gradient elution) to produce 3,5-dihydroxyphenyl 2-(2-((2,6-dichlorophenyl)amino)phenyl)acetate.

Example 10

3-Hydroxy-2-(hydroxymethyl)-2-methylpropyl 4-(2-(2-((2,6-dichlorophenyl)amino)phenyl)acetoxy)benzoate (DCF-PHB-THE)

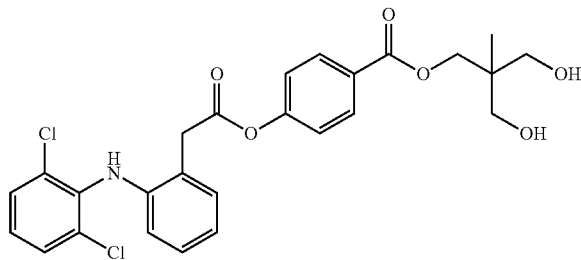 [SMILES: CC(CO)(CO)COC(=O)c1ccc(OC(=O)Cc2ccccc2Nc2c(Cl)cccc2Cl)cc1]

a) The general procedure for the DCC coupling (Procedure 3) was followed, using diclofenac (240 mg, 0.81 mmol), DCC (221 mg, 1.07 mmol), (5-methyl-2-phenyl-1,3-dioxan-5-yl)methyl 4-hydroxybenzoate (Intermediate C) (280 mg, 0.85 mmol) and DMAP (9 mg, 0.07 mmol) in a mixture of DCM (10 mL) and THF (2 mL). The crude mixture was purified on the automated flash chromatography system using 10%-50% EtOAc in pet. spirit gradient elution to give (5-methyl-2-phenyl-1,3-dioxan-5-yl)methyl 4-(2-(2-((2,6-dichlorophenyl)amino)phenyl)acetoxy)benzoate in 95% yield (466 mg, 0.77 mmol) as a clear viscous oil. $^1$H NMR (400 MHz): δ (ppm) 0.90 (s, 3H), 3.74 (d, J=11.9 Hz, 2H), 4.07 (s, 2H), 4.16 (d, J=11.9 Hz, 2H), 4.64 (s, 2H), 5.47 (s, 1H), 6.60 (d, J=8.0 Hz, 1H), 6.67 (s, 1H), 6.99 (t, J=8.0 Hz), 7.02 (td, J=7.6, 0.8 Hz, 1H), 7.15-7.22 (m, 3H), 7.32-7.41 (m, 6H), 7.49 (dd, J=7.8, 1.7 Hz, 2H), 8.07 (d, J=8.05-8.09 (m, 2H). $^{13}$C NMR (100 MHz): δ 17.5, 34.2, 38.7, 67.3, 73.6, 102.2, 118.8, 121.8, 122.5, 124.4, 126.3, 128.5, 128.6, 129.0, 129.2, 129.6, 131.2, 131.3, 142.8, 154.3, 165.8, 170.3. IR $v_{max}$ (cm$^{-1}$): 3339, 3068, 2962, 2855, 1747, 1720, 1600, 1585, 1503, 1455, 1391, 1273, 1024, 1161, 1098, 1017, 969, 917, 866, 756.

b) The general procedure for benzylidene acetal/acetonide deprotection (Procedure 5b) was followed, using (5-methyl-2-phenyl-1,3-dioxan-5-yl)methyl 4-(2-(2-((2,6-dichlorophenyl)amino)phenyl)acetoxy)benzoate (202.6 mg, 0.334 mmol) and 10% w/w Pd/C (26 mg) in EtOAc (5 mL). The crude mixture was purified on the automated flash chromatography system using 0%-20% MeOH in DCM gradient elution to give the title compound, 3-hydroxy-2-(hydroxymethyl)-2-methylpropyl 4-(2-(2-((2,6-dichlorophenyl)amino)phenyl)acetoxy)benzoate (DCF-PHB-THE) in 59% yield (102 mg, 0.197 mmol). $^1$H NMR (400 MHz): δ (ppm) 0.92 (s, 3H), 2.76 (br s, 2H), 3.59 (d, J=11.3 Hz, 2H), 3.66 (d, J=11.3 Hz, 2H), 4.08 (s, 2H), 4.46 (s, 2H), 6.60 (d, J=8.0 Hz, 1H), 6.66 (s, 1H), 7.00 (t, J=7.9 Hz, 1H), 7.03 (td, J=7.5, 0.9 Hz, 1H), 7.16-7.22 (m, 3H), 7.33-7.36 (m, 2H), 8.06-8.09 (m, 2H). $^{13}$C NMR (100 MHz): δ 17.1, 38.7, 41.3, 67.2, 68.1, 118.8, 121.9, 122.6, 123.7, 124.4, 127.6, 128.6, 129.0, 129.6, 131.2, 131.5, 137.8, 142.8, 154.6, 166.8, 170.3. IR $v_{max}$ (cm$^{-1}$): 3350, 2961, 2884, 1747, 1715, 1600, 1584, 1504, 1454, 1414, 1280, 1203, 1160, 1211, 1407, 1020, 969, 918, 867, 764.

Comparative Example 1 (CE1)

2,3-dihydroxypropyl 2-(4-isobutylphenyl)propanoate (IBP-1-MG)

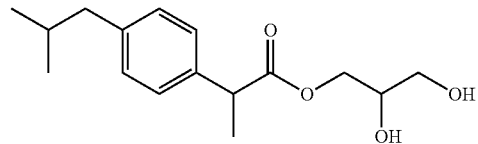 [SMILES: CC(C)Cc1ccc(C(C)C(=O)OCC(O)CO)cc1]

The method of Davaran and Entezami was used (J. Bioactive and Compatible Polymers, 1997, 12, 47-58) to give title compound, 2,3-dihydroxypropyl 2-(4-isobutylphenyl)propanoate (IBP-1-MG) in 30% yield as an amber oil. LC-MS: M+H$^+$=281.1, M+Na$^+$=301.1. $^1$H NMR (400 MHz, CDCl$_3$) δ (ppm) 7.18 (d, J=8.1 Hz, 2H), 7.09 (d, J=8.1 Hz, 2H), 4.21-4.03 (m, 2H), 3.87-3.77 (m, 1H), 3.73 (q, J=7.2 Hz, 1H), 3.59-3.49 (m, 1H), 3.43 (ddd, J=11.5, 5.7, 4.2 Hz, 1H), 2.87 (bs, 1H), 2.55 (bs, 1H), 2.44 (d, J=7.2 Hz, 2H), 1.92-1.75 (m, 1H), 1.49 (d, J=7.2 Hz, 3H), 0.88 (s, 3H), 0.89 (s, 3H). $^{13}$C NMR (101 MHz, CDCl3) δ 175.19, 175.13, 140.81, 137.40, 137.38, 129.44, 127.05, 70.07, 70.04, 65.40, 63.16, 45.03, 44.97, 30.14, 22.33, 18.24. IR $v_{max}$ (cm$^{-1}$): 3387, 1733, 1201, 1164, 1054.

Comparative Example 2 (CE2)

1,3-Dihydroxypropan-2-yl 2-(4-isobutylphenyl)propanoate (IBP-2-MG)

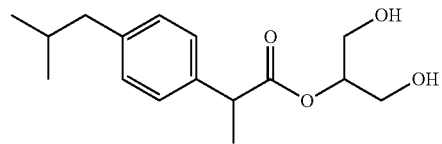 [SMILES: CC(C)Cc1ccc(C(C)C(=O)OC(CO)CO)cc1]

The method described in Davaran and Entezami for the preparation of IBP-2-MG was investigated, however, it was found that IBP-2-MG could not be prepared using the reported method. An alternative synthetic method for the preparation of the title compound was developed as follows:
a) The general procedure for HBTU coupling (Procedure 1) was followed, using ibuprofen (10.00 g, 48.5 mmol), 1,3-O-Benzylidene glycerol (8.74 g, 48.5 mmol), triethylamine (19.62 g, 194 mmol) and HBTU (18.39 g, 48.5 mmol)mmol) in anhydrous DCM (250 mL). The crude product was purified via column chromatography on silica gel (10% EtOAc/pet. spirit, followed by 50% EtOAc/pet. Spirit as eluents) to give 2-phenyl-1,3-dioxan-5-yl 2-(4-isobutylphenyl)propanoate in quantitative yield as a colourless oil. $^1$H NMR (400 MHz, CDCl$_3$) δ 7.44-7.36 (m, 2H), 7.34-7.25 (m, 3H), 7.24-7.19 (m, 2H), 7.06-6.99 (m, 2H), 5.45 (s, 1H), 4.63-4.56 (m, 1H), 4.27-4.18 (m, 1H), 4.13-3.98 (m, 3H), 3.79 (q, J=7.2 Hz, 1H), 2.37 (d, J=7.2 Hz, 2H), 1.84-1.69 (m, 1H), 1.48 (d, J=7.2 Hz, 3H), 0.82 (d, J=6.6 Hz, 7H). $^{13}$C NMR (101 MHz, CDCl$_3$) δ 174.77, 140.60, 137.94, 137.39, 129.33, 129.13, 128.31, 127.29, 126.14, 101.29, 68.98, 68.86, 66.15, 45.07, 30.18, 22.41, 18.44. ESI-MS: m/z 368 (11%, M$^+$, C$_{23}$H$_{28}$O$_4$), 262 (11), 161 (100), 117 (13), 105 (32).

b) The general procedure for the benzylidene acetal/acetonide deprotection (Procedure 5b) was followed, using 2-phenyl-1,3-dioxan-5-yl 2-(4-isobutylphenyl)propanoate (250 mg, 0.678 mmol) and 10% w/w Pd/C (100 mg, 0.094 mmol) in ethanol (25 mL). The title compound, 1,3-dihydroxypropan-2-yl 2-(4-isobutylphenyl)propanoate (IBP-2-MG) was obtained as a colourless gum. $^1$H NMR (400 MHz, CDCl$_3$) δ 7.19 (d, J=8.1 Hz, 2H), 7.09 (d, J=8.1 Hz, 2H), 4.86 (p, J=4.9 Hz, 1H), 3.80-3.69 (m, 3H), 3.63 (d, J=4.8 Hz, 2H), 2.79 (bs, 1H), 2.44 (d, J=7.2 Hz, 2H), 2.36 (bs, 1H), 1.95-1.73 (m, 1H), 1.49 (d, J=7.2 Hz, 3H), 0.88 (s, 3H), 0.89 (s, 3H). $^{13}$C NMR (101 MHz, CDCl$_3$) δ 175.09, 140.91, 137.72, 129.59, 127.10, 75.41, 61.92, 61.83, 45.26, 45.08, 30.25, 22.45, 18.36. IR $v_{max}$ (cm$^{-1}$): 3374, 1717, 1201, 1165, 1053, 1031.

Comparative Example 3 (CE3)

2,3-dihydroxypropyl 2-(2-((2,6-dichlorophenyl)amino)phenyl)acetate (DCF-1-MG)

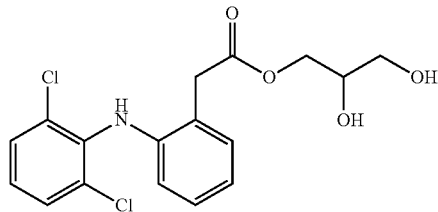 [SMILES: O=C(Cc1ccccc1Nc1c(Cl)cccc1Cl)OCC(O)CO]

a) The general procedure for DCC coupling (Procedure 3) was followed, using diclofenac (10.444 g, 35.3 mmol), DMAP (0.247, 2.0 mmol), solketal (4.50 mL, 36.1 mmol), and DCC (9.107 g, 44.1 mmol) in anhydrous DCM (500 mL). The crude material was purified via column chromatography on silica gel (20% ethyl acetate/hexanes as eluent) to give (2,2-dimethyl-1,3-dioxolan-4-yl)methyl 2-(2-((2,6-dichlorophenyl)amino)phenyl)acetate in 74% yield as a clear yellow oil. $^1$H NMR (200 MHz, CDCl$_3$) δ (ppm) 7.44-7.27 (m, 2H), 7.27-7.18 (m, 1H), 7.18-7.05 (m, 1H), 7.04-6.78 (m, 3H), 6.67-6.38 (m, 1H), 4.45-3.97 (m, 4H), 3.86 (s, 2H), 3.72 (dd, J=8.5, 6.0 Hz, 1H), 1.37 (s, 3H), 1.38 (s, 3H). $^{13}$C NMR (50 MHz, CDCl$_3$) δ 172.18, 142.73, 137.79, 130.85, 129.47, 128.83, 128.06, 124.14, 124.02, 122.05, 118.34, 109.84, 73.46, 66.22, 65.46, 38.34, 26.64, 25.35. ESI-MS: m/z 413 (4%, M$^+$, C$_{20}$H$_{21}$$^{37}$Cl$_2$NO$_4$), 411 (21%, M$^+$, C$_{20}$H$_{21}$$^{37}$Cl$^{35}$ClNO$_4$), 409 (30%, M$^+$, C$_{20}$H$_{21}$$^{35}$Cl$_2$NO$_4$), 394 (11), 242 (20), 214 (100), 103 (27). IR $v_{max}$ (cm$^{-1}$): 3321, 2985, 2935, 1723, 1588, 1504, 1451, 1371, 1252, 1212, 1147, 1089, 1054, 1000, 837, 770.

b) The general procedure for benzylidene acetal/acetonide deprotection (Procedure 5a) was followed, using (2,2-dimethyl-1,3-dioxolan-4-yl)methyl 2-(2-((2,6-dichlorophenyl)amino)phenyl)acetate (3.466 g, 8.4 mmol) in 80% aqueous acetic acid at 80° C. for 5 h. The crude mixture was purified via column chromatography on silica gel using 50% ethyl acetate/hexane as eluent. The title compound, 2,3-dihydroxypropyl 2-(2-((2,6-dichlorophenyl)amino)phenyl)acetate (DCF-1-MG) was obtained in 71% yield as a clear yellow oil. $^1$H NMR (200 MHz, CDCl$_3$) δ (ppm) 7.43-7.03 (m, 4H), 7.03-6.86 (m, 2H), 6.79 (bs, 1H), 6.64-6.45 (m, 1H), 4.32-4.11 (m, 2H), 4.03-3.71 (m, 3H), 3.71-3.41 (m, 2H), 3.36 (s, 2H). $^{13}$C NMR (50 MHz, CDCl$_3$) δ 172.76, 142.68, 137.70, 130.88, 129.55, 128.87, 128.13, 124.18, 123.99, 122.07, 118.27, 70.01, 65.96, 65.85, 63.27, 38.32. ESI-MS: m/z 373 (2%, M$^+$, C$_{17}$H$_{17}$$^{37}$Cl$_2$NO$_4$), 371 (13%, M$^+$, C$_{17}$H$_{17}$$^{37}$Cl$^{35}$ClNO$_4$), 369 (20%, M$^+$, C$_{20}$H$_{21}$$^{35}$Cl$_2$NO$_4$), 279 (11), 277 (16), 241 (32), 214 (100), 180 (16). IR $v_{max}$ (cm$^{-1}$): 3331, 2951, 1720, 1504, 1451, 907, 728.

Comparative Example 4 (CE4)

1,3-dihydroxypropan-2-yl 2-(2-((2,6-dichlorophenyl)amino)phenyl)acetate (DCF-2-MG)

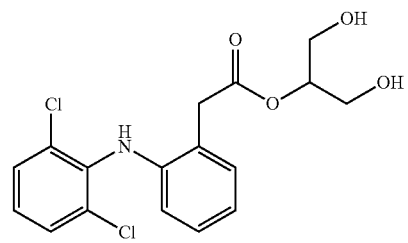 [SMILES: O=C(Cc1ccccc1Nc1c(Cl)cccc1Cl)OC(CO)CO]

a) The general procedure for DCC coupling (Procedure 3) was followed, using diclofenac (11.476 g, 38.7 mmol), DCC (10.013 g, 48.5 mmol), 1,3-O-benzylidene glycerol (6.997 g, 38.8 mmol) and DMAP (0.250 g, 2.0 mmol) in anhydrous DCM (500 mL). The crude mixture was purified via column chromatography on silica gel (20% ethyl acetate/hexanes as eluent) to give 2-phenyl-1,3-dioxan-5-yl 2-(2-((2,6-dichlorophenyl)amino)phenyl)acetate in 68% yield as an off-white solid. $^1$H NMR (200 MHz, CDCl$_3$) δ (ppm) 7.71-7.27 (m, 8H), 7.27-7.09 (m, 1H), 7.09-6.88 (m, 3H), 6.63 (d, J=7.9 Hz, 1H), 5.59 (s, 1H), 4.78 (s, 1H), 4.26 (dd, J=40.1, 12.6 Hz, 4H), 4.01 (s, 2H). $^{13}$C NMR (50 MHz, CDCl$_3$) δ 172.65, 142.88, 137.91, 137.86, 131.09, 129.52, 129.12, 128.90, 128.33, 128.14, 126.10, 124.42, 124.07, 122.19, 118.45, 101.17, 68.92, 66.91, 38.60. ESI-MS: m/z 460 (3%, M$^+$, C$_{24}$H$_{21}$$^{37}$Cl$_2$NO$_4$), 459 (13%, M$^+$, C$_{24}$H$_{21}$$^{37}$Cl$^{35}$ClNO$_4$), 457 (15%, M$^+$, C$_{24}$H$_{21}$$^{35}$Cl$_2$NO$_4$), 242 (11), 214 (100), 103 (15). IR $v_{max}$ (cm$^{-1}$): 3320, 2855, 1717, 1504, 1451, 1142, 1080, 908, 728, 697.

b) The general procedure for benzylidene acetal/acetonide deprotection (Procedure 5b) was followed, using 2-phenyl-1,3-dioxan-5-yl 2-(2-((2,6-dichlorophenyl)amino)phenyl)acetate (3.131 g, 6.8 mmol), 10% w/w palladium on carbon (0.309 g) in ethyl acetate (60 mL). The crude material was purified by precipitation from 30% ethyl acetate/hexanes. The title compound, 1,3-dihydroxypropan-2-yl 2-(2-((2,6-dichlorophenyl)amino)phenyl)acetate (DCF-2-MG) was obtained in 71% yield as an off-white solid. $^1$H NMR (200 MHz, DMSO) δ (ppm) 7.68-7.42 (m, 2H), 7.29-6.91 (m, 4H), 6.91-6.69 (m, 1H), 6.25 (d, J=7.8 Hz, 1H), 4.90-4.62 (m, 3H), 3.79 (s, 2H), 3.65-3.39 (m, 4H). $^{13}$C NMR (50 MHz, DMSO) δ 171.93, 143.27, 137.57, 131.29, 131.21, 131.05, 129.58, 128.12, 126.32, 123.89, 121.12, 116.33, 76.87, 60.15, 37.72. ESI-MS: m/z 373 (2%, M$^+$, C$_{17}$H$_{17}$$^{37}$Cl$_2$NO$_4$), 371 (12%, M$^+$, C$_{17}$H$_{17}$$^{37}$Cl$^{35}$ClNO$_4$), 369 (18%, M$^+$, C$_{20}$H$_{21}$$^{35}$Cl$_2$NO$_4$), 295 (4), 279 (11), 277, (16), 242 (29), 216 (37) 214 (100), 180 (13). IR $v_{max}$ (cm$^{-1}$): 3285, 2943, 1708, 1579, 1509, 1450, 1289, 1046, 770, 743.

Preparation of Polymer-NSAID Conjugates and NSAID Delivery Systems

GPC analysis was performed on a Shimadzu liquid chromatography system fitted with a Wyatt Dawn Heleos LS detector (λ=658 nm), a Shimadzu RID-10 refractometer (λ=633 nm) and a Shimadzu SPD-20A UV-Vis detector, using three identical PL gel columns (5 mm, MIXED-C) in series and HPLC-grade THF (45° C., 1 mL/min) as the mobile phase. Astra software (Wyatt Technology Corp.) was used to determine the molecular weight characteristics from injected mass by assuming 100% mass recovery. Note: some samples gave high signal to noise ratio light scattering profile, and hence the MW was obtained from linear polystyrene conventional calibration.

General Preparation Methods:

Polymer-NSAID Conjugates with Polyurethane Backbone

Method A1: Polymer-NSAID conjugates comprising a polyurethane polymer backbone were prepared by adding diisocyanate to either a stirred suspension or solution of a selected NSAID-monomer conjugate (amounts as outlined in Table 1 or Table 2) in dry toluene at room temperature in a Schlenk tube under an inert gas (Ar or $N_2$) atmosphere. To this was added dibutyltindilaurate (DBTDL) (catalytic, ~0.1 eq.). The tube was sealed and the reaction mass was placed in an oil bath pre-heated at 80° C. The contents of the tube were allowed to stir at 80° C. for 16-28 h. The reaction tube was allowed to cool to room temperature and the solvent was removed under reduced pressure. The residue was dissolved in an appropriate solvent or mixture of solvents (e.g. DCM, toluene, toluene/acetonitrile) and added to a stirred solution of diethyl ether (DEE) (20 times excess) in a centrifuge tube. The mixture was centrifuged for 5 to 10 mins (at $4.4 \times 10^3$ rpm) and the solvent decanted off. The product was washed twice with DEE by each time placing on a vortex mixer for at least one minute and then the mixture was centrifuged and the solvent decanted from the residue. The residue was then dried in vacuo to obtain the desired polymer drug conjugate.

Method A2: Following the same procedure as Method A1 using dry tetrahydrofuran (THF) (10% w/w) as reaction solvent and heating at 50° C. After the reaction was complete the reaction solution was precipitated into a stirred solution of diethyl ether (DEE) (20 times excess) in a centrifuge tube. The mixture was centrifuged for 5-10 mins (at $4.4 \times 10^3$ rpm) and the solvent decanted off. The product was purified further by redissolving the solid in 1 mL of DCM, followed by addition of 47 mL of DEE to precipitate the solid which was then centrifuged and the solvent decanted from the residue. This process was repeated twice. The residue was then dried in vacuo to obtain the desired polymer drug conjugate.

Polymer-NSAID Conjugates Comprising a Hydrophilic Component as Part of the Polymer Backbone The methods described below introduce a hydrophilic group as a hydrophilic component in the polymer backbone. The hydrophilic component is introduced by polymerising a hydrophilic co-monomer with a drug-monomer conjugate.

Method B1: Polymer-NSAID conjugates were prepared by adding diisocyanate (~1.0 eq.) to either a stirred suspension or solution of a selected NSAID-monomer conjugate (X eq.) and a desired hydrophilic co-monomer (Y eq.) in dry toluene at room temperature in a Schlenk tube under an inert gas (Ar or $N_2$) atmosphere, such that the combined amounts of NSAID-monomer conjugate and hydrophilic co-monomer is 1.0 eq. (X+Y=1.0) (amounts as outlined in Table 1 or Table 2). To this was added dibutyltindilaurate (DBTDL) (catalytic, ~0.1 eq.). The tube was sealed and the reaction mass was placed in an oil bath pre-heated at 80° C. The contents of the tube were allowed to stir at 80° C. for 16-28 h. The reaction tube was allowed to cool to room temperature and the solvent was removed under reduced pressure. The residue was dissolved in an appropriate solvent or mixture of solvents (e.g. DCM, toluene, toluene/acetonitrile) and added to a stirred solution of diethyl ether (DEE) in a centrifuge tube. The mixture was centrifuged for 5 mins and the solvent decanted off. The product was washed twice with DEE by each time placing on a vortex mixer for at least one minute and then the mixture was centrifuged and the solvent decanted from the residue. The residue was then dried in vacuo to obtain the desired polymer drug conjugate.

Method B2: Following the same procedure as Method B1 using dry tetrahydrofuran (THF) as reaction solvent and heating at 50° C. for 16-28 h. At the completion of the reaction the reaction tube was allowed to cool to room temperature and the solvent was concentrated under reduced pressure and the reaction solution was precipitated into a stirred solution of diethyl ether (DEE) (20 times excess) in a centrifuge tube. The mixture was centrifuged for 5 to 10 mins (at $4.4 \times 10^3$ rpm) and the solvent decanted off. The product was purified further by redissolving the solid in 1 mL of DCM, followed by addition of 47 mL of DEE to precipitate the solid which was then centrifuged and the solvent decanted from the residue. This process was repeated twice. The residue was then dried in vacuo to obtain the desired polymer drug conjugate.

Polymer-NSAID Conjugates Blended with Hydrophilic Component

The below method introduces a hydrophilic component by blending a hydrophilic polymer with a polymer drug conjugate.

Method C: A polymer-NSAID conjugate prepared according to the invention is dissolved in THF or DCM. A hydrophilic polymer (as a hydrophilic component) is added and the mixture is stirred for 1 h. The solvent is removed under reduced pressure and the process is repeated to provide a system containing a polymer-NSAID conjugate blended with a hydrophilic component.

Preparation of Polymer Rods

Polymer-NSAID conjugates or NSAID delivery systems prepared in accordance with Method A1, A2, B1, B2 or C were melt extruded into rods at a suitable temperature and at 5 mL/min using a micro extruder. The resulting polymer rods were tested for in vitro drug release, as discussed below.

Polymer-NSAID Conjugates

Polymer-NSAID conjugates were prepared with monomer-NSAID conjugates having an NSAID conjugated via an aryl ester. The polymer-NSAID conjugates (prepared with or without a hydrophilic co-monomer) are shown in Table 2.

TABLE 2

Polymer-NSAID conjugates prepared with various NSAID-monomer conjugates and co-monomers

| Example No | NSAID | NSAID-monomer conjugate (mg) | Co-Monomer (mg) | Diisocyanate (mg) | Method | Comments | Extrusion Temp (° C.) | Extrusion Diameter (mm) |
|---|---|---|---|---|---|---|---|---|
| 11 | Diclofenac | DCF-PHB-2-MG (750) | — | ELDI (352) | A1 | Light pink coloured MW = 28800 Da PDI = 1.437 | 85 | 0.7 |
| 12 | Diclofenac | DCF-PHB-2-MG (100) | — | ELDI (52) | A1 | White flaky solid MW = 57580 Da PDI = 1.245 | NA | NA |
| 13 | Diclofenac | DCF-PHB-2-MG (101) | PEG 3000 (204) | ELDI (67) | B1 | Pink coloured waxy solid MW = 42820 Da PDI = 1.255 | NA | NA |
| 14 | Diclofenac | DCF-PHB-2-MG (1800) | PEG 3000 (3668) | ELDI (1204) | B1 | Light pink solid MW = 36880 Da PDI = 1.302 | 33 | 1.0 |
| 15 | Diclofenac | DCF-PHB-2-MG (150) | PEG 3000 (91) | ELDI (82) | B1 | Yield: 0.273 g | 30 | 1.0 |
| 16 | Diclofenac | DCF-PHB-2-MG (100) | PEG 3000 (122) | ELDI (61) | B1 | Pink coloured waxy solid MW = 41580 Da PDI = 1.193 Yield: 0.25 g | 28 | 1.0 |
| 17 | Diclofenac | DCF-PHB-2-MG (101) | PEG 3000 (611) | ELDI (95) | B1 | MW = 58080 Da PDI = 1.477 | NA | NA |
| 18 | Diclofenac | DCF-PHB-2-MG (100) | PEG 200 (61.2) | ELDI (115) | B2 | MW = 18.2 kDa, PDI = 1.68, Yield = 80 mg | — | — |
| 19 | Diclofenac | DCF-PHB-2-MG (100) | PEG 1000 (61.2) | ELDI (60.0) | B2 | MW = 15.1 kDa, PDI = 1.54, Yield = 112 mg | — | — |
| 20 | Diclofenac | DCF-PHB-2-MG (100) | PEG 3000 (61.2) | HDI (37.7) | B2 | MW = 10.9 kDa, PDI = 1.20, Yield = 82.7 mg | — | — |
| 21 | Diclofenac | DCF-PHB-2-MG (196) | PLGA 1173 (75:25) (159) | ELDI (131) | B1 | Mn = 7.01 KDa PDI = 1.2 Yield = 0.302 g | 85 | 1.0 |
| 22 | Diclofenac | DCF-PHB-2-MG (184) | PLGA 1175 (47:53) (145) | ELDI (125) | B1 | Mn = 7.23 KDa PDI = 1.234 Yield = 0.293 g | 80 | 1.0 |
| 23 | Diclofenac | DCF-PHB-2-MG (201) | PDOO1200 (98) | ELDI (122) | B1 | MW = 6.422 KDa, PDI = 2.08 Yield = 362 mg | 85 | 1.0 |
| 24 | Diclofenac | DCF-PHB-2-MG (202) | PDOO 700 (57) | ELDI (122) | B1 | MW = 5.717 KDa PDI = 2.022, Yield = 288 mg | 80-85 | 1.0 |
| 25 | Diclofenac | DCF-PHB-2-MG (200) | PLA876 (117) | ELDI (134) | B1 | Mn = 6.62 KDa Yield = 0.24 g | 92 | 01.0 |
| 26 | Diclofenac | DCF-PHB-2-MG (103) | PCLD (70) | ELDI (67) | B1 | Mn = 9.8 KDa Yield = 0.168 g | 50 | 1.0 |
| 30 | Diclofenac | DCF-PHB-2-MG (100) | PEG 1000 (69) | ELDI (64) | B1 | Light pink sticky solid Mw = 52.78 kDa, PDI = 1.208, Yield = 204.5 mg | NA | NA |

TABLE 2-continued

Polymer-NSAID conjugates prepared with various NSAID-monomer conjugates and co-monomers

| Example No | NSAID | NSAID-monomer conjugate (mg) | Co-Monomer (mg) | Diisocyanate (mg) | Method | Comments | Extrusion Temp (° C.) | Extrusion Diameter (mm) |
|---|---|---|---|---|---|---|---|---|
| 31 | Diclofenac | DCF-PHB-2-MG (101) | PEG 1000 (203) | ELDI (95) | B1 | Pale pink sticky solid Mw = 51.57 kDa, PDI = 1.195, yield = 440 mg | NA | NA |
| 32 | Diclofenac | DCF-PHB-2-MG (101) | PEG 1000 (199) | ELDI (92) | B1 | Pale pink sticky solid Mw = 28.11 kDa, PDI = 1.193, yield = 407 mg | NA | NA |
| 33 | Diclofenac | DCF-PHB-1-MG | — | ELDI | A1 | — | | |
| 34 | Ibuprofen | IBP-PHB-2-MG (100) | — | ELDI (56.5) | A2 | Mw = 8.95 kDa, PDI = 1.22, Yield: 19.7 mg | — | — |
| 35 | Diclofenac | DCF-PHB-2MG (150) | PEG 3000 (45.8) | ELDI (76.1) | B2 | Yellowish, crystalline solid MW = 10.6 kDa, PDI = 1.02, Yield = 159 mg | 55 | 1.0 |
| 36 | Diclofenac | DCF-PHB-2MG (147) | PEG 3000 (57.6) | ELDI (72.4) | B2 | Yellowish, semi-crystalline solid MW = 7.79 kDa PDI = 1.32 Yield = 168 mg | 55 | 1.0 |
| 37 | Diclofenac | DCF-PHB-2MG (150) | PEG 3000 (69.1) | ELDI (74.4) | B2 | Yellowish, tacky solid MW = 13.5 kDa PDI = 1.16 Yield = 209 mg | | |
| 38 | Diclofenac | DCF-PHB-2MG (144) | PEG 3000 (76.8) | ELDI (72.4) | B2 | Yellowish, tacky solid MW = 12.7 kDa PDI = 1.02 Yield = 168 mg | | |
| 39 | Diclofenac | DCF-PHB-2MG (150) | PEG 3000 (91.8) | ELDI (81.7) | B2 | Yellowish, tacky solid MW = 8.67 kDa PDI = 2.00 Yield = 237 mg | | |
| 40 | Indomethacin | IND-PHB-2MG (58.6) | PEG 3000 (35.3) | ELDI (26.6) | B2 | Yellow soft solid MW = 21.1 kDa PDI = 1.64 Yield = 129 mg | | |
| 41 | Indomethacin | IND-PHB-1MG (90.0) | PEG 3000 (54.2) | ELDI (40.8) | B2 | Yellow soft solid MW = 9.83 kDa PDI = broad Yield = 129 mg | | |

TABLE 2-continued

Polymer-NSAID conjugates prepared with various NSAID-monomer conjugates and co-monomers

| Example No | NSAID | NSAID-monomer conjugate (mg) | Co-Monomer (mg) | Diisocyanate (mg) | Method | Comments | Extrusion Temp (° C.) | Extrusion Diameter (mm) |
|---|---|---|---|---|---|---|---|---|
| 42 | Diclofenac | DCF-PHB-THE (88.0) | PEG 3000 (56.6) | ELDI (42.7) | B2 | Very tacky brown solid MW = 3.60 kDa PDI = 1.29 Yield = 125 mg | | |
| 43 | Ketorolac | KTC-PHB-2MG (60.8) | PEG 3000 (45.1) | ELDI (34.0) | B2 | Brown, soft solid MW = 21.7 kDa PDI = 1.29 Yield = 106 mg | | |
| 44 | Diclofenac | DCF-PHB-THE (76.2) | PEG 3000 (49.0) | HDI (27.5) | B2 | Whitish soft solid Mw = 6.48 kDa; PDI = 2.46 Yield = 127 mg | | |
| 45 | Ketorolac | KTC-PHB-1MG (144) | PEG 3000 (107) | ELDI (80.4) | B2 | Pale brown, soft solid Mw = 5.90 kDa; PDI = 1.25 Yield = 308 μγ | | |
| 46 | Diclofenac | DCF-PHB-2MG (100) and DCF-2MG (75.5) | PEG 3000 (136) | ELDI (103) | B2 | Pale brown soft solid Yield = 318 mg MW = 12.4 kDa, PDI = 1.28 | | |
| 47 | Diclofenac | DCF-Phloroglucinol (70.0) | PEG 3000 (57.7) | ELDI (43.5) | B2 Using DABCO as catalyst | Brownish red soft solid Yield = 74.8 mg MW = 7.54 kDa, PDI = 1.31 | | |
| 48 | Diclofenac | DCF-PHB-2MG (142) | PEG 1000 (99.4) | ELDI (88.0) | B2 | Yellowish, tacky solid Yield = 207 mg MW = 5.29 kDa, PDI = 2.32 | | |
| 49 | Diclofenac | DCF-PHB-2MG (141) | PEG 200 (109) | ELDI (188) | B2 | Yellowish tacky solid Yield = 310 mg MW = 2.24 kDa, PDI = 3.92 | | |
| 50 | Diclofenac | DCF-PHB-2MG (141.1) | EG (135) | ELDI (558) | B2 | Crystalline white solid Yield = 566 mg MW = 10.8 kDa, PDI = 1.61 | 50 | 1.0 |
| 51 | Diclofenac | DCF-PHB-2-MG (105.2) | — | DIVDIP (85.1) | A1 | Light red solid Mw = 17 kDa Yield = 120 mg | 80 | 1.0 |
| 52 | Diclofenac | DCF-PHB-2-MG (150) | EG (19) | HDI (103) | B2 | Mw = 26.2 kDa, PDI = 1.12 | 50-60 | 1.0 |
| 53 | Diclofenac | DCF-PHB-2-MG (150) | — | HDI (51.5) | A2 | Mw = 27.4 kDa, PDI = 1.28 | 60 | 1.0 |

TABLE 2-continued

Polymer-NSAID conjugates prepared with various NSAID-monomer conjugates and co-monomers

| Example No | NSAID | NSAID-monomer conjugate (mg) | Co-Monomer (mg) | Diisocyanate (mg) | Method | Comments | Extrusion Temp (° C.) | Extrusion Diameter (mm) |
|---|---|---|---|---|---|---|---|---|
| 54 | Diclofenac | DCF-PHB-2-MG (150) | PEG200 (61.2) | HDI (103) | B2 | Mw = 39.7 kDa, PDI = 1.29 | 60 | 1.0 |
| 55 | Diclofenac | DCF-PHB-2-MG (150) | PEG3000 (91.8) | HDI (56.6) | B2 | Mw = 76.2 kDa, PDI = 1.13 | 60 | 1.0 |
| 56 | Diclofenac | DCF-PHB-2-MG (150) | PEG1000 (306) | HDI (103) | B2 | Mw = 32.5 kDa, PDI = 1.08 | — | — |
| 57 | Ibuprofen | IBP-PHB-2-MG (100) | PEG200 (50) | ELDI (113) | B2 | Mw = 22.7 kDa, PDI = 1.22 | | |
| 58 | Ibuprofen | IBP-PHB-2-MG (100) | EG (15.5) | ELDI (113) | B2 | Mw = 22.1 kDa, PDI = 1.29 | 50 | 0.5 |
| 59 | Diclofenac | DCF-PHB-2-MG (100) | EG (86.1) | ELDI (360) | B2 | Mw = 9.06 kDa, PDI = 1.53 | | |
| 60 | Diclofenac | DCF-PHB-2-MG (100) | — | ELDI (46) | A2 | Mw = 5.42 kDa, PDI = 1.24 | 40-63 | 0.5 |
| 61 | Diclofenac | DCF-PHB-2-MG (192.9) | GMA (52.8) | ELDI (188.5) | A1 | Mw = 6.85 kDa, PDI = 1.38 | 80 | 1.0 |
| 62 | Diclofenac | DCF-PHB-2-MG (198.5) | GMA (108.6) | ELDI (285) | A1 | Mw =7.89 kDa, PDI = 2.12 | 75 | 1.0 |
| 63 | Ibuprofen | IBP-PHB-2-MG (100) | PEG3000 (75) | ELDI (62) | B2 | Mw =22.7 kDa, PDI = 1.22 | 50° C. | 0.5 |
| 64 | Diclofenac | DCF-PHB-2-MG (150) | PEG3000 (18.3) | ELDI (74.1) | B1 | — | | |
| 65 | Ibuprofen | IBP-PHB-1-MG (121) | PEG3000 (101) | ELDI (76.2) | B2 | Mw = 10-15 kDa | | |
| 66 | Diclofenac | DCF-PHB-2-MG (116) | GMH (44.1) | ELDI (107) | B2 | Mw = 3.93 kDa PDI = 1.11 Yield = 185 mg | | |

DABCO = 1,4-diazabicyclo[2.2.2]octane
GMA = glycerol monoacetate
GMH = glycerol monohexynoate = 1,3-dihydroxypropan-2-yl hex-5-ynoate Comparative Polymer-NSAID Conjugates Comparative polymer-NSAID conjugates were prepared with comparative monomer conjugates having an NSAID conjugated via an alkyl ester rather than an aryl ester. The comparative polymer-NSAID conjugates (prepared with or without a hydrophilic co-monomer) are shown in Table 3.

TABLE 3

Comparative Polymer-NSAID conjugates prepared with comparative NSAID-monomer conjugates and comonomers

| Example No. (CE) | NSAID | Comparative NSAID-monomer conjugate (mg) | Co-Monomer (mg) | Diisocyanate (mg) | Method | Comments | Extrusion Temp (° C.) | Extrusion Diameter (mm) |
|---|---|---|---|---|---|---|---|---|
| CE5 | Ibuprofen | IBP-1-MG (230) | - | HDI (138) | A1 | White solid polymer MW = 21.5 kDa, PDI 1.42 Yield = 97.7 mg | 80 | 0.5 |

TABLE 3-continued

Comparative Polymer-NSAID conjugates prepared with comparative NSAID-monomer conjugates and comonomers

| Example No. (CE) | NSAID | Comparative NSAID-monomer conjugate (mg) | Co-Monomer (mg) | Diisocyanate (mg) | Method | Comments | Extrusion Temp (° C.) | Extrusion Diameter (mm) |
|---|---|---|---|---|---|---|---|---|
| CE6 | Ibuprofen | IBP-1-MG (230) | ethylene glycol (45) | HDI (246) | B1 | White solid polymer MW = 5.25 kDa, PDI = 1.24, Yield = 291 mg | 80 | 0.5 |
| CE7 | Ibuprofen | IBP-1-MG (215) | PEG 200 (153) | HDI (258) | B1 | White solid polymer MW = 4.16 kDa, PDI = 1.30, Yield = 272 mg | 80 | 0.5 |
| CE8 | Diclofenac | DCF-2-MG (500) | - | ELDI (315) | A1 | MW = 185200 | 125 | 0.7 |
| CE9 | Diclofenac | DCF-2-MG (100) | - | ELDI (63) | A1 | MW = 251,900 | NA | NA |
| CE10 | Diclofenac | DCF-1-MG (975) | - | ELDI (647) | A1 | MW = 60,440 *Before precip | 95 | 0.7 |
| CE11 | Diclofenac | DCF-1-MG (975) | - | ELDI (647) | A1 | MW = 225,700*After precip | 95 | 0.7 |
| CE12 | Diclofenac | DCF-1-MG (99.2) | - | HDI (37.8) | A1 | Mw = 29.18 kDa, PDI = 1.232 | - | - |
| CE13 | Ibuprofen | IBP-1-MG (3000) | - | HDI (1799) | A1 | MW = 2.75 kDa PDI = 1.18, Yield = 2.009 g (Catalyst =TEA) | - | - |
| CE14 | Ibuprofen | IBP-1-MG (3000) | PEG200 (2140) | HDI (3600) | A1 | MW = 65.2 kDa, PDI = 5.87 Yield = 1.400 g (Catalyst = Benzyl chloride) | - | - |

NSAID Delivery System

A hydrophilic component is blended with various polymer-NSAID conjugates of Table 2 or comparative polymer-NSAID conjugates of Table 3. Drug delivery systems comprising the blends are shown in Tables 4 and 5, respectively.

TABLE 4

Polymer-NSAID conjugates blended with Hydrophilic Component

| Example No | NSAID | Polymer-NSAID Conjugate Example No (mg) | Hydrophilic Component (mg) | Method | Extrusion Temp (° C.) | Extrusion Diameter (mm) |
|---|---|---|---|---|---|---|
| 67 | Diclofenac | Example 11 (144) | PEG 3000 (300) | C | 40-45 | 1.0 |

TABLE 5

Comparative Polymer-NSAID conjugates blended with Hydrophilic Component

| Example No | NSAID | Polymer-NSAID Conjugate Example No (mg) | Hydrophilic Component (mg) | Method | Extrusion Temp (° C.) | Extrusion Diameter (mm) |
|---|---|---|---|---|---|---|
| CE15 | Diclofenac | CE8 (314) | PEG 1000 (117) | C | 50 | 1.0 |

Polymer Biodegradation:

The extent of polymer biodegradation can be determined gravimetrically by weighing rod samples prior to and at the end of each biodegradation experiment. A sample is incubated in isotonic phosphate buffer (IPB), adjusted to pH 7.4 using orthophosphoric acid and containing 0.01% sodium azide as a preservative, and incubated at 37° C. with continuous stirring for the desired period of incubation. At the end of the incubation period, the sample is washed with distilled water and dried to constant weight.

Calculation of mol % of PEG:

If a polymer is comprised of components A, B, C and D then the amount of component A (as a % by mole) is $$100*n(A)/[n(A)+n(B)+n(C)+n(D)]$$

More specifically if a NSAID-polymer conjugate is comprised of a drug-monomer construct, a diisocyanate co-monomer and a co-polymer. The amount (mol %) of co-polymer present in the NSAID-polymer conjugates can be defined as $$100*n(\text{co-polymer})/[n(\text{drug-monomer})+n(\text{diisocyanate})+n(\text{co-polymer})]$$

And the amount (mol %) of PEG present in the NSAID-polymer conjugates is defined as $$100*n(\text{PEG})/[n(\text{drug-monomer})+n(\text{diisocyanate})+n(\text{PEG})]$$

Residue Test:

Residue testing was conducted for all polymer-NSAID conjugates assessed for in vitro drug release to ascertain how much free (unconjugated) NSAID drug or NSAID-monomer conjugate is present in the polymer conjugate.

(a) Diclofenac

To quantify the amount of unreacted diclofenac, diclofenac-monomer or diclofenac lactam in the final NSAID drug-polymer conjugate an accurately weighed sample of the diclofenac-polymer conjugate was dissolved in 1.0 mL of DMF in a 10.0-mL volumetric flask and made up to volume with acetonitrile. 5.0 mL of this solution was further diluted to 10.0 mL with IPB pH 7.4, and subsequently filtered through a 0.45-µm membrane filter and analysed by HPLC.

(b) Ibuprofen

To quantify the amount of unreacted ibuprofen and ibuprofen-monomer, approximately 10 mg of ibuprofen-polymer conjugate was accurately weighed and dissolved in 1.0 mL of DMF in a 10-mL volumetric flask and made up to volume with acetonitrile. 5.0 mL of this solution was diluted to 10.0 ml with Milli-Q water. An aliquot of the resulting suspension was filtered with a 0.45 µm filter and analysed by HPLC.

(c) Ketorolac and Indomethacin

To quantify the amount of unreacted NSAID and NSAID-monomer, a known amount of the NSAID drug-polymer conjugate was weighed accurately into a 5-ml volumetric flask, dissolved in 0.5 ml DMF under sonication and made up to 5 ml volume with acetonitrile. This solution was diluted 1:1 with $H_2O$ or isotonic phosphate buffer pH 2.5, filtered through a 0.45 µm syringe filter, and analysed by HPLC.

Discussion of Results:

The results of residue testing for various polymer-NSAID conjugates in accordance with the invention are shown in Table 6. The results of residue testing for various Comparator polymer-NSAID conjugates are shown in Table 7. The residue test results consistently show low levels of free NSAID or unreacted NSAID monomer in the polymer-NSAID conjugates. In all of the examples of the invention shown in FIGS. 1 to 13 and shown in Table 9 the release of drug cannot be accounted for by the levels of residual NSAID or residual NSAID monomer and therefore must be from the pendant NSAID conjugated to the polymer backbone via the aryl ester.

TABLE 6

Results of residue testing for Polymer-NSAID conjugates

| Example No | NSAID | % NSAID (w/w) | % monomer (w/w) |
|---|---|---|---|
| 61 | Diclofenac | 0.15 | <0.14 |
| 17 | Diclofenac | 0.31 | <0.14 |
| 13 | Diclofenac | 0.17 | <0.14 |
| 15 | Diclofenac | <0.11 | <0.14 |
| 16 | Diclofenac | 0.19 | <0.14 |
| 18 | Diclofenac | 0.31 | <0.14 |
| 19 | Diclofenac | 0.19 | <0.14 |
| 34 | Ibuprofen | <0.20 | <0.20 |
| 35 | Diclofenac | <0.11 | <0.14 |
| 36 | Diclofenac | <0.11 | <0.14 |
| 37 | Diclofenac | <0.11 | <0.14 |
| 38 | Diclofenac | <0.11 | <0.14 |
| 39 | Diclofenac | <0.11 | <0.14 |
| 40 | Indomethacin | <0.03 | <0.03 |
| 41 | Indomethacin | <0.03 | <0.03 |
| 43 | Ketorolac | 0.27 | <0.08 |
| 44 | Diclofenac | 0.09 | <0.14 |
| 45 | Ketorolac | 0.17 | <0.08 |
| 47 | Diclofenac | <0.11 | <0.14 |
| 52 | Diclofenac | 0.36 | <0.14 |
| 54 | Diclofenac | 0.39 | <0.14 |
| 55 | Diclofenac | 0.26 | <0.14 |
| 56 | Diclofenac | 0.65 | <0.14 |
| 58 | Ibuprofen | <0.20 | <0.20 |
| 59 | Diclofenac | 0.12 | <0.14 |
| 60 | Diclofenac | 0.19 | <0.14 |
| 63 | Ibuprofen | <0.20 | <0.20 |

TABLE 7

Results of residue testing for Comparative Polymer-NSAID conjugates

| Example No | NSAID | % NSAID (w/w) | % monomer (w/w) |
|---|---|---|---|
| CE5 | Ibuprofen | <0.20 | <0.20 |
| CE6 | Ibuprofen | <0.20 | <0.20 |
| CE7 | Ibuprofen | <0.20 | <0.20 |
| CE10 | Diclofenac | 0.27 | <0.16 |
| CE15 | Diclofenac | <0.27 | <0.16 |

Drug Release Procedure:

Following in vitro release guidelines recommended by the International Organisation of Standardisation [Bhavesh Vaghela, Rajan Kayastha, Nayana Bhatt, Nimish Pathak and Dashrath Rathod, Journal of Applied Pharmaceutical Science 01 (03); 2011: 50-56], polymer rods were suspended in wire baskets which were immersed in isotonic phosphate buffer (IPB), adjusted to pH 7.4 using orthophosphoric acid and containing 0.01% sodium azide as a preservative, and incubated at 37° C. with continuous stirring. Aliquots of the receptor solution were removed for analysis by HPLC at predetermined time points until the release from the polymer no longer increased.

HPLC Analysis:

The amount of NSAID or NSAID-monomer measured from the samples taken during the residue test and samples taken at the various time points during drug release was quantified by reverse phase high performance liquid chromatography (HPLC) with a UV absorbance detector. The chromatographic conditions and detection wavelength used in each assay are summarised in the following Table 8.

TABLE 8

| | Column | Mobile Phase | Flow Rate (mL/min) | Wavelength (nm) | Retention Times |
|---|---|---|---|---|---|
| Ibuprofen | C18 bonded reversed phase 5 μm particles, 3.9 (i.d.) × 150 mm | Acetonitrile: 20 mM disodium hydrogen phosphate aqueous solution (60:40 v/v) | 1.0 | 230 | IBP-MG: 3.320 mins, IBP: 5.400 mins IBP-PHB-MG: 6-7 mins |
| Diclofenac | C18 bonded reversed phase 5 μm particles, 3.9 (i.d.) × 150 mm | Acetonitrile:water: acetic acid solution (55:45:1) | 1.0 | 275 (diclofenac) and 245 (monomer) | DCF: 6.500 mins DCF-PHG-MG: 7.410 mins |
| Indomethacin | C18 bonded reversed phase, 5 μm particles, 4.6 (i.d.) × 150 mm | acetonitrile/water 57:43, 0.6% triethylamine, adjusted to pH 3.5 with phosphoric acid | 1.0 | 254 | IND: 5.6 min (IND), IND-PHB-MG: 7.0 min |
| Ketorolac | C18 bonded reversed phase, 5 μm particles, 4.6 (i.d.) × 150 mm | acetonitrile/water 45:55, 0.6% triethylamine, adjusted to pH 3.0 with phosphoric acid | 1.0 | 313 | KTC: 4.5 min, KTC-PHB-MG: 6.7 min |

The ibuprofen HPLC method is a modification of the method described by Farrar, H.; Letzig, L.; Gill, M., Journal of Chromatography B 2002, 780 (2), 341-348. The diclofenac HPLC method is a modification of the method described by Jilani, J. A.; Pillai, G. K.; Salem, M. S.; Najib, N. M., Drug Dev. Ind. Pharm. 1997, 23 (3), 319. The indomethacin HPLC method is a modification of the method described by Singh, A. K., Jang, Y., Mishra, U., Granley, K. J. Chromatograph. B Biomed. Sci. App. 1991, 568(2), 351-361. The ketorolac HPLC method is a modification of the method described by Flores-Murrieta, F. J., Granados-Soto, V., Castañeda-Hernández, G., Herrera, J. E., Hong, E. Biopharm. Drug Disposition 1994, 15(2), 129-136.

Release of the Relevant NSAID from Polymer-NSAID Conjugates:

The in vitro release of the NSAID from various polymer systems described in Tables 2 and 4 is shown in Table 9 and the accompanying Figures and discussed below.

The amount of NSAID released was determined by HPLC as described above at the time intervals given in the charts shown in the Figures.

TABLE 9

Summary of results from drug release study for rods prepared with various NSAID-polymer conjugates (either alone or blended with a hydrophilic component) when placed in isotonic phosphate buffer (pH 7.4) at 37° C.

| Polymer Example No | NSAID | Sample Mass (mg) | Release Rate (μg/24 hours) | Study period (days) |
|---|---|---|---|---|
| 13 | Diclofenac | 6.2 | 32.8 | 8 |
| 15 | Diclofenac | 6.9 | 26.2 | 30 |
| 16 | Diclofenac | 5.5 | 29.9 | 15 |
| 17 | Diclofenac | 5.8 | 15.9 | 4 |
| 18 | Diclofenac | 12.5 | 10.5 | 90 |
| 19 | Diclofenac | 9.9 | 13.1 | 45 |
| 30 | Diclofenac | 6.0 | 34.8 | 15 |

TABLE 9-continued

Summary of results from drug release study for rods prepared with various NSAID-polymer conjugates (either alone or blended with a hydrophilic component) when placed in isotonic phosphate buffer (pH 7.4) at 37° C.

| Polymer Example No | NSAID | Sample Mass (mg) | Release Rate (μg/24 hours) | Study period (days) |
|---|---|---|---|---|
| 31 | Diclofenac | 6.4 | 29.0 | 10 |
| 32 | Diclofenac | 5.6 | 33.5 | 8 |
| 35 | Diclofenac | 9.6 | 37.3 | 15 |
| 36 | Diclofenac | 8.6 | 37.1 | 15 |
| 37 | Diclofenac | 10.5 | 44.9 | 15 |
| 38 | Diclofenac | 13.3 | 59.7 | 15 |
| 39 | Diclofenac | 10.3 | 51.1 | 15 |
| 40 | Indomethacin | 10.7 | 30.7 | 9 |
| 41 | Indomethacin | 11.3 | 31.6 | 9 |
| 43 | Ketorolac | 9.7 | 150 | 9 |
| 44 | Diclofenac | 12.4 | 79.5 | 6 |
| 45 | Ketorolac | 10.2 | 195 | 6 |
| 47 | Diclofenac | 9.4 | 19.9 | 4 |
| 52 | Diclofenac | 7.9 | 0.55 | 136 |
| 54 | Diclofenac | 8.9 | 12.6 | 91 |
| 55 | Diclofenac | 9.7 | 61.8 | 15 |
| 56 | Diclofenac | 7.6 | 31.3 | 15 |
| 57 | Ibuprofen | 7.0 | 1.48 | 65 |
| 58 | Ibuprofen | 5.0 | 0.19 | 122 |
| 59 | Diclofenac | 11.7 | 2.5 | 113 |
| 63 | Ibuprofen | 5.5 | 1.6 | 122 |
| 67 | Diclofenac | 8.1 | 0.65 | 120 |

COMPARATIVE EXAMPLES

No Release of NSAID

An investigation of the in vitro release of the NSAID from various comparative polymer systems described in Tables 3 and 5 is shown in Table 10. The comparative polymer systems are prepared with NSAID-monomer conjugates where the NSAID is conjugated via an alkyl ester.

TABLE 10

Summary of results from drug release study for rods prepared with various Comparative NSAID-polymer conjugates (either alone or blended with a hydrophilic component) when placed in isotonic phosphate buffer (pH 7.4) at 37° C.

| Polymer Example No | NSAID | Sample Mass (mg) | Release Rate (µg/24 hours) | Study period (days) |
|---|---|---|---|---|
| CE6 | Ibuprofen | 6.3 | 0 | 60 |
| CE7 | Ibuprofen | 5.6 | 0 | 60 |
| CE8 | Ibuprofen | 8.7 | 0 | 30 |
| CE10 | Diclofenac | 1.0 | 0 | 30 |
| CE15 | Diclofenac | 30.5 | 0 | 45 |

FIG. 1 shows the effect of both an aryl ester linkage and the presence of a hydrophilic component to NSAID release. The data demonstrates that conjugated of the drug via an aryl ester is an essential feature of the polymer conjugates of the invention, as NSAID release was not observed with a comparative polymer-NSAID where the drug is not conjugated via aryl ester to the polymer backbone. The data also shows a hydrophilic component can help achieve immediate release of NSAID from the conjugate. The release of the NSAID diclofenac also continued at a steady rate for the duration of the study, whereas, no release of diclofenac is seen with the comparative example.

Figure 2:
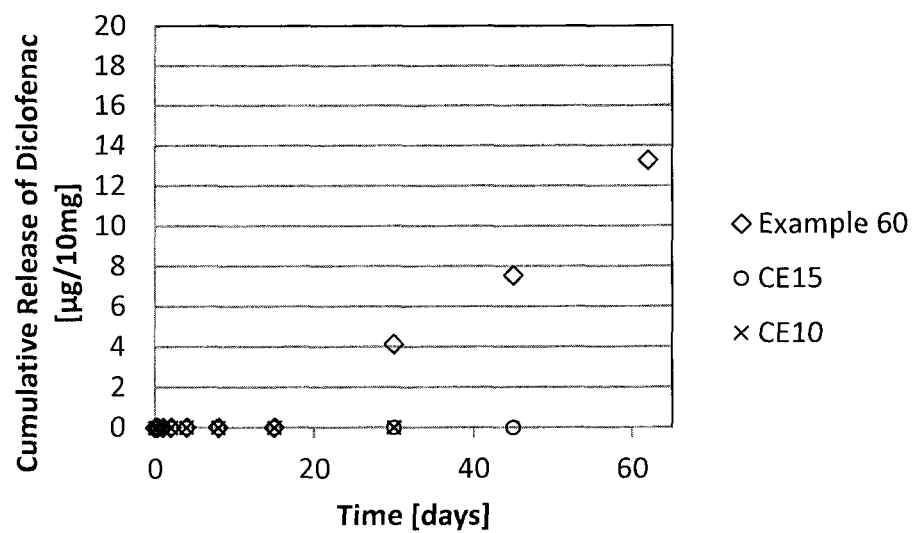
FIG. 2 is a graph illustrating the cumulative release of the NSAID diclofenac over time from polymer-NSAID conjugates comprising the NSAID conjugated via an aryl ester in accordance with an embodiment of the invention and a comparative polymer-NSAID conjugates.

FIG. 2 shows the effect of conjugation via an aryl ester on NSAID release. It was observed that NSAID released from the polymer conjugate of the invention (Example 60), whereas no NSAID release was seen from the comparative examples CE10 and CE15, despite a hydrophilic component being associated with CE10.

Figure 3:
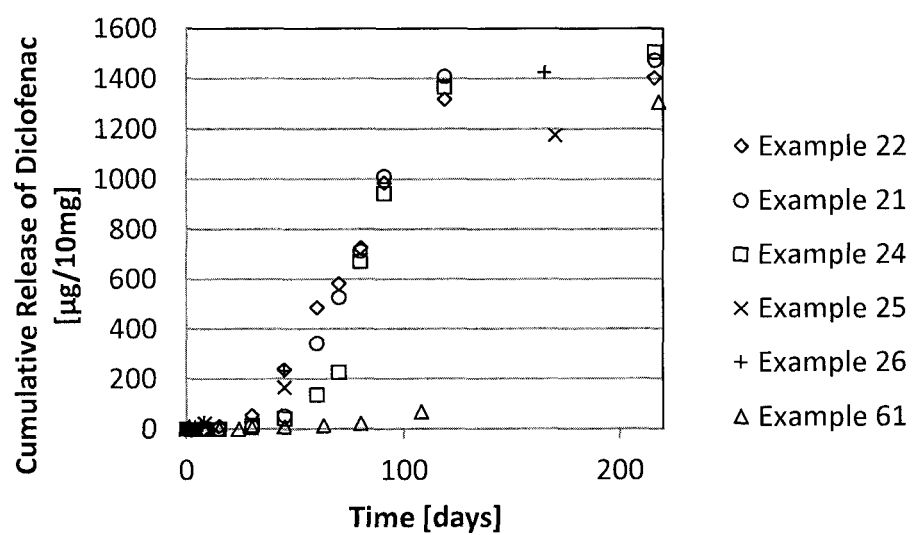
FIG. 3 is a graph illustrating the cumulative release of the NSAID diclofenac over time from polymer-NSAID conjugates having polymer backbones comprising various ester components in accordance with embodiments of the invention.

FIG. 3 shows release of diclofenac from a series of polymer-NSAID conjugates of the invention comprising a poly(urethane-ester) backbone having various polyester components. NSAID release was seen with all conjugates.

Figure 4A:
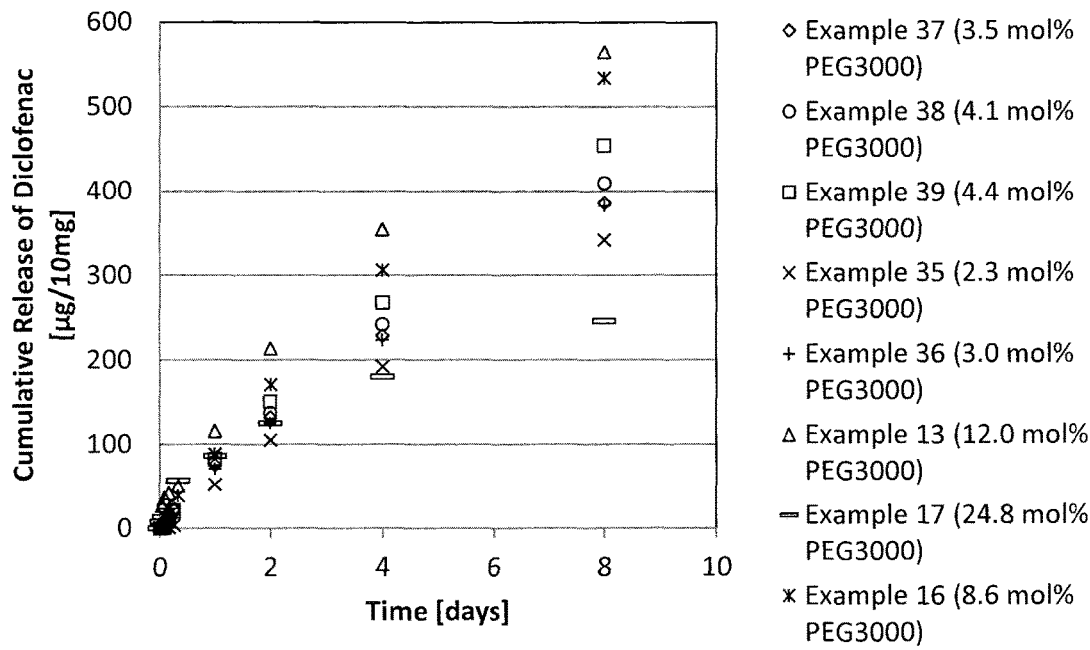
FIG. 4 shows (a) a graph illustrating the cumulative release of the NSAID diclofenac over time from polymer-NSAID having polymer backbones with varying amounts of poly(ethylene glycol) in accordance with embodiments of the invention and (b) a graph illustrating the rate of drug release with respect to the mol % of poly(ethylene glycol) in the conjugate.
Figure 4B:
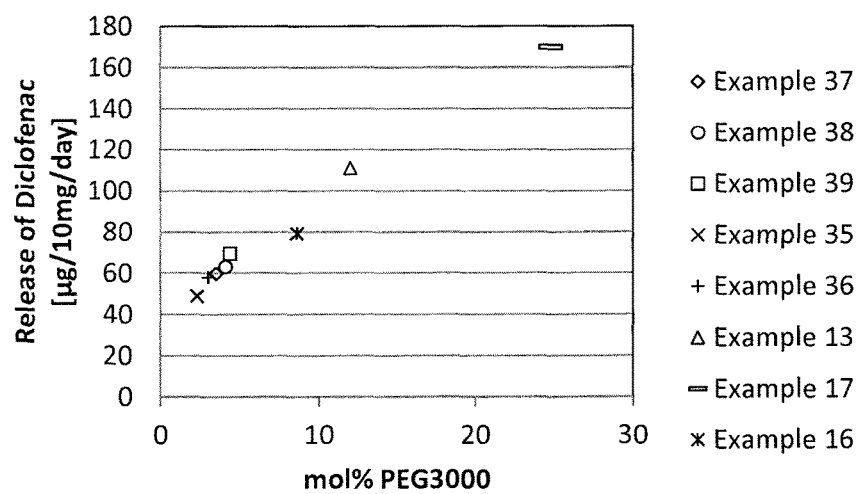

FIG. 4(a) shows the effect of a hydrophilic component on NSAID release. The conjugates tested all contain the same NSAID (diclofenac), the same aryl ester linkage and are prepared with the same polyisocyanate co-monomer. Each polymer-NSAID conjugate incorporates a different amount of PEG3000 in its polymer backbone, ranging from 2.3 mol % to 25 mol %. FIG. 4(b) shows that an increase in the mol % of PEG3000 gives an increased rate of NSAID release, and that a linear relationship exists between the rate of NSAID release and the mol % of PEG3000 incorporated into the polymer chain.

Figure 5:
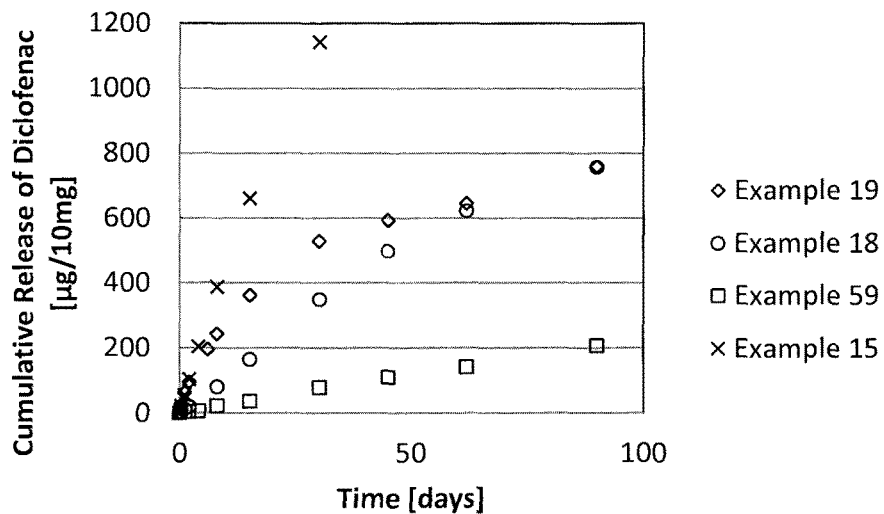
FIG. 5 is a graph illustrating the cumulative release of the NSAID diclofenac over time from polymer-NSAID conjugates formed with the ethyl ester of lysine diisocyanate (ELDI) in accordance with embodiments of the invention.

FIG. 5 shows the release of NSAID from polymer-NSAID conjugates prepared with the ethyl ester of lysine diisocyanate and containing a hydrophilic group of different chain length of ethylene glycol segments. The data demonstrates that immediate NSAID release occurs irrespective of ethylene glycol chain length, with the rate of diclofenac release increasing as the chain length of polyethylene glycol increases.

Figure 6:
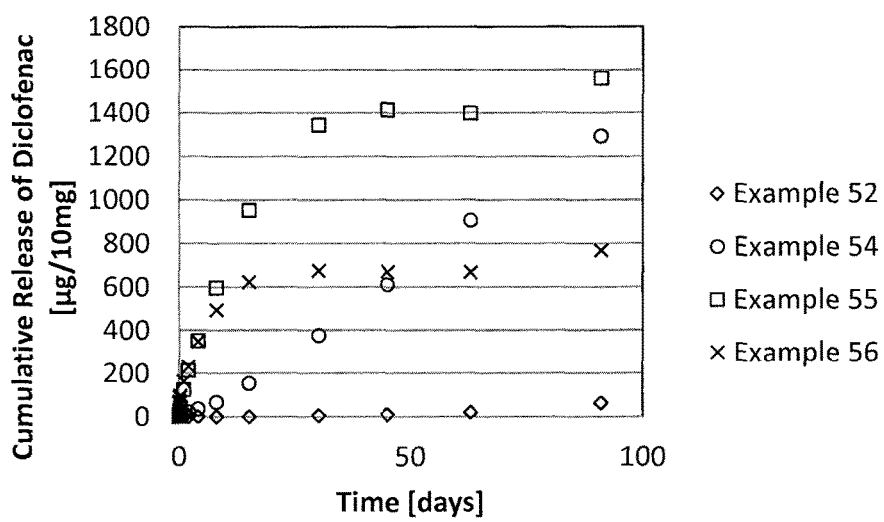
FIG. 6 is a graph illustrating the cumulative release of the NSAID diclofenac over time from polymer-NSAID conjugates formed with hexamethylene diisocyanate (HDI) in accordance with embodiments of the invention.

FIG. 6 shows release of NSAID from polymer-NSAID conjugates prepared with hexamethylene diisocyanate and containing a hydrophilic group of different chain length of ethylene glycol segments. Example 55 and Example 56 show diclofenac-polyurethane-polyethylene glycol constructs with different stoichiometries of PEG3000 (polyethylene glycol, molecular weight 3000) and PEG1000 (polyethylene glycol, molecular weight 1000), respectively. The rate of diclofenac release of these two conjugates is very similar over the release period, but reaches different levels of drug depletion due to the different drug loadings associated with the difference in stoichiometry.

Figure 7:
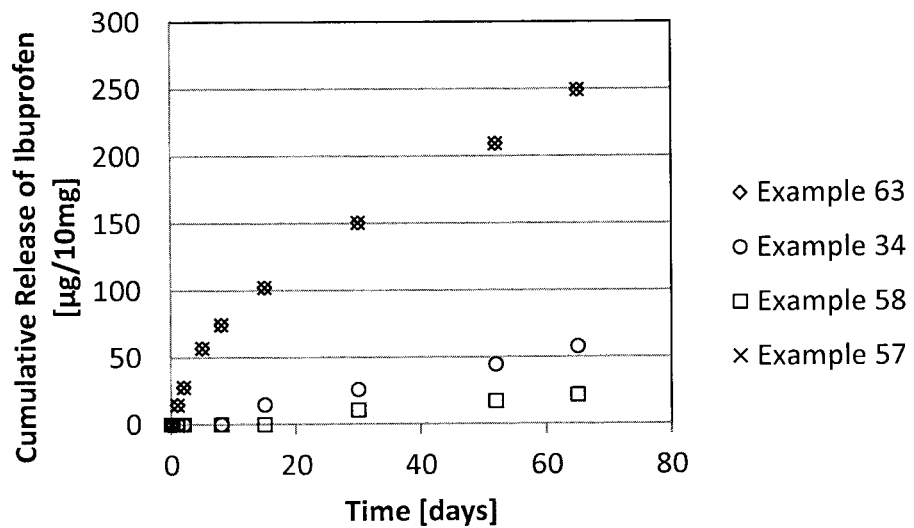
FIG. 7 is a graph illustrating the cumulative release of the NSAID ibuprofen over time from polymer-NSAID conjugates comprising the NSAID conjugated via an aryl ester in accordance with embodiments of the invention.

FIG. 7 shows release of ibuprofen from NSAID-polymer conjugates containing a hydrophilic group of different chain length of ethylene glycol segments and prepared with the same co-monomer, (the ethyl ester of lysine diisocyanate). The data shows that immediate release of NSAID is achieved.

Figure 8:
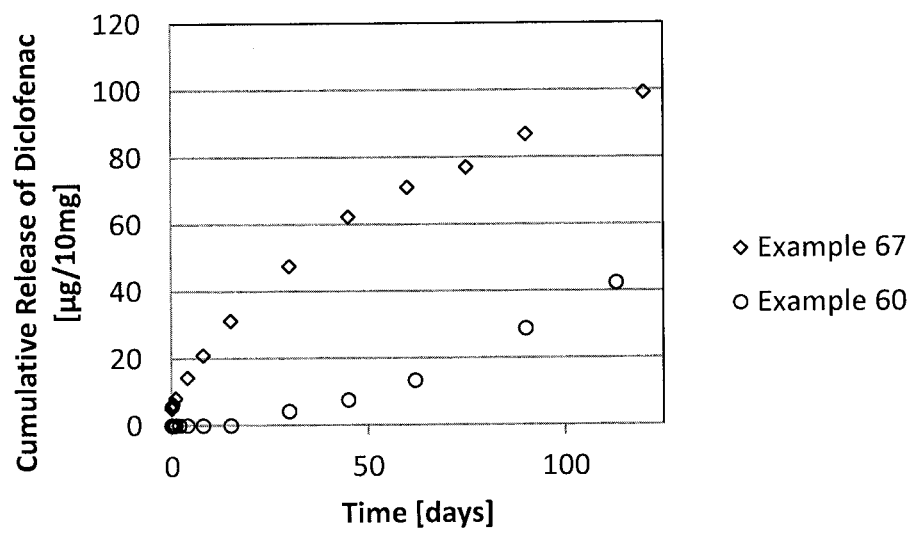
FIG. 8 is a graph illustrating the cumulative release of the NSAID diclofenac over time from a polymer-NSAID conjugate and from a NSAID drug delivery system in accordance with embodiments of the invention.

FIG. 8 shows release of NSAID from a NSAID-polymer conjugate without any hydrophilic component (Example 60) and from a drug delivery system comprising a polymer-NSAID conjugate blended with a hydrophilic polymer (Example 67). The addition of a hydrophilic component facilitates release of the NSAID irrespective of whether the hydrophilic component is incorporated into the polymer chain or in admixture with the NSAID-polymer conjugate.

Figure 9:
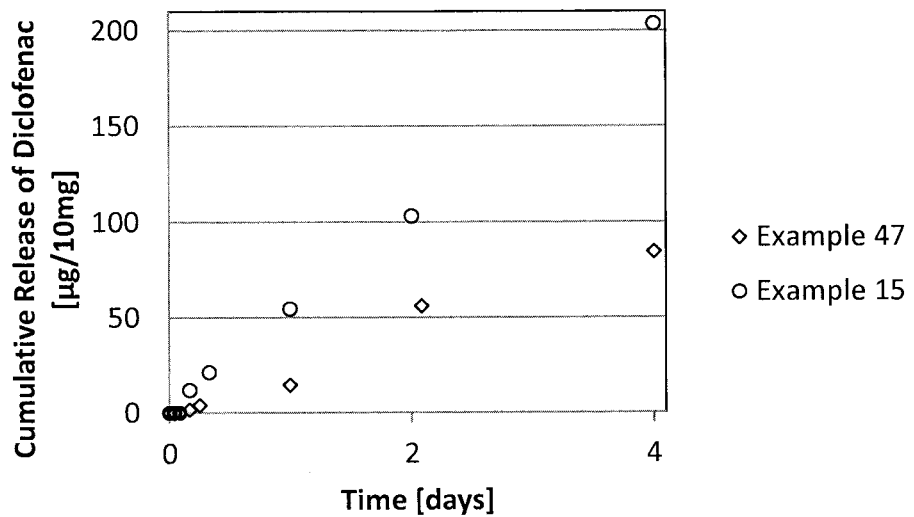
FIG. 9 is a graph illustrating the cumulative release of the NSAID diclofenac over time from polymer-NSAID conjugates comprising the NSAID conjugated via different aryl esters in accordance with embodiments of the invention.

FIG. 9 shows effect of different aryl esters on NSAID release from NSAID-polymer conjugates in accordance with the invention. Both constructs were prepared with the same NSAID (diclofenac), the same hydrophilic component (PEG3000), and the same co-monomer (ethyl ester of lysine diisocyanate). Example 47 (5.0 mol %, PEG3000) uses phloroglucinolto provide the aryl ester, whereas, Example 15 (4.4 mol %, PEG3000) uses para-hydroxy benzoate-2-monoglyceride to provide the aryl ester. Immediate release of diclofenac with zero order or near zero-order release is seen with both conjugates.

Figure 10:
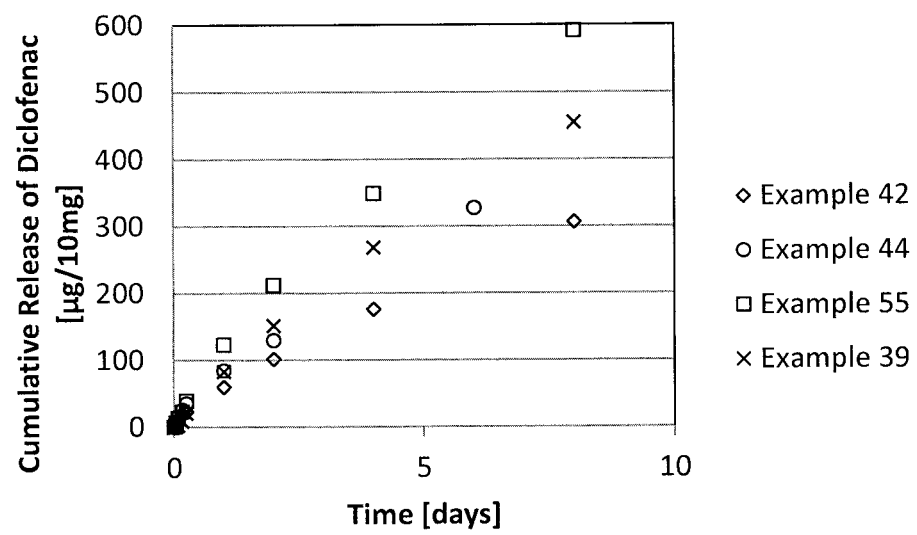
FIG. 10 is a graph illustrating the cumulative release of the NSAID diclofenac over time from polymer-NSAID conjugates comprising various R groups in accordance with embodiments of the invention.

FIG. 10 shows the results of NSAID release from NSAID-polymer conjugates having different R-groups and prepared with different polyisocynate co-monomers. All constructs are made from the same NSAID (diclofenac) and same hydrophilic component (PEG3000). Example 42 (PEG3000, 5.0 mol %) and Example 44 (PEG3000, 5.0 mol %) have the same aryl ester linkage but are prepared with different polyisocyanate co-monomers. Example 55 (PEG3000, 4.5 mol %) and Example 39 (PEG3000, 4.4 mol %) each have the same aryl ester linkage, although the aryl ester is different to that used in Examples 42 and 44 and are also prepared with the same variation of polyisocyanate co-monomers. Immediate release of diclofenac released at similar rates is seen with all conjugates.

Figure 11A:
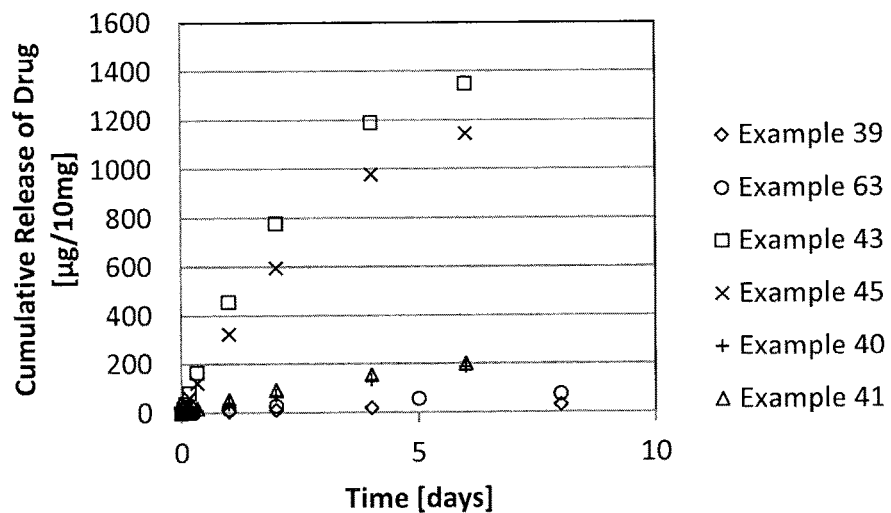
FIG. 11 shows (a) a graph illustrating the cumulative release of various NSAIDs from a polymer-NSAID conjugates of embodiments of the invention and (b) an exploded section of the graph shown in (a).
Figure 11B:
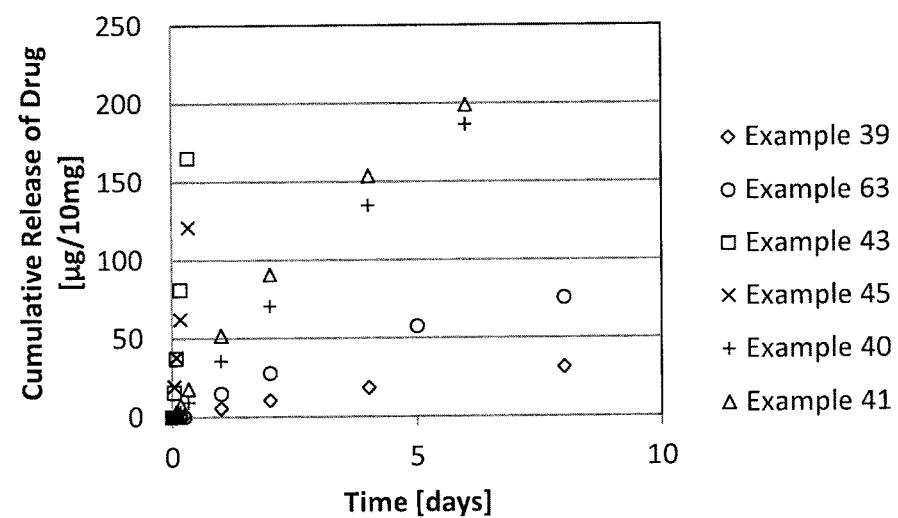

FIG. 11 shows the release of different NSAIDs of the aryl acetic acid class from various polymer conjugates of the invention. All conjugates were prepared with one of two aryl esters, the same hydrophilic component (PEG3000, 4.5-5 mol %) and the same co-monomer (the ethyl ester of lysine diisocyanate).

Figure 12:
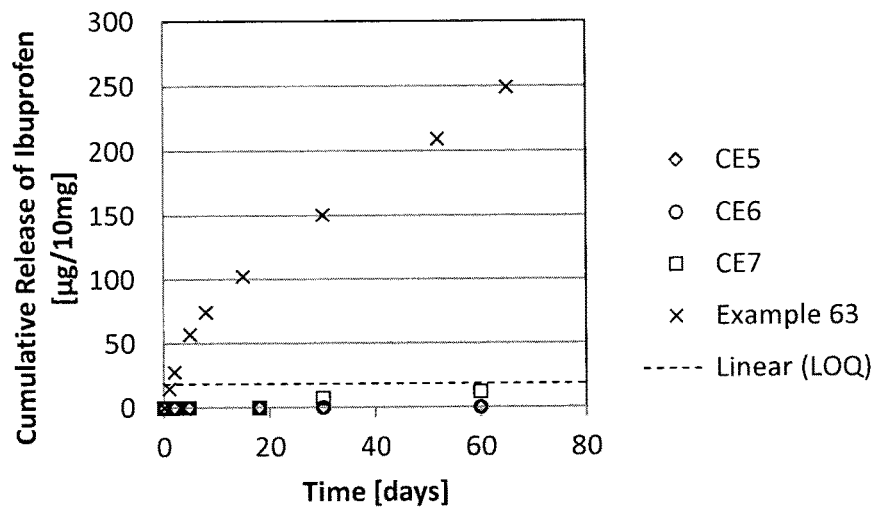
FIG. 12 is a graph illustrating the cumulative release of the NSAID ibuprofen over time from comparative polymer-NSAID conjugates and from a polymer-NSAID conjugate of an embodiment of the invention.

FIG. 12 shows release results from comparative examples CE5, CE6 and CE7 in which the NSAID is conjugated via an alkyl ester. The results show that the comparative polymer conjugates do not release NSAID, whereas Example 63 in accordance with the invention does release NSAID.

Figure 13:
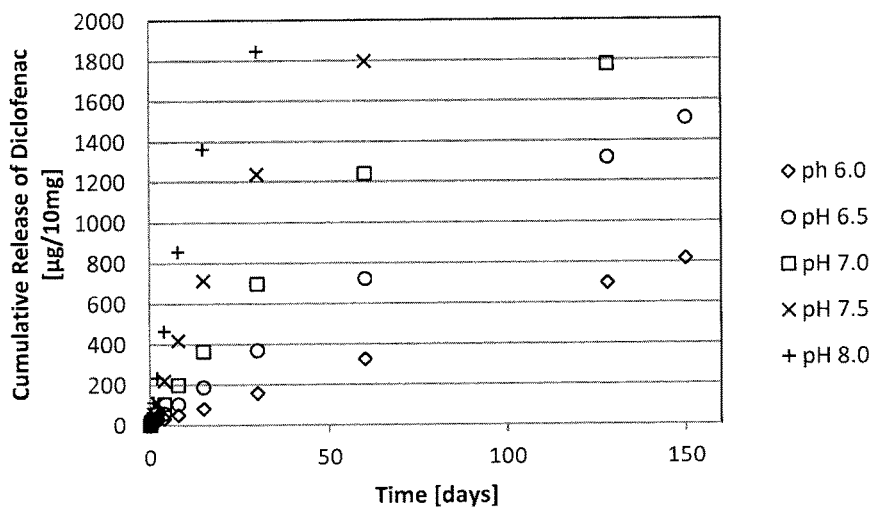
FIG. 13 is a graph illustrating the cumulative release of the NSAID diclofenac over time from a polymer-NSAID conjugate of an embodiment of the invention with respect to variation in pH.

FIG. 13 shows the change in rate of NSAID release as a function of pH of the receptor solution. The data shows that the rate of drug release increases as the pH of the receptor solution increases within the range 6.0 to 8.0. The pH range of 6.0 to 8.0 corresponds to the pH range seen in an active wound.

Implant Production

The polymer-NSAID conjugate or material containing the polymer-NSAID conjugate can be formed into a device suitably shaped to facilitate delivery. One such device is a rod-shaped implant able to be housed within the lumen of a 20 to 30 gauge needle. The outer diameter of the implant would be about 0.6 mm to 0.1 mm, preferably 0.5 to 0.3 mm, and more preferably 0.4 mm. The length of the implant can be selected to deliver the required dose of drug, One method that could be used to produce the rod-shaped implant would involve melt-extrusion, where the polymer-NSAID conjugate or material containing the drug polymer conjugate is forced under pressure and at elevated temperatures through a die to provide a continuous feed of rod-shaped material with an outer diameter of 0.4 mm. The rod-shaped material may then be cut with a hot knife at predefined intervals to provide the final implant.

In one example a basic plunger based extruder is used to produce the implant. Firstly, a barrel is charged with the material to be extruded. At one end of the barrel is a die with a single cylindrical shaped hole about 0.4 mm in diameter from which the material extrudes. At the other end of the barrel is a plunger that forces the contents of the barrel through the die at a constant rate. The barrel and die are heated to ensure the material within the barrel and extruded are at or close to their melting point (typically greater than 70° C.).

In another example a single screw extruder is used to produce the implant. The material to be extruded enters through a feed throat (an opening near the rear of the barrel) and comes into contact with the screw. The rotating screw (normally turning at up to 120 rpm) forces the material forward into the barrel which is heated to the desired melt temperature of the molten plastic (typically greater than 70° C.). Typically, heating zones gradually increase the temperature of the barrel from the rear (where the plastic enters) to the front (where the die is located). This allows the material to melt gradually as it is pushed through the barrel and lowers the risk of overheating which may cause degradation in the polymer. The high pressure and friction of the material inside the barrel also contributes heat to the process. Also the extruder can be operated in a constant flow rate mode with the pressure varied to maintain flow of material or constant pressure mode with the rate of screw rotation varied to maintain a constant pressure. After passing through the barrel the molten material enters the die, which gives the final product its profile.

The exudate from the die of either of these two methods must be cooled and this is usually achieved by pulling the exudate through a water bath or a cooling curtain of air.

It is to be understood that various other modifications and/or alterations may be made without departing from the spirit of the present invention as outlined herein.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The invention claimed is:

1. A polymer-NSAID conjugate comprising (i) a biodegradable polymer backbone and (ii) a substituted alkanoic acid non-steroidal anti-inflammatory drug (NSAID), wherein the NSAID is conjugated pendant to the polymer backbone via an aryl-ester linkage comprising a carboxylic acid residue (—C(=O)—) of the NSAID and an oxygen substituent of an aryl group pendant from or present in the polymer-backbone.

2. A polymer-NSAID conjugate comprising a biodegradable polymer backbone and a substituted alkanoic acid non-steroidal anti-inflammatory drug (NSAID) conjugated pendant to the polymer backbone, wherein the conjugate comprises pendant to its polymer backbone an aryl: ester linked moiety of formula (I):

where:
R comprises an optionally substituted aliphatic or an optionally substituted aryl group of the polymer backbone;
X is a bond or a linking group;
Ar is an optionally substituted aryl group;
D is the NSAID conjugated pendant to the polymer backbone via an aryl-ester linkage comprising a carboxylic acid residue (—C(=O)—) of the NSAID and the —O— of formula (I); and
n is an integer selected from 0 and 1, wherein when n is 0 then X is a bond,
with the proviso that when R comprises an optionally substituted aliphatic group then n is 1, and when R comprises an optionally substituted aryl group then n is 0 or 1.

3. A polymer-NSAID conjugate according to claim 2, wherein the moiety of formula (I) has a structure of formula (Ia):

where:
R¹ comprises an optionally substituted aliphatic group of the polymer backbone;
X is a bond or a linking group;
Ar is an optionally substituted aryl group;
D is the NSAID conjugated pendant to the polymer backbone via an aryl-ester linkage comprising a carboxylic acid residue (—C(=O)—) of the NSAID and the —O— of formula (Ia); and
n is 1.

4. A polymer-NSAID conjugate according to claim 2 wherein Ar is comprised of from 5 to 12 ring members.

5. A polymer-NSAID conjugate according to claim 2, wherein Ar is an optionally substituted $C_5$-$C_{12}$ aryl group.

6. A polymer-NSAID conjugate according to claim 2 wherein X is an optionally substituted linking group comprising a functional group selected from the group consisting of —O—, —C(O)O—, —OC(O)—, —C(O)—, —OC(O)NH—, —NHC(O)O—, —OC$_6$H$_4$O—, —OC(O)[CH$_2$]$_n$— where n is an integer from 1 to 5, —C(O)NR$^a$— and —NR$^a$C(O)—, where R$^a$ is H or $C_1$-$C_4$ alkyl.

7. A polymer-drug conjugate according to claim 2, wherein the group —X—(Ar)n-O— is —OC(O)—$C_{5-12}$aryl-O—.

8. A polymer-NSAID conjugate according to claim 2, wherein the moiety of formula (I) is:

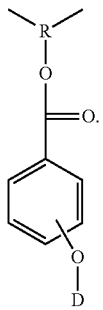

9. A polymer-NSAID conjugate according to claim 1, wherein the polymer backbone comprises a polymer selected from the group consisting of polyester polymers, polyanhydride polymers, polycarbonate polymers, polyamide polymers, polyimide polymers, polyurethane polymers, polyurea polymers, polysaccharides, polypeptides, copolymers thereof, and combinations thereof.

10. A polymer-NSAID conjugate according to claim 1, wherein the conjugate comprises as a part of its polymer backbone a plurality of moieties of formula (II):

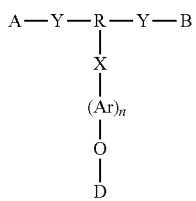

where:
A and B, which may be the same or different, each represent a biodegradable polymer backbone and are attached to the —Y—R(X—(Ar)n-O-D)-Y— moiety via a biodegradable moiety, and, optionally, at least one of A and B comprises a hydrophilic group;
R comprises an optionally substituted aliphatic group or an optionally substituted aryl group;
Y at each occurrence is independently selected from the group consisting of —O—, —C(O)— and —NR$^a$—, where R$^a$ is H or $C_1$-$C_4$ alkyl;
X is a bond or a linking group;
Ar is an optionally substituted aryl group;
D is the NSAID conjugated pendant to the polymer backbone via an aryl-ester linkage comprising a carboxylic acid residue (—C(=O)—) of the NSAID and the —O— of formula (II); and
n is an integer selected from 0 and 1, wherein when n is 0 then X is a bond,
with the proviso that when R comprises an optionally substituted aliphatic group then n is 1, and when R comprises an optionally substituted aryl group then n is 0 or 1.

11. A polymer-NSAID conjugate according to claim 1, wherein the conjugate comprises a hydrophilic group.

12. A polymer-NSAID conjugate according to claim 11, wherein the hydrophilic group is incorporated in the conjugate (i) as part of the polymer backbone, (ii) in a pendant group covalently attached to and pendant from the polymer backbone, or both.

13. A polymer-NSAID conjugate according to claim 11, wherein the hydrophilic group comprises at least one selected from the group consisting of poly(ethylene glycol), poly(lactic acid-co-glycolic acid) (PLGA), poly(1,5-dioxepan-2-one) (PDOO), poly(glycerol acetate) (PGAc), poly(hydroxy butyrate), poly(glycerol phosphate), an amino acid polymer selected from (polylysine and polyglutamic acid), an amino acid oligomer, a C2-C4 diol, such as (glycerol), mannitol, xylitol, sorbitol, an amino acid, lactic acid, glycolic acid, a hydroxy acid, 1,5-dioxepan-2-one, glycerol acetate, glycerol phosphate, or combinations thereof, or copolymers thereof.

14. A polymer-NSAID conjugate according to claim 2, wherein the substituted alkanoic acid NSAID has a structure according to formula (III):

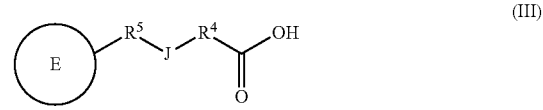

where:
E represents an optionally substituted ring system;
J is selected from the group consisting of a bond or a functional group; and
R⁴ and R⁵ are each independently selected from the group consisting of a bond and an optionally substituted aliphatic group.

15. A polymer-NSAID conjugate according to claim 14, wherein the NSAID of formula (III) has a structure of formula (IIIa):

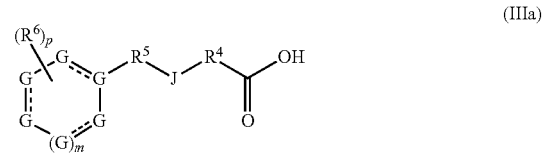

where:
- G at each occurrence is independently selected from the group consisting of a carbon atom and a heteroatom;
- ------------- represents an optional bond;
- $R^6$ is a substituent group;
- p represents the number of substituent groups and is an integer from 0 to 5;
- m is 0 or 1;
- J is selected from the group consisting of a bond or a functional group; and
- $R^4$ and $R^5$ are each independently selected from the group consisting of a bond and an optionally substituted aliphatic group.

16. A polymer-NSAID conjugate according to claim 2, wherein the substituted alkanoic acid NSAID is selected from the group consisting of aceclofenac, alminoprofen, amfenac, carprofen, diclofenac, enfenamic acid, etodolac, flufenamic acid, meclofenamic acid, mefenamic acid, niflumic acid, tolfenamic acid bendazac, benoxaprofen, bermoprofen, bucloxic acid, butibufen, cinmetacin, clidanac, clopirac, dexibuprofen, dexketoprofen, felbinac, fenbufen, fenclozic acid, fenoprofen, fentiazac, flunoxaprofen, flunixin, flurbiprofen, ibuprofen, indomethacin, isofezolac, isoxepac, ketoprofen, licofelone, lonazolac, loxoprofen, lumiracoxib, metiazinic acid, mofezolac, naproxen, oxaprozin, pirazolac, pirprofen, pranoprofen, protizinic acid, sulindac, suprofen, tiaprofenic acid, tolmetin, bermoprofen, bucloxic acid, isoxepac, ketoprofen, loxoprofen, zaltoprofen, balsalazide, fendosal, olsalazine, ximoprofen, mesalamine, sulfasalazine, acetylsalicylsalicylic acid, alclofenac, aspirin, benoxaprofen, 5-bromosalicylic acid acetate, cinchophen, diacerein, dipyrocetyl, fosfosal, ibufenac, indoprofen, clometacin, ketorolac, zomepirac, actarit, clonixin, salicylamide O-acetic acid, diflunisal, gentisic acid, and salsalate.

17. A polymer-NSAID conjugate comprising a biodegradable polymer backbone and a substituted alkanoic acid non-steroidal anti-inflammatory drug (NSAID) conjugated pendant to the polymer backbone via an aryl-ester linkage, wherein the polymer-NSAID conjugate is a copolymer of a NSAID-monomer conjugate of formula (IV):

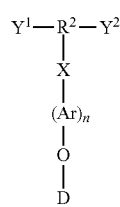

(IV)

where:
- $Y^1$ and $Y^2$ each independently represent a reactive functional group, or $Y^1$ and $Y^2$ together form part of a cyclic group capable of ring-opening;
- R comprises an optionally substituted aliphatic group or an optionally substituted aryl group;
- X is a bond or a linking group;
- Ar is an optionally substituted aryl group;
- D is the NSAID conjugated pendant to the polymer backbone via an aryl-ester linkage comprising a carboxylic acid residue (—C(=O)—) of the NSAID and the —O— of formula (IV); and
- n is an integer selected from 0 and 1, wherein when n is 0 then X is a bond,
- with the proviso that when R comprises an optionally substituted aliphatic group then n is 1, and when R comprises an optionally substituted aryl group then n is 0 or 1;

with at least one monomer comprising compatible chemical functionality and, optionally, at least one co-monomer.

18. A polymer-NSAID conjugate according to claim 17, wherein $Y^1$ and $Y^2$ are functional groups independently selected from the group consisting of hydroxy, isocyanate, thiol, anhydride, carboxylic acid, carboxylic acid ester, carboxylic acid halide and amine groups.

19. A polymer-NSAID conjugate according to claim 17, wherein the copolymer comprises the co-monomer which comprises a polymeric or oligomeric moiety selected from the group consisting of poly(ethylene glycol), poly(lactic acid-co-glycolic acid) (PLGA), poly(1,5-dioxepan-2-one) (PDOO), poly(glycerol acetate) (PGAc), poly(hydroxy butyrate), poly(glycerol phosphate), an amino acid polymer, and an amino acid oligomer.

20. A polymer-NSAID conjugate according to claim 17, wherein the substituted alkanoic acid NSAID has a structure according to formula (III):

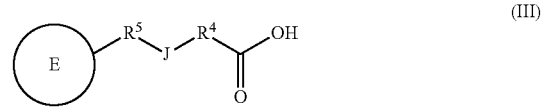

(III)

where:
- E represents an optionally substituted ring system;
- J is selected from the group consisting of a bond or a functional group;
- $R^4$ and $R^5$ are each independently selected from the group consisting of a bond and an optionally substituted aliphatic group.

* * * * *